US009078458B2

(12) United States Patent
Gregg

(10) Patent No.: US 9,078,458 B2
(45) Date of Patent: Jul. 14, 2015

(54) COMPOSITION FOR CONTROLLING FISH

(75) Inventor: Kenneth William Gregg, Atlanta, GA (US)

(73) Assignee: Kenneth William Gregg, Atlanta, GA (US)

( * ) Notice: Subject to any disclaimer, the term of this patent is extended or adjusted under 35 U.S.C. 154(b) by 70 days.

(21) Appl. No.: 12/718,506

(22) Filed: Mar. 5, 2010

(65) Prior Publication Data

US 2010/0226876 A1 Sep. 9, 2010

Related U.S. Application Data

(60) Provisional application No. 61/158,121, filed on Mar. 6, 2009.

(51) Int. Cl.

| | |
|---|---|
| ***A01N 63/02*** | (2006.01) |
| ***A23K 1/18*** | (2006.01) |
| ***A23K 1/00*** | (2006.01) |

(52) U.S. Cl.

CPC ................. *A23K 1/188* (2013.01); *A23K 1/004* (2013.01); *A23K 1/009* (2013.01)

(58) Field of Classification Search

None

See application file for complete search history.

(56) References Cited

U.S. PATENT DOCUMENTS

| | | | | |
|---|---|---|---|---|
| 3,615,695 | A * | 10/1971 | Luksas | 426/43 |
| 4,202,905 | A * | 5/1980 | Asai et al. | 426/1 |
| 5,498,414 | A * | 3/1996 | Thornton et al. | 424/234.1 |
| 5,674,518 | A * | 10/1997 | Fajt | 424/408 |
| 7,204,993 | B2 * | 4/2007 | Evans et al. | 424/244.1 |
| 8,182,855 | B2 * | 5/2012 | Axelrod | 426/457 |
| 2003/0190658 | A1 * | 10/2003 | Beck et al. | 435/6 |

OTHER PUBLICATIONS

Beveridge et al. "The ingestion of bacteria in suspension by the common carp *Cyprinus carpio*". Journal of Fish Biology. 1991, 39, 825-831.*

Cahill M.M. "Bacterial flora of fishes: a review". Microb. Ecol. 1990,19:21-41.*

Austin B. "The future of bacterial fish vaccine". Vaccine, 1984, vol. 2, pp. 249-254.*

Aly et al. "Characterization of some bacteria isolated from *Oreochromis niloticus* and their potential use as probiotics". Aquaculture. 2008, 277, pp. 1-6).*

Asgard et al. "*Casein silage* as feed for salmonids". Aquaculture. 1985, 48, pp. 233-252.*

Nikoskelainene et al. "Protection of rainbow trout from furunculosis by *Lactobacillus rhamnosus*". Aquaculture. 2001, 198, pp. 229-236.*

Perrone et l. Industria el Latte, 1999, 35(1-2), 3-21; English abstract: STN Caplus abstract accession No. 2000:254246.*

Modern Food Microbiology. 2008, Chapter 2, pp. 13-37.*

Derby. "Neural Processing, Perception, and Behavioral Responses to Natural Chemical Stimuli by Fish and Crustaceans." J Chem Ecol (2008) 34:898-914.

ILkRA. "Olfaction and gustation in fish: an overview." Acta Physiol Scand 1994, 152, 207 17.

Shephard. "Functions for fish mucous." Rev. in Fish Biology &Fisheries, 4, 401-29 (1994).

Wang. "Identification of the adherent microbiota on the gills and skin of poly-cultured gibel carp (*Carassius auratus* gibelio) and bluntnose black bream (*Megalobrama amblycephala* Yih)." Aquaculture Research, 2010, 41, e72-e83.

Kasumyan. "Taste preferences in fish and prospects for application of taste stimulants in aquaculture." (2004) *Proceedings of the Fourth International Iran & Russia Conference*.

Gallagher. "The use of soybean meal as a replacement for fish meal in diets for hybrid striped bass (*Morone saxatilis* X Ad. chrysops)." Aquaculture V.126, I.1-2, 1994, pp. 119-127.

McFarland. "Can Fish Smell Underwater?" *Outdoor*Illinois Jul. 2008.

Saha. "Comparative Toxicity of Three Organic Acids to Freshwater Organisms and Their Impact on Aquatic Ecosystems." Human and Ecological Risk Assessment, 12: 192-202, 2006.

Austin. "The Bacterial Microflora of Fish." ScientificWorldJournal (2006) 6, 931-945.

De Silva. Chapman & Hall Aquaculture Series 1. Fish Nutrition in Aquaculture pp. 213, 215-216. 1995. ISBN 041255030.

* cited by examiner

*Primary Examiner* — Vera Afremova

(74) *Attorney, Agent, or Firm* — Judy Jarecki-Black; Chad Kitchen; Merial, Inc.

(57) ABSTRACT

The present invention relates to a composition for controlling fish. In particular, the composition may be an incitant, functioning as either a fish attractant or a fish repellent. The composition may be prepared by extracting bacteria from a source fish, culturing the bacteria in an appropriate media, and subsequently combining the cultured bacteria with a substrate to form the composition.

35 Claims, 11 Drawing Sheets

Figure 9

| SEQ ID NO | DNA/PRT | Description |
|---|---|---|
| 1 | DNA | Br1-1-10-27F_E10.ab1 |
| 2 | DNA | Br1-1-11-27F_E11.ab1 |
| 3 | DNA | Br1-1-12-27F_E12.ab1 |
| 4 | DNA | Br1-1-1-27F_E01.ab1 |
| 5 | DNA | Br1-1-13-27F_F01.ab1 |
| 6 | DNA | Br1-1-14-27F_F02.ab1 |
| 7 | DNA | Br1-1-15-27F_F03.ab1 |
| 8 | DNA | Br1-1-16-27F_F04.ab1 |
| 9 | DNA | Br1-1-17-27F_F05.ab1 |
| 10 | DNA | Br1-1-18-27F_F06.ab1 |
| 11 | DNA | Br1-1-19-27F_F07.ab1 |
| 12 | DNA | Br1-1-20-27F_F08.ab1 |
| 13 | DNA | Br1-1-22-27F_F10.ab1 |
| 14 | DNA | Br1-1-2-27F_E02.ab1 |
| 15 | DNA | Br1-1-23-27F_F11.ab1 |
| 16 | DNA | Br1-1-24-27F_F12.ab1 |
| 17 | DNA | Br1-1-3-27F_E03.ab1 |
| 18 | DNA | Br1-1-4-27F_E04.ab1 |
| 19 | DNA | Br1-1-5-27F_E05.ab1 |
| 20 | DNA | Br1-1-6-27F_E06.ab1 |
| 21 | DNA | Br1-1-7-27F_E07.ab1 |
| 22 | DNA | Br1-1-8-27F_E08.ab1 |
| 23 | DNA | Br1-1-9-27F_E09.ab1 |
| 24 | DNA | FM-1-10-27F_G03.ab1 |
| 25 | DNA | FM-1-11-27F_G04.ab1 |
| 26 | DNA | FM1-1-1-27F_F06.ab1 |
| 27 | DNA | FM-1-12-27F_G05.ab1 |
| 28 | DNA | FM1-1-2-27F_F07.ab1 |
| 29 | DNA | FM-1-13-27F_G06.ab1 |
| 30 | DNA | FM1-1-3-27F_F08.ab1 |
| 31 | DNA | FM-1-14-27F_G07.ab1 |
| 32 | DNA | FM1-1-4-27F_F09.ab1 |
| 33 | DNA | FM-1-15-27F_G08.ab1 |
| 34 | DNA | FM1-1-6-27F_F11.ab1 |
| 35 | DNA | FM1-1-7-27F_F12.ab1 |
| 36 | DNA | FM-1-8-27F_G01.ab1 |
| 37 | DNA | FM-1-9-27F_G02.ab1 |
| 38 | DNA | Gam1-1-10-27F_C10.ab1 |
| 39 | DNA | Gam1-1-11-27F_C11.ab1 |
| 40 | DNA | Gam1-1-12-27F_C12.ab1 |
| 41 | DNA | Gam1-1-1-27F_C01.ab1 |

Figure 9 (Continued)

| SEQ ID NO | DNA/PRT | Description |
|---|---|---|
| 42 | DNA | Gam1-1-13-27F_G06.ab1 |
| 43 | DNA | Gam1-1-15-27F_G08.ab1 |
| 44 | DNA | Gam1-1-16-27F_G09.ab1 |
| 45 | DNA | Gam1-1-17-27F_G10.ab1 |
| 46 | DNA | Gam1-1-18-27F_G11.ab1 |
| 47 | DNA | Gam1-1-19-27F_G02.ab1 |
| 48 | DNA | Gam1-1-20-27F_H01.ab1 |
| 49 | DNA | Gam1-1-21-27F_H02.ab1 |
| 50 | DNA | Gam1-1-22-27F_H03.ab1 |
| 51 | DNA | Gam1-1-2-27F_C02.ab1 |
| 52 | DNA | Gam1-1-24-27F_H05.ab1 |
| 53 | DNA | Gam1-1-25-27F_H06.ab1 |
| 54 | DNA | Gam1-1-26-27F_H07.ab1 |
| 55 | DNA | Gam1-1-27-27F_H08.ab1 |
| 56 | DNA | Gam1-1-28-27F_H09.ab1 |
| 57 | DNA | Gam1-1-29-27F_H10.ab1 |
| 58 | DNA | Gam1-1-30-27F_H11.ab1 |
| 59 | DNA | Gam1-1-32-27F_B01.ab1 |
| 60 | DNA | Gam1-1-3-27F_H02.ab1 |
| 61 | DNA | Gam1-1-33-27F_B02.ab1 |
| 62 | DNA | Gam1-1-35-27F_B04.ab1 |
| 63 | DNA | Gam1-1-36-27F_B05.ab1 |
| 64 | DNA | Gam1-1-37-27F_B06.ab1 |
| 65 | DNA | Gam1-1-38-27F_B07.ab1 |
| 66 | DNA | Gam1-1-39-27F_B08.ab1 |
| 67 | DNA | Gam1-1-40-27F_B09.ab1 |
| 68 | DNA | Gam1-1-4-27F_C04.ab1 |
| 69 | DNA | Gam1-1-5-27F_C05.ab1 |
| 70 | DNA | Gam1-1-6-27F_C06.ab1 |
| 71 | DNA | Gam1-1-7-27F_C07.ab1 |
| 72 | DNA | Gam1-1-8-27F_C08.ab1 |
| 73 | DNA | Gam1-1-9-27F_C09.ab1 |
| 74 | DNA | Gam1-1-41-27F_B10.ab1 |
| 75 | DNA | Gam1-1-42-27F_B11.ab1 |
| 76 | DNA | Gam1-1-43-27F_B12.ab1 |
| 77 | DNA | GS1-1-1-27F_H01.ab1 |
| 78 | DNA | GS1-1-2-27F_H02.ab1 |
| 79 | DNA | GS1-1-3-27F_H03.ab1 |
| 80 | DNA | GS1-1-4-27F_H04.ab1 |
| 81 | DNA | GS1-1-5-27F_H05.ab1 |

SEQUENCE LISTING

```
<160> NUMBER OF SEQ ID NOS: 81

<210> SEQ ID NO 1
<211> LENGTH: 879
<212> TYPE: DNA
<213> ORGANISM: Artificial Sequence
<220> FEATURE:
<223> OTHER INFORMATION: Br1-1-10-27F_E10.ab1
<220> FEATURE:
<221> NAME/KEY: misc_feature
<222> LOCATION: (4)..(5)
```

-continued

<223> OTHER INFORMATION: n is a, c, g, or t
<220> FEATURE:
<221> NAME/KEY: misc_feature
<222> LOCATION: (614)..(616)
<223> OTHER INFORMATION: n is a, c, g, or t
<220> FEATURE:
<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (713)..(714)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (719)..(720)
<223> OTHER INFORMATION: n is a, c, g, or t
<220> FEATURE:
<221> NAME/KEY: misc_feature
<222> LOCATION: (722)..(724)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (775)..(777)
<223> OTHER INFORMATION: n is a, c, g, or t
<220> FEATURE:
<221> NAME/KEY: misc_feature
<222> LOCATION: (787)..(788)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (813)..(814)
<223> OTHER INFORMATION: n is a, c, g, or t
<220> FEATURE:
<221> NAME/KEY: misc_feature
<222> LOCATION: (816)..(817)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (842)..(844)
<223> OTHER INFORMATION: n is a, c, g, or t
<220> FEATURE:
<221> NAME/KEY: misc_feature
<222> LOCATION: (847)..(854)
<223> OTHER INFORMATION: n is a, c, g, or t
<220> FEATURE:
<221> NAME/KEY: misc_feature
<222> LOCATION: (856)..(857)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (875)..(876)
<223> OTHER INFORMATION: n is a, c, g, or t

<400> SEQUENCE: 1

```
tacnntgcag tcgagcggca gcgggaaagt agcttgctac ttttgccggc gagcggcgga     60

cgggtgagta atgcctgggg atctgcccag tcgaggggga taactactgg aaacggtagc    120

taataccgca tacgccctac gggggaaagc aggggacctt cgggccttgc gcgattggat    180

gaacccaggt gggattagct agttggtgag gtaacggctc accaaggcga cgatccctag    240

ctggtctgag aggatgatca gccacactgg aactgagaca cggtccagac tcctacggga    300

ggcagcagtg gggaatattg cacaatgggg gaaaccctga tgcagccatg ccgcgtgtgt    360

gaagaaggcc ttcgggttgt aaagcacttt cagcgaggag gaaaggtcag tagctaatat    420

ctgctggctg tgacgttact cgcagaagaa gcaccggcta actccgtgcc agcagccgcg    480

gtaatacgga gggtgcaagc gttaatcgga attactgggc gtaaagcgca cgcaggcggt    540

tggataagtt agatgtgaaa gccccgggct caacctggga attgcattta aaactgtcca    600

gctagagtct tgannngggg ggtagaattc caggtgntag cggtgaaatg cgtagagatc    660

tggaggaata ccggtggcga aggcggcccc ctgggacaaa gactgacgcc tcnngtngnn    720

annnagncgt ggggagcaac aggattagat accctggnag tccacgccgt aaacnnnatg    780

tcgattnnga ngctgtntct tganacgtgn ctnngnncta cgcgttaaat cgaccgnctg    840

gnnntannnn nnnngnnang ntnaactcaa tgaannacg                           879
```

<210> SEQ ID NO 2
<211> LENGTH: 896
<212> TYPE: DNA
<213> ORGANISM: Artificial Sequence
<220> FEATURE:
<223> OTHER INFORMATION: Br1-1-11-27F_E11.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (615)..(616)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (659)..(661)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:

<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (804)..(805)
<223> OTHER INFORMATION: n is a, c, g, or t
<220> FEATURE:
<221> NAME/KEY: misc_feature
<222> LOCATION: (810)..(811)
<223> OTHER INFORMATION: n is a, c, g, or t
<220> FEATURE:
<221> NAME/KEY: misc_feature
<222> LOCATION: (815)..(816)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (820)..(822)
<223> OTHER INFORMATION: n is a, c, g, or t
<220> FEATURE:
<221> NAME/KEY: misc_feature
<222> LOCATION: (832)..(833)
<223> OTHER INFORMATION: n is a, c, g, or t
<220> FEATURE:
<221> NAME/KEY: misc_feature
<222> LOCATION: (836)..(838)
<223> OTHER INFORMATION: n is a, c, g, or t
<220> FEATURE:
<221> NAME/KEY: misc_feature
<222> LOCATION: (840)..(842)
<223> OTHER INFORMATION: n is a, c, g, or t
<220> FEATURE:
<221> NAME/KEY: misc_feature
<222> LOCATION: (848)..(852)
<223> OTHER INFORMATION: n is a, c, g, or t
<220> FEATURE:
<221> NAME/KEY: misc_feature
<222> LOCATION: (855)..(858)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t
<220> FEATURE:
<221> NAME/KEY: misc_feature
<222> LOCATION: (874)..(875)
<223> OTHER INFORMATION: n is a, c, g, or t
<220> FEATURE:
<221> NAME/KEY: misc_feature
<222> LOCATION: (883)..(885)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t -continued

<400> SEQUENCE: 2

```
tacnntgcaa gtcgagcggc agcgggaaag tagcttgcta cttttgccgg cgagcggcgg     60
acgggtgagt aatgcctggg gatctgccca gtcgaggggg ataactactg gaaacggtag    120
ctaataccgc atacgcccta cgggggaaag caggggacct tcgggccttg cgcgattgga    180
tgaacccagg tgggattagc tagttggtga ggtaacggct caccaaggcg acgatcccta    240
gctggtctga gaggatgatc agccacactg gaactgagac acggtccaga ctcctacggg    300
aggcagcagt ggggaatatt gcacaatggg ggaaaccctg atgcagccat gccgcgtgtg    360
tgaagaaggc cttcgggttg taaagcactt tcagcgagga ggaaaggtca gtagctaata    420
tctgctggct gtgacgttac tcgcagaaga agcaccggct aactccgtgc cagcagccgc    480
ggtaatacgg agggtgcaag cgttaatcgg aattactggg cgtaaagcgc acgcaggcgg    540
ttggataagt tagatgtgaa agccccgggc tcaacctggg aattgcattt aaaactgtcc    600
agctagagtc ttgannaggg ggggtagaat tccaggtgtn agcggtgaaa tgcgtagann    660
nctggaggaa taccgggtgg cgaaaggcgg ccccctgnac aaagactgac gctcngtgcg    720
aaagcgtggg gagcaaacag gattagatac cctggtagtc cacnccgtaa acgatgtcga    780
tttggaggct gngntcttga gacnnggctn ncggnnantn nnagcgctta anntcnnncn    840
nngtgggnnn nntannnncc cncanggnta aaanntcaaa tgnnnttgac nggggg        896
```

<210> SEQ ID NO 3
<211> LENGTH: 851
<212> TYPE: DNA
<213> ORGANISM: Artificial Sequence
<220> FEATURE:
<223> OTHER INFORMATION: Br1-1-12-27F_E12.ab1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (673)..(676)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (690)..(692)
<223> OTHER INFORMATION: n is a, c, g, or t
<220> FEATURE:
<221> NAME/KEY: misc_feature
<222> LOCATION: (704)..(706)
<223> OTHER INFORMATION: n is a, c, g, or t
<220> FEATURE:
<221> NAME/KEY: misc_feature
<222> LOCATION: (810)..(812)
<223> OTHER INFORMATION: n is a, c, g, or t
<220> FEATURE:
<221> NAME/KEY: misc_feature
<222> LOCATION: (832)..(832)

<223> OTHER INFORMATION: n is a, c, g, or t

<400> SEQUENCE: 3
gcggcntann catgcagtcg agcggcagcg ggaaagtagc ttgctacttt tgccggcgag 60
cggcggacgg gtgagtaatg cctggggatc tgcccagtcg agggggataa ctactggaaa 120
cggtagctaa taccgcatac gccctacggg ggaaagcagg ggaccttcgg gccttgcgcg 180
attggatgaa cccaggtggg attagctagt tggtgaggta acggctcacc aaggcgacga 240
tccctagctg gtctgagagg atgatcagcc acactggaac tgagacacgg tccagactcc 300
tacgggaggc agcagtgggg aatattgcac aatgggggaa accctgatgc agccatgccg 360
cgtgtgtgaa gaaggccttc gggttgtaaa gcactttcag cgaggaggaa aggtcagtag 420
ctaatatctg ctggctgtga cgttactcgc agaagaagca ccggctaact ccgtgccagc 480
agccgcggta atacggaggg tgcaagcgtt aatcggaatt actgggcgta aagcgcacgc 540
aggcggttgg ataagttaga tgtgaaagcc ccgggctcaa cctgggaatt gcatttaaaa 600
ctgtccagct agagtcttgt agaggggggt agaattccag gtgnngcggt ggaaatgcgt 660
agagcnctgg agnnnnccgg tggncgaagn nnggccccct ggannnagac tgacgctcag 720
gtgcgaaagc gtggggagca aacaggatta gataccctgg tagtccacgc cgtaaacgat 780
gtcgatttgg gaggctgtgt ccttgagacn nngccttccg ggagcctaac gncgttaaat 840
tcgacccgcc c 851

<210> SEQ ID NO 4
<211> LENGTH: 892
<212> TYPE: DNA
<213> ORGANISM: Artificial Sequence
<220> FEATURE:
<223> OTHER INFORMATION: Br1-1-1-27F_E01.ab1
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (674)..(680)
<223> OTHER INFORMATION: n is a, c, g, or t
<220> FEATURE:
<221> NAME/KEY: misc_feature
<222> LOCATION: (692)..(693)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (804)..(805)
<223> OTHER INFORMATION: n is a, c, g, or t
<220> FEATURE:
<221> NAME/KEY: misc_feature
<222> LOCATION: (810)..(811)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (817)..(823)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (844)..(845)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (863)..(865)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (882)..(884)
<223> OTHER INFORMATION: n is a, c, g, or t

<400> SEQUENCE: 4
cgnngntncn ntgcaagtcg agcggcagcg ggaaagtagc ttgctacttt tgccggcgag 60
cggcggacgg gtgagtaatg cctggggatc tgcccagtcg agggggataa ctactggaaa 120
cggtagctaa taccgcatac gccctacggg ggaaagcagg ggaccttcgg gccttgcgcg 180
attggatgaa cccaggtggg attagctagt tggtgaggta acggctcacc aaggcgacga 240
tccctagctg gtctgagagg atgatcagcc acactggaac tgagacacgg tccagactcc 300
tacgggaggc agcagtgggg aatattgcac aatgggggaa accctgatgc agccatgccg 360
cgtgtgtgaa gaaggccttc gggttgtaaa gcactttcag cgaggaggaa aggtcagtag 420
ctaatatctg ctggctgtga cgttactcgc agaagaagca ccggctaact ccgtgccagc 480
agccgcggta atacggaggg tgcaagcgtt aatcggaatt actgggcgta aagcgcacgc 540
aggcggttgg ataagttaga tgtgaaagcc ccgggctcaa cctgggaatt gcatttaaaa 600
ctgtccagct agagtcttgt agaggggggt agaattccag gtgtagcggt gaaacgcgta 660
gagatctgga ggannnnnnn ggggagggcg gnncncntgg acaaagactg acgctcngcg 720
cgaaagcgtg gggangcaaa caggattaga taccctggta gtccacgccg taaacgatgt 780
cgatttggaa ggctgngtcc ttgnnaacgn ngacntnnnn nnnggagcta cgcntaaatc 840
gacnnctggg gngtacggcc gcnnnttaaa actcaaatna annnacgggg gc 892

<210> SEQ ID NO 5
<211> LENGTH: 815
<212> TYPE: DNA
<213> ORGANISM: Artificial Sequence
<220> FEATURE:
<223> OTHER INFORMATION: Br1-1-13-27F_F01.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (712)..(715)
<223> OTHER INFORMATION: n is a, c, g, or t
<220> FEATURE:
<221> NAME/KEY: misc_feature
<222> LOCATION: (796)..(797)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t

<400> SEQUENCE: 5

| | | | | | | |
|---|---|---|---|---|---|---|
| tgcnagtcga | gcggcagcgg | gaaagtagct | tgctactttt | gccggcgagc | ggcggacggg | 60 |
| tgagtaatgc | ctggggatct | gcccagtcga | gggggataac | tactggaaac | ggtagctaat | 120 |
| accgcatacg | ccctacgggg | gaaagcaggg | gaccttcggg | ccttgcgcga | ttggatgaac | 180 |
| ccaggtggga | ttagctagtt | ggtgaggtaa | cggctcacca | aggcgacgat | ccctagctgg | 240 |
| tctgagagga | tgatcagcca | cactggaact | gagacacggt | ccagactcct | acgggaggca | 300 |
| gcagtgggga | atattgcaca | atgggggaaa | ccctgatgca | gccatgccgc | gtgtgtgaag | 360 |
| aaggccttcg | ggttgtaaag | cactttcagc | gaggaggaaa | ggtcagtagc | taatatctgc | 420 |
| tggctgtgac | gttactcgca | gaagaagcac | cggctaactc | cgtgccagca | gccgcggtaa | 480 |
| tacggagggt | gcaagcgtta | atcggaatta | ctgggcgtaa | agcgcacgca | ggcggttgga | 540 |
| taagttagat | gtgaaagccc | cgggctcaac | ctgggaattg | catttaaaac | tgtccagcta | 600 |
| gagtcttgta | gaggggggta | gaattccagg | tgtagcggtg | aaatgcgtag | agatctggag | 660 |
| gaataccggt | ggcgaangcg | gccccctgga | caaagactga | cgctcangtg | cnnnngcgtg | 720 |
| gggagcaaac | aggattagat | accctggtag | tccacgccgt | aaacgatgtc | gatttggagg | 780 |
| ctgtgtcctt | gagacnnggn | ttccngnanc | taacg | | | 815 |

<210> SEQ ID NO 6
<211> LENGTH: 824
<212> TYPE: DNA
<213> ORGANISM: Artificial Sequence

```
<220> FEATURE:
<223> OTHER INFORMATION: Br1-1-14-27F_F02.ab1
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (700)..(710)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (806)..(807)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t

<400> SEQUENCE: 6

tgcaagtcga gcggcagcgg gaaagtagct tgctactttt gccggcgagc ggcggacggg     60

tgagtaatgc ctggggatct gcccagtcga gggggataac tactggaaac ggtagctaat    120

accgcatacg ccctacgggg gaaagcaggg gaccttcggg ccttgcgcga ttggatgaac    180

ccaggtggga ttagctagtt ggtgaggtaa cggctcacca aggcgacgat ccctagctgg    240

tctgagagga tgatcagcca cactggaact gagacacggt ccagactcct acgggaggca    300

gcagtgggga atattgcaca atgggggaaa ccctgatgca gccatgccgc gtgtgtgaag    360

aaggccttcg ggttgtaaag cactttcagc gaggaggaaa ggtcagtagc taatatctgc    420

tggctgtgac gttactcgca gaagaagcac cggctaactc cgtgccagca gccgcggtaa    480

tacggagggt gcaagcgtta atcggaatta ctgggcgtaa agcgcacgca ggcggttgga    540

taagttagat gtgaaagccc cgggctcaac ctgggaattg catttaaaac tgtccagcta    600

gagtcttgta gaggggggta gaattccagg tgtagcggtg aaatgcgtag agatctggag    660

gaataccggt ggcgaangcg gccccctgga caaagactgn nnnnnnnnnn gcgaaagcgt    720

ggggagcaaa caggattaga taccctggta gtccacgccg taaacgatgt cgatttggag    780

nctgtgtcct tganacgtgg cttccnnanc taacgcgttn aatc                     824


<210> SEQ ID NO 7
<211> LENGTH: 780
<212> TYPE: DNA
<213> ORGANISM: Artificial Sequence
<220> FEATURE:
<223> OTHER INFORMATION: Br1-1-15-27F_F03.ab1
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (676)..(678)
```

-continued

<223> OTHER INFORMATION: n is a, c, g, or t
<220> FEATURE:
<221> NAME/KEY: misc_feature
<222> LOCATION: (690)..(698)
<223> OTHER INFORMATION: n is a, c, g, or t
<220> FEATURE:
<221> NAME/KEY: misc_feature
<222> LOCATION: (700)..(702)
<223> OTHER INFORMATION: n is a, c, g, or t
<220> FEATURE:
<221> NAME/KEY: misc_feature
<222> LOCATION: (704)..(708)
<223> OTHER INFORMATION: n is a, c, g, or t
<220> FEATURE:
<221> NAME/KEY: misc_feature
<222> LOCATION: (712)..(719)
<223> OTHER INFORMATION: n is a, c, g, or t
<220> FEATURE:
<221> NAME/KEY: misc_feature
<222> LOCATION: (723)..(734)
<223> OTHER INFORMATION: n is a, c, g, or t
<220> FEATURE:
<221> NAME/KEY: misc_feature
<222> LOCATION: (736)..(744)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (751)..(752)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t

<400> SEQUENCE: 7
tgcangtcga gcggcagcgg gaaagcagct tgctactttt gccggcgagc ggcggacggg 60
tgagtaatgc ctggggatct gcccagtcga gggggataac tactggaaac ggtagctaat 120
accgcatacg ccctacgggg gaaagcaggg gaccttcggg ccttgcgcga ttggatgaac 180
ccaggtggga ttagctagtt ggtgaggtaa cggctcacca aggcgacgat ccctagctgg 240
tctgagagga tgatcagcca cactggaact gagacacggt ccagactcct acgggaggca 300
gcagtgggga atattgcaca atgggggaaa ccctgatgca gccatgccgc gtgtgtgaag 360
aaggccttcg ggttgtaaag cactttcagc gaggaggaaa ggtcagtagc taatatctgc 420
tggctgtgac gttactcgca gaagaagcac cggctaactc cgtgccagca gccgcggtaa 480
tacggagggt gcaagcgtta atcggaatta ctgggcgtaa agcgcacgca ggcggttgga 540
taagttagat gtgaaagccc cgggctcaac ctgggaattg catttaaaac tgtccagcta 600
gagtcttgta gagggggta gaattccagg tgtagcggtg aaatgcgtag agatctggan 660
gaataccggt ggcgannngg ccccctggan nnnnnnnngn nncnnnnngt gnnnnnnnng 720
ggnnnnnnnn nnnngnnnnn nnnncccngg nnantccacg ccgtaaacga tgtcnatttg 780

<210> SEQ ID NO 8
<211> LENGTH: 875
<212> TYPE: DNA
<213> ORGANISM: Artificial Sequence
<220> FEATURE:
<223> OTHER INFORMATION: Br1-1-16-27F_F04.ab1
<220> FEATURE:
<221> NAME/KEY: misc_feature -continued
<222> LOCATION: (3)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (672)..(676)
<223> OTHER INFORMATION: n is a, c, g, or t
<220> FEATURE:
<221> NAME/KEY: misc_feature
<222> LOCATION: (679)..(681)
<223> OTHER INFORMATION: n is a, c, g, or t
<220> FEATURE:
<221> NAME/KEY: misc_feature
<222> LOCATION: (686)..(687)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (693)..(699)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (715)..(716)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (739)..(745)
<223> OTHER INFORMATION: n is a, c, g, or t
<220> FEATURE:
<221> NAME/KEY: misc_feature
<222> LOCATION: (750)..(752)
<223> OTHER INFORMATION: n is a, c, g, or t
<220> FEATURE:
<221> NAME/KEY: misc_feature
<222> LOCATION: (754)..(761)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (778)..(779)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:

<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (816)..(817)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (850)..(851)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (867)..(868)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t

<400> SEQUENCE: 8
ctnnnntgcn agtcgagcgg cagcgggaaa gtagcttgct acttttgccg gcgagcggcg 60
gacgggtgag taatgcctgg ggatctgccc agtcgagggg gataactact ggaaacggta 120
gctaataccg catacgccct acgggggaaa gcaggggacc ttcgggcctt gcgcgattgg 180
atgaacccag gtgggattag ctagttggtg aggtaacggc tcaccaaggc gacgatccct 240
agctggtctg agaggatgat cagccacact ggaactgaga cacggtccag actcctacgg 300
gaggcagcag tggggaatat tgcacaatgg gggaaaccct gatgcagcca tgccgcgtgt 360
gtgaagaagg ccttcgggtt gtaaagcact ttcagcgagg aggaaaggtc agtagctaat 420
atctgctggc tgtgacgtta ctcgcagaag aagcaccggc taactccgtg ccagcagccg 480
cggtaatacg gagggtgcaa gcgttaatcg gaattactgg gcgtaaagcg cacgcaggcg 540
gttggataag ttagatgtga aagccccggg ctcaacctgg gaattgcatt taaaactgtc 600
cagctagagt cttgtagagg ggggtagaat tccaggtgta gcggtgaaat gcgtanagat 660
ctggaggata cnnnnnggnn nagagnngnc ccnnnnnnna aaanactgac gntcnntgcg 720
aaagcgtgng ggagcaaann nnnnntaaan nncnnnnnnn ncccnccccn aaaanaanna 780
tgtcnatttn ggaggctgtg tccttganac gnggcnntcc gggagctaac gncgttaaat 840
cgaccgcccn nggggnagta cgggccnnca nggnt 875

<210> SEQ ID NO 9
<211> LENGTH: 843
<212> TYPE: DNA
<213> ORGANISM: Artificial Sequence
<220> FEATURE:
<223> OTHER INFORMATION: Br1-1-17-27F_F05.ab1

<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (689)..(708)
<223> OTHER INFORMATION: n is a, c, g, or t
<220> FEATURE:
<221> NAME/KEY: misc_feature
<222> LOCATION: (710)..(715)
<223> OTHER INFORMATION: n is a, c, g, or t
<220> FEATURE:
<221> NAME/KEY: misc_feature
<222> LOCATION: (718)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (728)..(733)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (798)..(799)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (805)..(814)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (826)..(827)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t

<400> SEQUENCE: 9

-continued

```
tgcaagtcga gcggcagcgg gaaagtagct tgctactttt gccggcgagc ggcggacggg     60

tgagtaatgc ctggggatct gcccagtcga gggggataac tactggaaac ggtagctaat    120

accgcatacg ccctacgggg gaaagcaggg gaccttcggg ccttgcgcga ttggatgaac    180

ccaggtggga ttagctagtt ggtgaggtaa cggctcacca aggcgacgat ccctagctgg    240

tctgagagga tgatcagcca cactggaact gagacacggt ccagactcct acgggaggca    300

gcggtgggga atattgcaca atgggggaaa ccctgatgca gccatgccgc gtgtgtgaag    360

aaggccttcg ggttgtaaag cactttcagc gaggaggaaa ggtcagtagc tattatctgc    420

tggctgtgac gttactcgca gaagaagcac cggctaactc cgtgccagca gccgcggtaa    480

tacggagggt gcaagcgtta atcggaatta ctgggcgtaa agcgcacgca ggcggttgga    540

taagttagat gtgaaagccc cgggctcaac ctgggaattg catttaaaac tgtccagcta    600

gagtcttgta gaggggggta gaattccagg tgtagcggtg aaatgcgtag agatctggag    660

gaataccggt ggcgaagcgg ncccctggnn nnnnnnnnnn nnnnnnnngn nnnnnaannn    720

nnngnggnnn nnncaaacag gattagatac ccngggtagt ccacgccgta aacgatgtcn    780

atttngangn tgtgtccnng anacnnnnnn nnnnnanctaa cgcgtnnaat cgacngncng    840

ggg                                                                  843


<210> SEQ ID NO 10
<211> LENGTH: 774
<212> TYPE: DNA
<213> ORGANISM: Artificial Sequence
<220> FEATURE:
<223> OTHER INFORMATION: Br1-1-18-27F_F06.ab1
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (689)..(692)
<223> OTHER INFORMATION: n is a, c, g, or t
<220> FEATURE:
<221> NAME/KEY: misc_feature
<222> LOCATION: (695)..(697)
<223> OTHER INFORMATION: n is a, c, g, or t
<220> FEATURE:
<221> NAME/KEY: misc_feature
<222> LOCATION: (706)..(708)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (761)..(763)
<223> OTHER INFORMATION: n is a, c, g, or t

<400> SEQUENCE: 10

tgcaagtcga gcggcagcgg gaaagtagct tgctactttt gccggcgagc ggcggacggg     60

tgagtaatgc ctggggatct gcccagtcga gggggataac tactggaaac ggtagctaat    120

accgcatacg ccctacgggg gaaagcaggg gaccttcggg ccttgcgcga ttggatgaac    180

ccaggtggga ttagctagtt ggtgaggtaa cggctcacca aggcgacgat ccctagctgg    240

tctgagagga tgatcagcca cactggaact gagacacggt ccagactcct acgggaggca    300

gcagtgggga atattgcaca atgggggaaa ccctgatgca gccatgccgc gtgtgtgaag    360
```

```
aaggccttcg ggttgtaaag cactttcagc gaggaggaaa ggtcagtagc taatatctgc    420

tggctgtgac gttactcgca gaagaagcac cggctaactc cgtgccagca gccgcggtaa    480

tacggagggt gcaagcgttg atcggaatta ctgggcgtaa agcgcacgca ggcggttgga    540

taagttagat gtgaaagccc cgggctcaac ctgggaattg catttaaaac tgtccagcta    600

gagtcttgta gagggggggta gaattccagg tgtagcggtg aaatgcgtag agatctggag    660

gaataccggt ggcgaangcg gccccctgnn nnaannntga cgctcnnntg cgaaagcgtg    720

gggagcaaac ngnattagat accccggtag tccgcgccgt nnngatgtcg attt          774
```

<210> SEQ ID NO 11
<211> LENGTH: 790
<212> TYPE: DNA
<213> ORGANISM: Artificial Sequence
<220> FEATURE:
<223> OTHER INFORMATION: Br1-1-19-27F_F07.ab1
<220> FEATURE:
<221> NAME/KEY: misc_feature
<222> LOCATION: (672)..(677)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (692)..(693)
<223> OTHER INFORMATION: n is a, c, g, or t
<220> FEATURE:
<221> NAME/KEY: misc_feature
<222> LOCATION: (707)..(713)
<223> OTHER INFORMATION: n is a, c, g, or t
<220> FEATURE:
<221> NAME/KEY: misc_feature
<222> LOCATION: (731)..(732)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t

<400> SEQUENCE: 11

```
tgcaagtcga gcggcagcgg gaaagtagct tgctactttt gccggcgagc ggcggacggg     60

tgagtaatgc ctggggatct gcccagtcga gggggataac tactggaaac ggtagctaat    120

accgcatacg ccctacgggg gaaagcaggg gaccttcggg ccttgcgcga ttggatgaac    180

ccaggtggga ttagctagtt ggtgaggtaa cggctcacca aggcgacgat ccctagctgg    240

tctgagagga tgatcagcca cactggaact gagacacggt ccagactcct acgggaggca    300
```

-continued

```
gcagtgggga atattgcaca atgggggaaa ccctgatgca gccatgccgc gtgtgtgaag    360

aaggccttcg ggttgtaaag cactttcagc gaggaggaaa ggtcagtagc taatatctgc    420

tggctgtgac gttactcgca gaagaagcac cggctaactc cgtgccagca gccgcggtaa    480

tacggtgggt gcaagcgtta atcggaatta ctgggcgtaa agcgcacgca ggcggttgga    540

taagttagat gtgaaagccc cgggctcaac ctgggaattg catttaaaac tgtccagcta    600

gagtcttgta gaggggggta gaattccagg tgtagcggtg aaatgcgtag agatctggag    660

gaataccggt gnnnnnngng gcccccnggg annaagactg acgctcnnnn nnnaaagcgt    720

ggggagcaaa nnggattaga taccctggna gtccacgccg taaacgangt cgatttngna    780

ngctgtgtcc                                                            790
```

```
<210> SEQ ID NO 12
<211> LENGTH: 787
<212> TYPE: DNA
<213> ORGANISM: Artificial Sequence
<220> FEATURE:
<223> OTHER INFORMATION: Br1-1-20-27F_F08.ab1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (706)..(707)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (731)..(734)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (747)..(748)
<223> OTHER INFORMATION: n is a, c, g, or t
<220> FEATURE:
<221> NAME/KEY: misc_feature
<222> LOCATION: (762)..(763)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (775)..(776)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t

<400> SEQUENCE: 12
```

```
tgnaagtcga gcggcagcgg gaaagtagct tgctactttt gccggcgagc ggcggacggg     60

tgagtaatgc ctggggatct gcccagtcga gggggataac tactggaaac ggtagctaat    120

accgcatacg ccctacgggg gaaagcaggg gaccttcggg ccttgcgcga ttggatgaac    180

ccaggtggga ttagctagtt ggtgaggtaa cggctcacca aggcgacgat ccctagctgg    240

tctgagagga tgatcagcca cactggaact gagacacggt ccagactcct acgggaggca    300

gcagtgggga atattgcaca atgggggaaa ccctgatgca gccatgccgc gtgtgtgaag    360

aaggccttcg ggttgtaaag cactttcagc gaggaggaaa ggtcagtagc taatatctgc    420

tggctgtgac gttactcgca gaagaagcac cggctaactc cgtgccagca gccgcggtaa    480

tacggagggt gcaagcgtta atcggaatta ctgggcgtaa agcgcacgca ggcggttgga    540

taagttagat gtgaaagccc cgggctcaac ctgggaattg catttaaaac tgtccagcta    600

gagtcttgta gagggggta gaattccagg tgtagcggtg aaatgcgtag agatctggag    660

gaataccggt ggcgaangcg gccccctgga caaagactga cgctcnngtg cgaaagcgtg    720

gggagnaaac nnnnttanat accctgnnag tccacgccgt anngatgtcn atttnnangc    780

ngtgncc                                                               787
```

```
<210> SEQ ID NO 13
<211> LENGTH: 823
<212> TYPE: DNA
<213> ORGANISM: Artificial Sequence
<220> FEATURE:
<223> OTHER INFORMATION: Br1-1-22-27F_F10.ab1
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (795)..(796)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (802)..(802)
```

-continued

<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (806)..(806)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t

<400> SEQUENCE: 13

```
tgcaagtcga gcggcagcgg gaaagtagct tgctactttt gccggcgagc ggcggacggg     60

tgagtaatgc ctggggatct gcccagtcga gggggataac tactggaaac ggtagctaat    120

accgcatacg ccctacgggg gaaagcaggg gaccttcggg ccttgcgcga ttggatgaac    180

ccaggtggga ttagctagtt ggtgaggtaa cggctcacca aggcgacgat ccctagctgg    240

tctgagagga tgatcagcca cactggaact gagacacggt ccagactcct acgggaggca    300

gcagtgggga atattgcaca atgggggaaa ccctgatgca gccatgccgc gtgtgtgaag    360

aaggccttcg ggttgtaaag cactttcagc gaggaggaaa ggtcagtagc taatatctgc    420

tggctgtgac gttactcgca gaagaagcac cggctaactc cgtgccagca gccgcggtaa    480

tacggagggt gcaagcgtta atcggaatta ctgggcgtaa agcgcacgca ggcggttgga    540

taagttagat gtgaaagccc cgggctcaac ctgggaattg catttaaaac tgtccagcta    600

gagtcttgta gaggggggta gaattccagg tgtagcggtg aaatgcgtag agatctggag    660

gaataccggt ggcgaangcg gccccctgga caaagactga ncnctcnnng cgaaagcgtg    720

gggagcaaac aggattagat accctggtag tccacgccgt ancgatgtcg atttggangc    780

tgtgnccttg anacnnggnt tncngnanct aacgcgttna atc                      823
```

<210> SEQ ID NO 14
<211> LENGTH: 870
<212> TYPE: DNA
<213> ORGANISM: Artificial Sequence
<220> FEATURE:
<223> OTHER INFORMATION: Br1-1-2-27F_E02.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (647)..(648)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (652)..(654)
<223> OTHER INFORMATION: n is a, c, g, or t
<220> FEATURE:
<221> NAME/KEY: misc_feature
<222> LOCATION: (656)..(658)
<223> OTHER INFORMATION: n is a, c, g, or t
<220> FEATURE:
<221> NAME/KEY: misc_feature
<222> LOCATION: (660)..(661)
<223> OTHER INFORMATION: n is a, c, g, or t
<220> FEATURE:
<221> NAME/KEY: misc_feature
<222> LOCATION: (663)..(671)
<223> OTHER INFORMATION: n is a, c, g, or t
<220> FEATURE:
<221> NAME/KEY: misc_feature
<222> LOCATION: (673)..(679)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (684)..(686)
<223> OTHER INFORMATION: n is a, c, g, or t
<220> FEATURE:
<221> NAME/KEY: misc_feature
<222> LOCATION: (688)..(691)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (736)..(739)
<223> OTHER INFORMATION: n is a, c, g, or t
<220> FEATURE:
<221> NAME/KEY: misc_feature
<222> LOCATION: (741)..(742)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (753)..(754)
<223> OTHER INFORMATION: n is a, c, g, or t
<220> FEATURE:
<221> NAME/KEY: misc_feature
<222> LOCATION: (764)..(765)
<223> OTHER INFORMATION: n is a, c, g, or t
<220> FEATURE:
<221> NAME/KEY: misc_feature
<222> LOCATION: (769)..(771)
<223> OTHER INFORMATION: n is a, c, g, or t
<220> FEATURE:
<221> NAME/KEY: misc_feature
<222> LOCATION: (775)..(776)
<223> OTHER INFORMATION: n is a, c, g, or t
<220> FEATURE:
<221> NAME/KEY: misc_feature
<222> LOCATION: (789)..(790)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (804)..(804)

<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (823)..(823)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (832)..(835)
<223> OTHER INFORMATION: n is a, c, g, or t
<220> FEATURE:
<221> NAME/KEY: misc_feature
<222> LOCATION: (841)..(842)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (858)..(859)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (865)..(866)
<223> OTHER INFORMATION: n is a, c, g, or t

<400> SEQUENCE: 14
tacnntgcaa gtcgagcggc agcgggaaag tagcttgcta cttttgccgg cgagcggcgg 60
acgggtgagt aatgcctggg gatctgccca gtcgaggggg ataactactg gaaacggtag 120
ctaataccgc atacgcccta cgggggaaag caggggacct tcgggccttg cgcgattgga 180
tgaacccagg tgggattagc tagttggtga ggtaacggct caccaaggcg acgatcccta 240
gctggtctga gaggatgatc agccacactg gaactgagac acggtccaga ctcctacggg 300
aggcagcagt ggggaatatt gcacaatggg ggaaaccctg atgcagccat gccgcgtgtg 360
tgaagaaggc cttcgggttg taaagcactt tcagcgagga ggaaaggtca gtagctaata 420
tctgctggct gtgacgttac tcgcagaaga agcaccggct aactccgtgc cagcagccgc 480
ggtaatacgg agggtgcaag cgttaatcgg aattactggg cgtaaagcgc acgcaggcgg 540
ttggataagt tagatgtgaa agccccgggc tcaacctggg aattgcattt aaaactgtcc 600
agctagagtc ttgtagaggg gggtagaatt ccaggtgtag cggtganntn annnannngn 660
ngnnnnnnnn nannnnnnna naannntnnn nanctgacgc tcagtgcgaa agcgtgggga 720
gcaacngatn ancgtnnnnc nnacagcatn ganngtcctt aaannggtnn nggannaccg 780
tttaaattnn ccgccnggga ananggnccc gagngntaaa agnttcaaan tnnnntatgg 840
nnagtntgga ncgggggnnc cgncnncaaa 870

<210> SEQ ID NO 15
<211> LENGTH: 789
<212> TYPE: DNA
<213> ORGANISM: Artificial Sequence
<220> FEATURE:
<223> OTHER INFORMATION: Br1-1-23-27F_F11.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (706)..(708)
<223> OTHER INFORMATION: n is a, c, g, or t
<220> FEATURE:
<221> NAME/KEY: misc_feature
<222> LOCATION: (711)..(712)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (784)..(786)
<223> OTHER INFORMATION: n is a, c, g, or t

<400> SEQUENCE: 15
tgcnagtcga gcggcagcgg gaaagtagct tgctactttt gccggcgagc ggcggacggg 60
tgagtaatgc ctggggatct gcccagtcga gggggataac tactggaaac ggtagctaat 120
accgcatacg ccctacgggg gaaagcaggg gaccttcggg ccttgcgcga ttggatgaac 180
ccaggtggga ttagctagtt ggtgaggtaa cggctcacca aggcgacgat ccctagctgg 240
tctgagagga tgatcagcca cactggaact gagacacggt ccagactcct acgggaggca 300
gcagtgggga atattgcaca atgggggaaa ccctgatgca gccatgccgc gtgtgtgaag 360
aaggccttcg ggttgtaaag cactttcagc gaggaggaaa ggtcagtagc taatatctgc 420
tggctgtgac gttactcgca gaagaagcac cggctaactc cgtgccagca gccgcggtaa 480
tacggagggt gcaagcgtta atcggaatta ctgggcgtaa agcgcacgca ggcggttgga 540
taagttagat gtgaaagccc cgggctcaac ctgggaattg catttaaaac tgtccagcta 600
gagtcttgta gaggggggta gaattccagg tgtagcggtg aaatgcgtag agatctggag 660
gaataccggt ggcgaangcg gccccctgga caaagactga cgctcnnngc nnaaagcgtg 720
gggagcaaac ngnattagat accctggtag tccacgccgt aaacnatgtc gatttngagn 780 ctgnnncct 789

<210> SEQ ID NO 16
<211> LENGTH: 777
<212> TYPE: DNA
<213> ORGANISM: Artificial Sequence
<220> FEATURE:
<223> OTHER INFORMATION: Br1-1-24-27F_F12.ab1
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (671)..(672)
<223> OTHER INFORMATION: n is a, c, g, or t
<220> FEATURE:
<221> NAME/KEY: misc_feature
<222> LOCATION: (700)..(702)
<223> OTHER INFORMATION: n is a, c, g, or t
<220> FEATURE:
<221> NAME/KEY: misc_feature
<222> LOCATION: (714)..(718)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (727)..(728)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (751)..(752)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t

<400> SEQUENCE: 16
tcgagcggca gcgggaaagt agcttgctac ttttgccggc gagcggcgga cgggtgagta 60
atgcctgggg atctgcccag tcgaggggga taactactgg aaacggtagc taataccgca 120

```
tacgccctac gggggaaagc aggggacctt cgggccttgc gcgattggat gaacccaggt    180

gggattagct agttggtgag gtaacggctc accaaggcga cgatccctag ctggtctgag    240

aggatgatca gccacactgg aactgagaca cggtccagac tcctacggga ggcagcagtg    300

gggaatattg cacaatgggg gaaaccctga tgcagccatg ccgcgtgtgt gaagaaggcc    360

ttcgggttgt aaagcacttt cagcgaggag gaaaggtcag tagctaatat ctgctggctg    420

tgacgttact cgcagaagaa gcaccggcta actccgtgcc agcagccgcg gtaatacgga    480

gggtgcaagc gttaatcgga attactgggc gtaaagcgca cgcaggcggt tggataagtt    540

agatgtgaaa gccccgggct caacctggga attgcattta aaactgtcca gctagagtct    600

tgtananggg ggtagaantc caggtgtagc ggtgaaatgc gtanagatct ggaggaatac    660

cggtggcgaa nncggccccc tggacaaaga ctgacgctcn nngcgaaagc gtgnnnnnca    720

aacangnnta gataccctgg tagtccncnc nntaaacgan gtcnatttng naggctg       777
```

<210> SEQ ID NO 17
<211> LENGTH: 887
<212> TYPE: DNA
<213> ORGANISM: Artificial Sequence
<220> FEATURE:
<223> OTHER INFORMATION: Br1-1-3-27F_E03.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (594)..(597)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (605)..(607)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (611)..(613)
<223> OTHER INFORMATION: n is a, c, g, or t
<220> FEATURE:

<221> NAME/KEY: misc_feature
<222> LOCATION: (615)..(618)
<223> OTHER INFORMATION: n is a, c, g, or t
<220> FEATURE:
<221> NAME/KEY: misc_feature
<222> LOCATION: (620)..(623)
<223> OTHER INFORMATION: n is a, c, g, or t
<220> FEATURE:
<221> NAME/KEY: misc_feature
<222> LOCATION: (703)..(704)
<223> OTHER INFORMATION: n is a, c, g, or t
<220> FEATURE:
<221> NAME/KEY: misc_feature
<222> LOCATION: (708)..(712)
<223> OTHER INFORMATION: n is a, c, g, or t
<220> FEATURE:
<221> NAME/KEY: misc_feature
<222> LOCATION: (715)..(719)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (730)..(731)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t

<400> SEQUENCE: 17

```
gntnnncntg caagtcgagc ggcagcggga aagtagcttg ctacttttgc cggcgagcgg     60

cggacgggtg agtaatgcct ggggatctgc ccagtcgagg gggataacta ctggaaacgg    120

tagctaatac cgcatacgcc ctacggggga aagcagggga ccttcgggcc ttgcgcgatt    180

ggatgaaccc aggtgggatt agctagttgg tgaggtaacg gctcaccaag gcgacgatcc    240

ctagctggtc tgagaggatg atcagccaca ctggaactga gacacggtcc agactcctac    300

gggaggcagc agtggggaat attgcacaat gggggaaacc ctgatgcagc catgccgcgt    360

gtgtgaagaa ggccttcggg ttgtaaagca ctttcagcga ggaggaaagg tcagtagcta    420

atatctgctg gctgtgacgt tactcgcaga agaagcaccg gctaactccg tgccagcagc    480

cgcggtaata cggagggtgc aagcgttaat cggaattact gggcgtaaag cgcacgcagg    540

cggttggata agttagatgt gaaagccccg ggctcaacct gggtntnanc tgtnnnnang    600

tnggnnngnt nnngnnnnan nnnggtagcg gtgaaatgcg tagagatctg gaggaatacc    660

ggtggcgaag gcggcccccct ggacaaagac tgacgctcag tgnnaaannn nnggnnnnna    720

ncaagacagn nattagatac cctggtagtc caccgccgta aacgatgtcg attatgntag    780

gatgctgtgt ccttgagacg tggcttccgg agctaacgcg ttaaatcgac gcctggggag    840

tacggccgca aggttaaaac tcaaatgaat tgacgggggc cccgcca                  887
```

<210> SEQ ID NO 18
<211> LENGTH: 882
<212> TYPE: DNA
<213> ORGANISM: Artificial Sequence
<220> FEATURE:
<223> OTHER INFORMATION: Br1-1-4-27F_E04.ab1
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

```
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (644)..(647)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (810)..(812)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t
<220> FEATURE:
<221> NAME/KEY: misc_feature
<222> LOCATION: (849)..(851)
<223> OTHER INFORMATION: n is a, c, g, or t
<220> FEATURE:
<221> NAME/KEY: misc_feature
<222> LOCATION: (854)..(855)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t

<400> SEQUENCE: 18

tanncntgca agtcgagcgg cagcgggaaa gtagcttgct acttttgccg gcgagcggcg     60

gacgggtgag taatgcctgg ggatctgccc agtcgagggg gataactact ggaaacggta    120

gctaataccg catacgccct acgggggaaa gcaggggacc ttcgggcctt gcgcgattgg    180

atgaacccag gtgggattag ctagttggtg aggtaacggc tcaccaaggc gacgatccct    240

agctggtctg agaggatgat cagccacact ggaactgaga cacggtccag actcctacgg    300

gaggcagcag tggggaatat tgcacaatgg gggaaaccct gatgcagcca tgccgcgtgt    360

gtgaagaagg ccttcgggtt gtaaagcact ttcagcgagg aggaaaggtc agtagctaat    420

atctgctgac tgtgacgtta ctcgcagaag aagcaccggc taactccgtg ccagcagccg    480

cggtaatacg gagggtgcaa gcgttaatcg gaattactgg gcgtaaagcg cacgcaggcg    540

gttggataag ttagatgtga aagccccggg ctcaacctgg gaattgcttt taaaactgtc    600

tngctaanag tcttgtagag gggggtagaa ttccaggtgt agcnnnngaa atgcgtagag    660

atctggagga ataccggtgg cgaaggcggc ccctggnaca aaaactgacg ctcangtgcg    720

aaaaaagcgt ggggagcaaa caggattaga taccctggna gtccacgccg taaacgatgt    780

cgattgngga ggctgtgtcc ttgagacgtn nntccggagc taacgcgtta atcgacgcng    840
```

-continued gggagtacnn ncannaaact caaatgaang acgggggccc gc 882

<210> SEQ ID NO 19
<211> LENGTH: 888
<212> TYPE: DNA
<213> ORGANISM: Artificial Sequence
<220> FEATURE:
<223> OTHER INFORMATION: Br1-1-5-27F_E05.ab1
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (701)..(703)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (715)..(718)
<223> OTHER INFORMATION: n is a, c, g, or t
<220> FEATURE:
<221> NAME/KEY: misc_feature
<222> LOCATION: (721)..(722)
<223> OTHER INFORMATION: n is a, c, g, or t
<220> FEATURE:
<221> NAME/KEY: misc_feature
<222> LOCATION: (727)..(729)
<223> OTHER INFORMATION: n is a, c, g, or t
<220> FEATURE:
<221> NAME/KEY: misc_feature
<222> LOCATION: (739)..(740)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (775)..(776)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (798)..(800)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (804)..(805)
<223> OTHER INFORMATION: n is a, c, g, or t
<220> FEATURE:
<221> NAME/KEY: misc_feature
<222> LOCATION: (812)..(813)
<223> OTHER INFORMATION: n is a, c, g, or t
<220> FEATURE:
<221> NAME/KEY: misc_feature
<222> LOCATION: (816)..(819)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (828)..(830)
<223> OTHER INFORMATION: n is a, c, g, or t
<220> FEATURE:
<221> NAME/KEY: misc_feature
<222> LOCATION: (839)..(843)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (863)..(864)
<223> OTHER INFORMATION: n is a, c, g, or t
<220> FEATURE:
<221> NAME/KEY: misc_feature
<222> LOCATION: (866)..(867)
<223> OTHER INFORMATION: n is a, c, g, or t
<220> FEATURE:

<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t

<400> SEQUENCE: 19

```
gctacnntgc aagtcgagcg gcagcgggaa agtagcttgc tacttttgcc ggcgagcggc      60

ggacgggtga gtaatgcctg gggatctgcc cagtcgaggg ggataactac tggaaacggt     120

agctaatacc gcatacgccc tacgggggaa agcaggggac cttcgggcct tgcgcgattg     180

gatgaaccca ggtgggatta gctagttggt gaggtaacgg ctcaccaagg cgacgatccc     240

tagctggtct gagaggatga tcagccacac tggaactgag acacggtcca gactcctacg     300

ggaggcagca gtggggaata ttgcacaatg ggggaaaccc tgatgcagcc atgccgcgtg     360

tgtgaagaag gccttcgggt tgtaaagcac tttcagcgag gaggaaaggt cagtagctaa     420

tatctgctgg ctgtgacgtt actcgcagaa gaagcaccgg ctaactccgt gccagcagcc     480

gcggtaatac ggagggtgca agcgttaatc ggaattactg ggcgtaaagc gcacgcaggc     540

ggttggataa gttagatgtg aaagccccgg gctcaacctg ggaattgcat ttaaaactgt     600

ccagctagag tcttgtagag gggggtaaaaa tcagngggna nncgggtaaa tggctaaana     660

tcctgaagaa ttacggtggg cnaaggngcc cctggacnaa nnnanggang cttcnnnngc     720

nnaagcnnng ggggaagcnn accaggatta ngantaccct ggnagtccac gccgnnaacg     780

atngtcnatt tggagctnnn gncnnagaac gnngcnnnna gctangcnnn atcgacgcnn     840

nnntncgncn cangtaaant nannannacg gggnccncaa ancggngg                  888
```

<210> SEQ ID NO 20
<211> LENGTH: 905
<212> TYPE: DNA
<213> ORGANISM: Artificial Sequence
<220> FEATURE:
<223> OTHER INFORMATION: Br1-1-6-27F_E06.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (822)..(823)
<223> OTHER INFORMATION: n is a, c, g, or t
<220> FEATURE:
<221> NAME/KEY: misc_feature
<222> LOCATION: (840)..(842)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (893)..(893)
<223> OTHER INFORMATION: n is a, c, g, or t
<220> FEATURE:
<221> NAME/KEY: misc_feature
<222> LOCATION: (895)..(898)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t

<400> SEQUENCE: 20

```
ctacnntgca agtcgagcgg cagcgggaaa gtagcttgct acttttgccg gcgagcggcg     60

gacgggtgag taatgcctgg gaatctgccc agtcgagggg gataactact ggaaacggta    120

gctaataccg catacgccct acgggggaaa gcaggggacc ttcgggcctt gcgcgattgg    180

atgaacccag gtgggattag ctagttggtg aggtaacggc tcaccaaggc gacgatccct    240

agctggtctg agaggatgat cagccacact ggaactgaga cacggtccag actcctacgg    300

gaggcagcag tggggaatat tgcacaatgg gggaaaccct gatgcagcca tgccgcgtgt    360

gtgaagaagg ccttcgggtt gtaaagcact ttcagcgagg aggaaaggtc agtagctaat    420

atctgctggc tgtgacgtta ctcgcagaag aagcaccggc taactccgtg ccagcagccg    480

cggtaatacg gagggtgcaa gcgttaatcg gaattactgg gcgtaaagcg cacgcaggcg    540

gttggataag ttagatgtga aagccccggg ctcaacctgg gaattgcatt taaaactgtc    600

cagctagagt cttgtagagg ggggtagaat tccaggtgta gcggtgaaat gcgtagagat    660

ctggaggaat accggtggcg aaggcggccc cctggacaaa gactgacgct cangtgcgaa    720

agcgtgggga gcaaacagng attagatacc ctggtagtcc acgccgtaaa cgatgtcgat    780

ttggaggctg tgtccttgag acgtggnttc cggagctaac gnngttaaat cgaccgcctn    840

nnagtaccgg cngccaaggt taaaacctca aatgaatttg acgggggccc ggncnnnnag    900

ncggg                                                                905
```

<210> SEQ ID NO 21
<211> LENGTH: 913
<212> TYPE: DNA
<213> ORGANISM: Artificial Sequence
<220> FEATURE:
<223> OTHER INFORMATION: Br1-1-7-27F_E07.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (656)..(662)
<223> OTHER INFORMATION: n is a, c, g, or t
<220> FEATURE:
<221> NAME/KEY: misc_feature
<222> LOCATION: (666)..(668)
<223> OTHER INFORMATION: n is a, c, g, or t
<220> FEATURE:

<221> NAME/KEY: misc_feature
<222> LOCATION: (671)..(680)
<223> OTHER INFORMATION: n is a, c, g, or t
<220> FEATURE:
<221> NAME/KEY: misc_feature
<222> LOCATION: (694)..(698)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (765)..(768)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (774)..(775)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (786)..(787)
<223> OTHER INFORMATION: n is a, c, g, or t
<220> FEATURE:
<221> NAME/KEY: misc_feature
<222> LOCATION: (789)..(794)
<223> OTHER INFORMATION: n is a, c, g, or t
<220> FEATURE:
<221> NAME/KEY: misc_feature
<222> LOCATION: (796)..(799)
<223> OTHER INFORMATION: n is a, c, g, or t
<220> FEATURE:
<221> NAME/KEY: misc_feature
<222> LOCATION: (801)..(807)
<223> OTHER INFORMATION: n is a, c, g, or t
<220> FEATURE:
<221> NAME/KEY: misc_feature
<222> LOCATION: (811)..(812)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (898)..(900)
<223> OTHER INFORMATION: n is a, c, g, or t
<220> FEATURE:
<221> NAME/KEY: misc_feature
<222> LOCATION: (902)..(905)
<223> OTHER INFORMATION: n is a, c, g, or t
<220> FEATURE:
<221> NAME/KEY: misc_feature
<222> LOCATION: (908)..(910)
<223> OTHER INFORMATION: n is a, c, g, or t

<400> SEQUENCE: 21
tacnntgcaa gtcgagcggc agcgggaaag tagcttgcta cttttgccgg cgagcggcgg 60
acgggtgagt aatacctggg gatctgccca gtcgaggggg ataactactg gaaacggtag 120
ctaataccgc atacgcccta cgggggaaag caggggacct tcgggccttg cgcgattgga 180
tgaacccagg tgggattagc tagttggtga ggtaacggct caccaaggcg acgatcccta 240
gctggtctga gaggatgatc agccacactg gaactgagac acggtccaga ctcctacggg 300
aggcagcagt ggggaatatt gcacaatggg ggaaaccctg atgcagccat gccgcgtgtg 360
tgaagaaggc cttcgggttg taaagcactt tcagcgagga ggaaaggtca gtagctaata 420
tctgctggct gtgacgttac tcgcagaaga agcaccggct aactccgtgc cagcagccgc 480
ggtaatacgg agggtgcaag cgttaatcgg aattactggg cgtaaagcgc acgcaggcgg 540
ttggataagt tagatgtgaa agccccgggc tcaacctggg agttgcattt aaaactgtcc 600
agctagagtc ttgtagaggg gggtagaatt ccaggtgtag cggtgaaatg cnanannnnn 660
nngggnnntc nnnnnnnnnn gccccctggg acannnnntg acgctcaggt gcgaaagcgt 720
ggggagcaaa caggattaga taccctggta gtccncgccg taaannnnan gtcnnttngn 780
gagngnngnn nnnntnnnna nnnnnnncct nncgtnccng agctaacgcg ttaaatcgac 840
gnctggggga gtacgnccgc aaggttaaaa ctcaaatgaa tttnacgggg gcccgccnnn 900
annnnggnnn ggg 913

<210> SEQ ID NO 22
<211> LENGTH: 903
<212> TYPE: DNA
<213> ORGANISM: Artificial Sequence
<220> FEATURE:
<223> OTHER INFORMATION: Br1-1-8-27F_E08.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (597)..(600)
<223> OTHER INFORMATION: n is a, c, g, or t
<220> FEATURE:
<221> NAME/KEY: misc_feature
<222> LOCATION: (664)..(665)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (686)..(689)
<223> OTHER INFORMATION: n is a, c, g, or t
<220> FEATURE:
<221> NAME/KEY: misc_feature
<222> LOCATION: (695)..(697)
<223> OTHER INFORMATION: n is a, c, g, or t
<220> FEATURE:
<221> NAME/KEY: misc_feature
<222> LOCATION: (699)..(700)
<223> OTHER INFORMATION: n is a, c, g, or t
<220> FEATURE:

<221> NAME/KEY: misc_feature
<222> LOCATION: (718)..(719)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (750)..(751)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (770)..(771)
<223> OTHER INFORMATION: n is a, c, g, or t
<220> FEATURE:
<221> NAME/KEY: misc_feature
<222> LOCATION: (774)..(775)
<223> OTHER INFORMATION: n is a, c, g, or t
<220> FEATURE:
<221> NAME/KEY: misc_feature
<222> LOCATION: (787)..(788)
<223> OTHER INFORMATION: n is a, c, g, or t
<220> FEATURE:
<221> NAME/KEY: misc_feature
<222> LOCATION: (791)..(792)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (806)..(806)
<223> OTHER INFORMATION: n is a, c, g, or t
<220> FEATURE:
<221> NAME/KEY: misc_feature
<222> LOCATION: (812)..(813)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (817)..(818)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (822)..(823)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (852)..(853)
<223> OTHER INFORMATION: n is a, c, g, or t
<220> FEATURE:
<221> NAME/KEY: misc_feature
<222> LOCATION: (858)..(861)
<223> OTHER INFORMATION: n is a, c, g, or t
<220> FEATURE:
<221> NAME/KEY: misc_feature
<222> LOCATION: (864)..(865)
<223> OTHER INFORMATION: n is a, c, g, or t
<220> FEATURE:
<221> NAME/KEY: misc_feature
<222> LOCATION: (867)..(868)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (879)..(883)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t

<400> SEQUENCE: 22
tacnntgcaa gtcgagcggc agcgggaaag tagcttgcta cttttgccgg cgagcggcgg 60
acgggtgagt aatgcctggg gatctgccca gtcgaggggg ataactactg gaaacggtag 120
ctaataccgc atacgcccta cgggggaaag caggggacct tcgggccttg cgcgattgga 180
tgaacccagg tgggattagc tagttggtga ggtaacggct caccaaggcg acgatcccta 240
gctggtctga gaggatgatc agccacactg gaactgagac acggtccaga ctcctacggg 300
aggcagcagt ggggaatatt gcacaatggg ggaaaccctg atgcagccat gccgcgtgtg 360
tgaagaaggc cttcgggttg taaagcactt tcagcgagga ggaaaggtca gtagctaata 420
tctgctggct gtgacgttac tcgcagaaga agcaccggct aactccgtgc cagcagccgc 480
ggtaatacgg agggtgcaag cgttaatcgg aattactggg cgtaaagcgc acgcaggcgg 540
ttggataagt tagatgtgaa agccccgggc tcaacctggg aattgcattt aaaactnnnn 600
agctagagtc ttgtagaggg gggtagaatt ccaggtgtag cggtgaaatg cgtagagatc 660
tggnngggaa taccggtggc naaggnnnnc cctcnnngnn acaaaagact gacgctcnnt 720
gcgaaagcgt ggggagcaan caggnttaan naccctcgng atanctacan nccnnacaca 780
gatgtcnntt nnggaggctg gntccntgag annangnntn cnncngnagc tactcntnaa 840
tcgacgcngn gnntacgnnn nagnnanntn aatgaangnn nnngcccgca cagcgntgga 900 nca 903

<210> SEQ ID NO 23
<211> LENGTH: 899
<212> TYPE: DNA
<213> ORGANISM: Artificial Sequence
<220> FEATURE:
<223> OTHER INFORMATION: Br1-1-9-27F_E09.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (628)..(632)
<223> OTHER INFORMATION: n is a, c, g, or t
<220> FEATURE:
<221> NAME/KEY: misc_feature
<222> LOCATION: (668)..(669)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (722)..(723)
<223> OTHER INFORMATION: n is a, c, g, or t
<220> FEATURE:
<221> NAME/KEY: misc_feature
<222> LOCATION: (753)..(755)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (791)..(792)
<223> OTHER INFORMATION: n is a, c, g, or t -continued
<220> FEATURE:
<221> NAME/KEY: misc_feature
<222> LOCATION: (794)..(796)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (815)..(817)
<223> OTHER INFORMATION: n is a, c, g, or t
<220> FEATURE:
<221> NAME/KEY: misc_feature
<222> LOCATION: (819)..(821)
<223> OTHER INFORMATION: n is a, c, g, or t
<220> FEATURE:
<221> NAME/KEY: misc_feature
<222> LOCATION: (830)..(832)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (848)..(850)
<223> OTHER INFORMATION: n is a, c, g, or t
<220> FEATURE:
<221> NAME/KEY: misc_feature
<222> LOCATION: (853)..(856)
<223> OTHER INFORMATION: n is a, c, g, or t
<220> FEATURE:
<221> NAME/KEY: misc_feature
<222> LOCATION: (859)..(861)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
<222> LOCATION: (872)..(873)
<223> OTHER INFORMATION: n is a, c, g, or t
<220> FEATURE:
<221> NAME/KEY: misc_feature
<222> LOCATION: (892)..(893)
<223> OTHER INFORMATION: n is a, c, g, or t
<220> FEATURE:
<221> NAME/KEY: misc_feature
<222> LOCATION: (895)..(895)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t

<400> SEQUENCE: 23
gnttannntg cagtcgagcg gagatgaggt gcttgcacct tatcttagcg gcggacgggt 60
gagtaatgct taggaatctg ccatttagtg ggggacaaca ttccgaaagg aatgctaata 120
ccgcatacgt cgtacgggag aaagcagggg atcttcggac cttgcgctaa atgatgagcc 180
taagtcggat tagctagttg gtggggtaaa ggcctaccaa ggcgacgatc tgtagcgggt 240
ctgagaggat gatccgccac actgggactg agacacggcc cagactccta cgggaggcag 300
cagtggggaa tattggacaa tgggcggaag cctgatccag ccatgccgcg tgtgtgaaga 360
aggccttttg gttgtaaagc actttaagcg aggaggaggc tactagtact aatactactg 420
gatagtggac gttactcgca gaataagcac cggctaactc tgtgccagca gccgcggtaa 480

```
tacggagggt gcaagcgtta atcggaatta ctgggcgtaa agcgcacgca ggcggttgga    540

taagttagat gtgaaagccc cgggctcaac ctgggaattg catttaaaac tgtccagcta    600

gagtcttgta gagggggta gaattccnnn nntagcggtg aaatgcgtag agatctggag    660

gaataccnng tggcgaaggc ggccccctgg ataaanactg acgcnctcag gngcnanagc    720

gnnggtgggg gagcaaacag gattagatac ccnnngatag tccacgccgt aacnatngtc    780

natntntagg nngnnngngn tctttagaag acgtnnntnn nagctacgcn nnaatcgacc    840

gcntgggnnn tannnncann naactcaang annacggggc ccgccacagc gnngnanca     899


<210> SEQ ID NO 24
<211> LENGTH: 881
<212> TYPE: DNA
<213> ORGANISM: Artificial Sequence
<220> FEATURE:
<223> OTHER INFORMATION: FM-1-10-27F_G03.ab1
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (694)..(696)
<223> OTHER INFORMATION: n is a, c, g, or t
<220> FEATURE:
<221> NAME/KEY: misc_feature
<222> LOCATION: (698)..(704)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (758)..(762)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t
<220> FEATURE:
<221> NAME/KEY: misc_feature
<222> LOCATION: (844)..(844)
<223> OTHER INFORMATION: n is a, c, g, or t
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (857)..(858)
<223> OTHER INFORMATION: n is a, c, g, or t
<220> FEATURE:
<221> NAME/KEY: misc_feature
<222> LOCATION: (861)..(862)
<223> OTHER INFORMATION: n is a, c, g, or t

<400> SEQUENCE: 24
```

```
ggctgcctta ccntgcaagt cgaacggtaa caggtcttcg gatgctgacg agtggcgaac      60

gggtgagtaa tacatcggaa cgtgcccgat cgtgggggat aacgaagcga aagctttgct     120

aataccgcat aagatctaag gatgaaagca ggggaccgca aggccttgcg cgaacggagc     180

ggccgatggc agattaggta gttggtggga taaaagctta ccaagccgac gatctgtagc     240

tggtctgaga ggacgaccag ccacactggg actgagacac ggcccagact cctacgggag     300

gcagcagtgg ggaattttgg acaatgggcg aaagcctgat ccagccatgc cgcgtgcagg     360

atgaaggcct tcgggttgta aactgctttt gtacggaacg aaaagactct ggttaatacc     420

tggggtccat gacggtaccg taagaataag caccggctaa ctacgtgcca gcagccgcgg     480

taatacgtag ggtgcaagcg ttaatcggaa ttactgggcg taaagcgtgc gcaggcggtt     540

atataagaca gatgtgaaat ccccgggctc aacctgggaa ctgcatttgt gactgtatag     600

ctagagtacg gtagaggggg atggaattcc gcgtgtagca gtgaaatgcg tagatatgcg     660

gaggaacacc gatggcgaag gcaatcccct ggannngnnn nnnncnctca tgcacgaaag     720

cgtggggacc aacaggatta gatacccngg tagtccannn nntaaacgat gtcaactggn     780

ttgttgggtc ttcactgact cagtaacgaa gctaacgcgt gaagttgacc ncngggagt      840

acgncnncan ggttganntc nnaggaattg acgggggacc c                         881
```

<210> SEQ ID NO 25
<211> LENGTH: 893
<212> TYPE: DNA
<213> ORGANISM: Artificial Sequence
<220> FEATURE:
<223> OTHER INFORMATION: FM-1-11-27F_G04.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (657)..(660)
<223> OTHER INFORMATION: n is a, c, g, or t
<220> FEATURE:
<221> NAME/KEY: misc_feature
<222> LOCATION: (747)..(754)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:

<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t
<220> FEATURE:
<221> NAME/KEY: misc_feature
<222> LOCATION: (841)..(841)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (847)..(847)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (887)..(888)
<223> OTHER INFORMATION: n is a, c, g, or t

<400> SEQUENCE: 25

```
gccttanntg cagtcgaacg gtaacaggtc ttcggatgct gacgagtggc gaacgggtga      60

gtaatacatc ggaacgtgcc cgatcgtggg ggataacgaa gcgaaagctt tgctaatacc     120

gcataagatc taaggatgaa agcaggggac cgcaaggcct tgcgcgaacg gagcggccga     180

tggcagatta ggtagttggt gggataaaag cttaccaagc cgacgatctg tagctggtct     240

gagaggacga ccagccacac tgggactgag acacggccca gactcctacg ggaggcagca     300

gtggggaatt ttggacaatg ggcgaaagcc tgatccagcc atgccgcgtg caggatgaag     360

gccttcgggt tgtaaactgc ttttgtacgg aacgaaaaga ctctggttaa tacctggggt     420

ccatgacggt accgtaagaa taagcaccgg ctaactacgt gccagcagcc gcggtaatac     480

gtagggtgca agcgttaatc ggaattactg ggcgtaaagc gtgcgcaggc ggttatataa     540

gacagatgtg aaatccccgg gctcaacctg ggaactgcat ttgtgactgt atagctagag     600

tacggtagag gggatggaa ttccgcgtgt agcagtgaaa tgcgtagata tgcggannnn     660

acacggatgg cgaaggcaat cccctggacc tgtactgacg ctcatgcacg aaagcgtggg     720

gagcaaacag gattagatac cctggtnnnn nnnnccctaa acgangtcna ctggntngtt     780

gggtctnctc ngtgaantna gtaacgaagc taacgcgtga agttgaccgc ngggngtang     840

ngcangntga aactcaaagg aattgacggg aacccgccac aagnggnngg aat            893
```

<210> SEQ ID NO 26
<211> LENGTH: 835
<212> TYPE: DNA
<213> ORGANISM: Artificial Sequence
<220> FEATURE:
<223> OTHER INFORMATION: FM1-1-1-27F_F06.ab1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (681)..(682)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (778)..(780)
<223> OTHER INFORMATION: n is a, c, g, or t
<220> FEATURE:
<221> NAME/KEY: misc_feature
<222> LOCATION: (782)..(782)
<223> OTHER INFORMATION: n is a, c, g, or t
<220> FEATURE:
<221> NAME/KEY: misc_feature
<222> LOCATION: (792)..(793)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (814)..(818)
<223> OTHER INFORMATION: n is a, c, g, or t

<400> SEQUENCE: 26
cgntgcttac ctgcaagtcg aacggtaaca ggtcttcgga tgctgacgag tggcgaacgg 60
gtgagtaata catcggaacg tgcccgatcg tgggggataa cgaagcgaaa gctttgctaa 120
taccgcataa gatctaagga tgaaagcagg ggaccgcaag gccttgcgcg aacggagcgg 180
ccgatggcag attaggtagt tggtgggata aaagcttacc aagccgacga tctgtagctg 240
gtctgagagg acgaccagcc acactgggac tgagacacgg cccagactcc tacgggaggc 300
agcagtgggg aattttggac aatgggcgaa agcctgatcc agccatgccg cgtgcaggat 360
gaaggccttc gggttgtaaa ctgcttttgt acggaacgaa aagactctgg ttaatacctg 420
gggtccatga cggtaccgta agaataagca ccggctaact acgtgccagc agccgcggta 480
atacgtaggg tgcgagcgtt aatcggaatt actgggcgta aagcgtgcgc aggcggttat 540
ataagacaga tgtgaaatcc ccgggctcaa cctgggaact gcatttgtga ctgtatagct 600
agagtacggt agagggggat ggaattccgc gtgtagcagt gaaatgcgta gatatgcgga 660
ggaacacncg atggcgaaag nnatcccctg gacctgtact gacgctcatg cacgaaagcg 720
tggngagcaa acaggattag ataccctggt agtccacgcc cnaaacgang ncaactgnnn 780
gntgggtctt cnntgantca gtacgaagct aacnnnnnga agttgaccgc ctggg 835

<210> SEQ ID NO 27
<211> LENGTH: 899
<212> TYPE: DNA

<213> ORGANISM: Artificial Sequence
<220> FEATURE:
<223> OTHER INFORMATION: FM-1-12-27F_G05.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (657)..(658)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (714)..(717)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (850)..(851)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (857)..(858)
<223> OTHER INFORMATION: n is a, c, g, or t
<220> FEATURE:
<221> NAME/KEY: misc_feature
<222> LOCATION: (861)..(863)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
<222> LOCATION: (874)..(875)
<223> OTHER INFORMATION: n is a, c, g, or t
<220> FEATURE:
<221> NAME/KEY: misc_feature
<222> LOCATION: (879)..(883)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t

<400> SEQUENCE: 27
ttanntgcag tcgaacggta acaggtcttc ggatgctgac gagtggcgaa cgggtgagta 60
atacatcgga acgtgcccga tcgtggggga taacgaagcg aaagctttgc taataccgca 120
taagatctaa ggatgaaagc aggggaccgc aaggccttgc gcgaacggag cggccgatgg 180
cagattaggt agttggtggg ataaaagctt accaagccga cgatctgtag ctggtctgag 240
aggacgacca gccacactgg gactgagaca cggcccagac tcctacggga ggcagcagtg 300
gggaattttg gacaatgggc gaaagcctga tccagccatg ccgcgtgcag gatgaaggcc 360
ttcgggttgt aaactgcttt tgtacggaac gaaaagactc tggttaatac ctggggtcca 420
tgacggtacc gtaagaataa gcaccggcta actacgtgcc agcagccgcg gtaatacgta 480
gggtgcaagc gttaatcgga attactgggc gtaaagcgtg cgcaggcggt tatataagac 540
agatgtgaaa tccccgggct caacctggga actgcatttg tgactgtata gctagagtac 600
ggtagagggg gatggaattc cgcgtgtagc agtgaaatgc gtagatatgc ggaggannac 660
cgatgggcga aggcaatccc ctggacctgt actgacgctc atgnccgaaa gcgnnnngag 720
caaacaggat ttanataccc tggnagtcca cgccctaaac gatgtcaact ggttgttggg 780
tcttcactga ctcagtaacg aagctaacgn cgtgaagttg ancgcctggg gngnnncggg 840
ccncanggtn nananannct nnnanggant tggnngggnn nnncccgnca ccaagccgg 899

<210> SEQ ID NO 28
<211> LENGTH: 882
<212> TYPE: DNA
<213> ORGANISM: Artificial Sequence
<220> FEATURE:
<223> OTHER INFORMATION: FM1-1-2-27F_F07.ab1
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (773)..(775)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (809)..(810)

<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (828)..(829)
<223> OTHER INFORMATION: n is a, c, g, or t
<220> FEATURE:
<221> NAME/KEY: misc_feature
<222> LOCATION: (831)..(836)
<223> OTHER INFORMATION: n is a, c, g, or t
<220> FEATURE:
<221> NAME/KEY: misc_feature
<222> LOCATION: (838)..(849)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (873)..(875)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t

<400> SEQUENCE: 28

```
tgccttacct gcagtcgaac ggtaacaggt cttcggatgc tgacgagtgg cgaacgggtg      60

agtaatacat cggaacgtgc ccgatcgtgg gggataacga agcgaaagct ttgctaatac     120

cgcataagat ctaaggatga aagcagggga ccgcaaggcc ttgcgcgaac ggagcggccg     180

atggcagatt aggtagttgg tgggataaaa gcttaccaag ccgacgatct gtagctggtc     240

tgagaggacg accagccaca ctgggactga gacacggccc agactcctac gggaggcagc     300

agtggggaat tttggacaat gggcgaaagc ctgatccagc catgccgcgt gcaggatgaa     360

ggccttcggg ttgtaaactg cttttgtacg gaacgaaaag actctggtta atacctgggg     420

tccatgacgg taccgtaaga ataagcaccg gctaactacg tgccagcagc cgcggtaata     480

cgtagggtgc aagcgttaat cggaattact gggcgtaaag cgtgcgcagg cggttatata     540

agacagatgt gaaatccccg ggctcaacct gggaactgca tttgtgactg tatagctaga     600

gtacggtaga gggggatgga attccgcgtg tagcagtgaa atgcgtagat atgcggagga     660

acaccgatgg cgaaggcaat cccctggacc tgtactgacg ctcatgcacg aaagcgtggg     720

gagcaaacag gattagatac cctggnagtc cacgccctan cgatgtcaac tgnnngntgg     780

gtcttcnctg actccagtaa cnaacgcann tacgcntgag ttgaccgnnt nnnnnnannn     840

nnnnnnnnna aactcaagan tgacgggacc cgnnncnagc gg                        882
```

<210> SEQ ID NO 29
<211> LENGTH: 874
<212> TYPE: DNA
<213> ORGANISM: Artificial Sequence
<220> FEATURE:
<223> OTHER INFORMATION: FM-1-13-27F_G06.ab1
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (775)..(777)
<223> OTHER INFORMATION: n is a, c, g, or t
<220> FEATURE:
<221> NAME/KEY: misc_feature
<222> LOCATION: (814)..(815)
<223> OTHER INFORMATION: n is a, c, g, or t
<220> FEATURE:
<221> NAME/KEY: misc_feature
<222> LOCATION: (831)..(834)
<223> OTHER INFORMATION: n is a, c, g, or t
<220> FEATURE:
<221> NAME/KEY: misc_feature
<222> LOCATION: (838)..(842)
<223> OTHER INFORMATION: n is a, c, g, or t
<220> FEATURE:
<221> NAME/KEY: misc_feature
<222> LOCATION: (844)..(847)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t

<400> SEQUENCE: 29
tgccttacct gcaagtcgaa cggtaacagg tcttcggatg ctgacgagtg gcgaacgggt 60
gagtaataca tcggaacgtg cccgatcgtg ggggataacg aagcgaaagc tttgctaata 120
ccgcataaga tctaaggatg aaagcagggg accgcaaggc cttgcgcgaa cggagcggcc 180
gatggcagat taggtagttg gtgggataaa agcttaccaa gccgacgatc tgtagctggt 240
ctgagaggac gaccagccac actgggactg agacacggcc cagactccta cgggaggcag 300
cagtggggaa ttttggacaa tgggcgaaag cctgatccag ccatgccgcg tgcaggatga 360
aggccttcgg gttgtaaact gcttttgtac ggaacgaaaa gactctggtt aatacctggg 420
gtccatgacg gtaccgtaag aataagcacc ggctaactac gtgccagcag ccgcggtaat 480
acgtagggtg caagcgttaa tcggaattac tgggcgtaaa gcgtgcgcag gcggttatat 540
aagacagatg tgaaatcccc gggctcaacc tgggaactgc atttgtgact gtatagctag 600
agtacggtag agggggatgg aattccgcgt gtagcagtga aatgcgtaga tatgcggagg 660
aacaccgatg gcgaaggcaa tcccctggac ctgtactgac gctcatgnca cgaaagcgtg 720
gggagcaaac aggattagat accctggtag tccacgccct ancgatgtca actgnnngtt 780
gggtcttcac tgactcagta cgaagctaac gccnntgaag ttgaccgcct nnnngtannn 840
nncnnnnaaa ctcaagnttg acgggacccg ccac 874

<210> SEQ ID NO 30
<211> LENGTH: 891
<212> TYPE: DNA
<213> ORGANISM: Artificial Sequence
<220> FEATURE:
<223> OTHER INFORMATION: FM1-1-3-27F_F08.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (729)..(730)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:

<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (824)..(828)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
<222> LOCATION: (839)..(840)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (887)..(888)
<223> OTHER INFORMATION: n is a, c, g, or t

<400> SEQUENCE: 30 ttannttgcaa gtcgaacggt aacaggtctt cggatgctga cgagtggcga acgggtgagt 60
aatacatcgg aacgtgcccg atcgtggggg ataacgaagc gaaagctttg ctaataccgc 120
ataagatcta aggatgaaag caggggaccg caaggccttg cgcgaacgga gcggccgatg 180
gcagattagg tagttggtgg gataaaagct taccaagccg acgatctgta gctggtctga 240
gaggacgacc agccacactg ggactgagac acggcccaga ctcctacggg aggcagcagt 300
ggggaatttt ggacaatggg cgaaagcctg atccagccat gccgcgtgca ggatgaaggc 360
cttcgggttg taaactgctt ttgtacggaa cggaaagact ctggttaata cctggggtcc 420

| | | | | |
|---|---|---|---|---|
| atgacggtac | cgtaagaata | agcaccggct | aactacgtgc | cagcagccgc | ggtaatacgt | 480 |
| agggtgcaag | cgttaatcgg | aattactggg | cgtaaagcgt | gcgcaggcgg | ttatataaga | 540 |
| cagatgtgaa | atccccgggc | tcaacctggg | aactgcattt | gtgactgtat | agctagagta | 600 |
| cggtagaggg | ggatggaatt | ccgcgtgtag | cagtgaaatg | cgtagatatg | cggaggaaca | 660 |
| ccgatggcga | aggcaatccc | ctggacctgt | actgacgctc | atgcacgaaa | gcgtggggag | 720 |
| caaacaggnn | tagataccct | ggnagtccac | gccctaaacg | atgtcaactg | gnttgttggg | 780 |
| tcttcactga | ctcagtaacg | aagctaangn | ggtgaagttg | accnnnnngg | nagtancgnn | 840 |
| cgcangagtg | nanacatact | cananggnan | ttgacgggng | anccgcnnaa | g | 891 |

<210> SEQ ID NO 31
<211> LENGTH: 938
<212> TYPE: DNA
<213> ORGANISM: Artificial Sequence
<220> FEATURE:
<223> OTHER INFORMATION: FM-1-14-27F_G07.ab1
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (706)..(709)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (841)..(842)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t

<400> SEQUENCE: 31

| | | | | |
|---|---|---|---|---|
| tgccttannt | gcaagtcgaa | cggtaacagg | tcttcggatg | ctgacgagtg | gcgaacgggt | 60 |
| gagtaataca | tcggaacgtg | cccgatcgtg | ggggataacg | aagcgaaagc | tttgctaata | 120 |

```
ccgcataaga tctaaggatg aaagcagggg accgcaaggc cttgcgcgaa cggagcggcc    180

gatggcagat taggtagttg gtgggataaa agcttaccaa gccgacgatc tgtagctggt    240

ctgagaggac gaccagccac actgggactg agacacggcc cagactccta cgggaggcag    300

cagtggggaa ttttggacaa tgggcgaaag cctgatccag ccatgccgcg tgcaggatga    360

aggccttcgg gttgtaaact gcttttgtac ggaacgaaaa gactctggtt aatacctggg    420

gtccatgacg gtaccgtaag aataagcacc ggctaactac gtgccagcag ccgcggtaat    480

acgtagggtg cgagcgttaa tcggaattac tgggcgtaaa gcgtgcgcag gcggttatat    540

aagacagatg tgaaatcccc gggctcaacc tgggaactgc atttgtgact gtatagctag    600

agtacggtag agggggatgg aattccgcgt gtagcagtga aatgcgtaga tatgcggagg    660

aacaccgatg ncgaagggca atcccctggg acctgtactg accccnnnnc aacgaaagcg    720

tggggagcaa acaggattaa gattaccctg gttagtccac cgcccctaaa cgatgtcaac    780

tggtttgttg ggttcttcac ctgacttcag taacgaagct aacngcgtgg aagttgaacg    840

nncctggggg agtacggccg ccagcgnttg aatganaacn tcgaaagnga acttggacgg    900

ngngaacccc gcaccaagcc gggngggaat ggaatggt                            938
```

<210> SEQ ID NO 32
<211> LENGTH: 871
<212> TYPE: DNA
<213> ORGANISM: Artificial Sequence
<220> FEATURE:
<223> OTHER INFORMATION: FM1-1-4-27F_F09.ab1
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (811)..(811)
<223> OTHER INFORMATION: n is a, c, g, or t
<220> FEATURE:
<221> NAME/KEY: misc_feature
<222> LOCATION: (834)..(841)
<223> OTHER INFORMATION: n is a, c, g, or t
<220> FEATURE:
<221> NAME/KEY: misc_feature
<222> LOCATION: (843)..(845)
<223> OTHER INFORMATION: n is a, c, g, or t

<400> SEQUENCE: 32

```
ccttanntgc aagtcgaacg gtaacaggtc ttcggatgct gacgagtggc gaacgggtga     60

gtaatacatc ggaacgtgcc cgatcgtggg ggataacgaa gcgaaagctt tgctaatacc    120

gcataagatc taaggatgaa agcaggggac cgcaaggcct tgcgcgaacg gagcggccga    180

tggcagatta ggtagttggt gggataaaag cttaccaagc cgacgatctg tagctggtct    240

gagaggacga ccagccacac tgggactgag acacggccca gactcctacg ggaggcagca    300

gtggggaatt ttggacaatg ggcgaaagcc tgatccagcc atgccgcgtg caggatgaag    360

gccttcgggt tgtaaactgc ttttgtacgg aacgaaaaga ctctggttaa tacctggggt    420

ccatgacggt accgtaagaa taagcaccgg ctaactacgt gccagcagcc gcggtaatac    480

gtagggtgca agcgttaatc ggaattactg ggcgtaaagc gtgcgcaggc ggttatataa    540
```

gacagatgtg aaatccccgg gctcaacctg ggaactgcat ttgtgactgt atagctagag 600
tacggtagag ggggatggaa ttccgcgtgt agcagtgaaa tgcgtagata tgcggaggaa 660
caccgatggc gaaagncaat cccctggacc tgtactgacg ctcatgcacg aaagcgtggg 720
gagcaaacag gattagatac cctggnagtc cacgccctaa acgatgtcaa ctggttgttg 780
ggtcttcact gactcagtac gaagctaacg ngtgaagttg accgcctggg gagnnnnnnn 840
nannngaaac tcaaaggaat tgacgggaac c 871

<210> SEQ ID NO 33
<211> LENGTH: 882
<212> TYPE: DNA
<213> ORGANISM: Artificial Sequence
<220> FEATURE:
<223> OTHER INFORMATION: FM-1-15-27F_G08.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (821)..(823)
<223> OTHER INFORMATION: n is a, c, g, or t
<220> FEATURE:
<221> NAME/KEY: misc_feature
<222> LOCATION: (828)..(829)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (838)..(841)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (864)..(865)
<223> OTHER INFORMATION: n is a, c, g, or t
<220> FEATURE:
<221> NAME/KEY: misc_feature
<222> LOCATION: (868)..(870)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (878)..(879)
<223> OTHER INFORMATION: n is a, c, g, or t

<400> SEQUENCE: 33
cttanntgca gtcgaacggt aacaggtctt cggatgctga cgagtggcga acgggtgagt 60
aatacatcgg aacgtgcccg agagtggggg ataacgaagc gaaagctttg ctaataccgc 120
atacgatctc aggatgaaag caggggaccg caaggccttg cgctcacgga gcggccgatg 180
gcagattagg tagttggtgg gataaaagct taccaagccg acgatctgta gctggtctga 240
gaggacgacc agccacactg ggactgagac acggcccaga ctcctacggg aggcagcagt 300
ggggaatttt ggacaatggg cgcaagcctg atccagccat gccgcgtgca ggatgaaggc 360
cttcgggttg taaactgctt ttgtacggaa cgaaaagact ctggttaata cctggggtcc 420
atgacggtac cgtaagaata agcaccggct aactacgtgc cagcagccgc ggtaatacgt 480
agggtgcgag cgttaatcgg aattactggg cgtaaagcgt gcgcaggcgg ttatataaga 540
cagatgtgaa atccccgggc tcaacctggg aactgcattt gtgactgtat agctagagta 600
cggcagaggg ggatggaatt ccgcgtgtag cagtgaaatg cgtagatatg cggaggaaca 660
ccgatggcga aggcaatccc ctgggcctgt actgacgctc atgcacgaaa gcgtggggag 720
caaacaggat tagataccct ggnagtccac gccctaacga tgtcaactgg ntgttgggtc 780
ttcactgact cagtaacgaa gctaacgcgn gaagttgacc nnnggggnnt acgnnncnnn 840
ntnaactcaa ggaattgacg gggnnccnnn caancggnng gg 882

<210> SEQ ID NO 34
<211> LENGTH: 850
<212> TYPE: DNA
<213> ORGANISM: Artificial Sequence
<220> FEATURE:
<223> OTHER INFORMATION: FM1-1-6-27F_F11.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (771)..(773)
<223> OTHER INFORMATION: n is a, c, g, or t
<220> FEATURE:
<221> NAME/KEY: misc_feature
<222> LOCATION: (821)..(822)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (835)..(837)
<223> OTHER INFORMATION: n is a, c, g, or t
<220> FEATURE:
<221> NAME/KEY: misc_feature
<222> LOCATION: (841)..(841)
<223> OTHER INFORMATION: n is a, c, g, or t

<400> SEQUENCE: 34
tgcttanntg caagtcgaac ggtaacaggt cttcggatgc tgacgagtgg cgaacgggtg 60
agtaatacat cggaacgtgc ccgatcgtgg gggataacga agcgaaagct ttgctaatac 120
cgcataagat ctaaggatga aagcagggga ccgcaaggcc ttgcgcgaac ggagcggccg 180
atggcagatt aggtagttgg tgggataaaa gcttaccaag ccgacgatct gtagctggtc 240
tgagaggacg accagccaca ctgggactga gacacggccc agactcctac gggaggcagc 300
agtggggaat tttggacaat gggcgaaagc ctgatccagc catgccgcgt gcaggatgaa 360
ggccttcggg ttgtaaactg cttttgtacg gaacgaaaag actctggtta atacctgggg 420
tccatgacgg taccgtaaga ataagcaccg gctaactacg tgccagcagc cgcggtaata 480
cgtagggtgc aagcgttaat cggaattact gggcgtaaag cgtgcgcagg cggttatata 540
agacagatgt gaaatccccg ggctcaacct gggaactgca tttgtgactg tatagctaga 600
gtacggtaga gggggatgga attccgcgtg tagcagtgaa atgcgtagat atgcggagga 660
acaccgatgg cgaangcaat cccctggacc tgtactgacg ctcatgcacg aaagcgtggg 720
gagcaaacag gattagatac cctggnagtc ncgccctaac gatgtcaact nnngttgggt 780
cttcactgac tcagtaacga agctaacgcg tgaagttgac nncctgggga ntacnnncgc 840 nagggttgaa 850

<210> SEQ ID NO 35
<211> LENGTH: 859
<212> TYPE: DNA
<213> ORGANISM: Artificial Sequence
<220> FEATURE:
<223> OTHER INFORMATION: FM1-1-7-27F_F12.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (692)..(696)
<223> OTHER INFORMATION: n is a, c, g, or t
<220> FEATURE:
<221> NAME/KEY: misc_feature
<222> LOCATION: (698)..(700)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:
<221> NAME/KEY: misc_feature
<222> LOCATION: (779)..(780)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (793)..(796)
<223> OTHER INFORMATION: n is a, c, g, or t
<220> FEATURE:
<221> NAME/KEY: misc_feature
<222> LOCATION: (827)..(828)
<223> OTHER INFORMATION: n is a, c, g, or t

<400> SEQUENCE: 35
ttanntgcag tcgaacggta acaggtcttc ggatgctgac gagtggcgaa cgggtgagta 60
atacatcgga acgtgcccga tcgtggggga taacgaagcg aaagctttgc taataccgca 120
taagatctaa ggatgaaagc aggggaccgc aaggccttgc gcgaacggag cggccgatgg 180
cagattaggt agttggtggg ataaaagctt accaagccga cgatctgtag ctggtctgag 240
aggacgacca gccacactgg gactgagaca cggcccagac tcctacggga ggcagcagtg 300

-continued gggaattttg gacaatgggc gaaagcctga tccagccatg ccgcgtgcag gatgaaggcc 360
ttcgggttgt aaactgcttt tgtacggaac gaaaagactc tggttaatac ctggggtcca 420
tgacggtacc gtaagaataa gcaccggcta actacgtgcc agcagccgcg gtaatacgta 480
gggtgcaagc gttaatcgga attactgggc gtaaagcgtg cgcaggcggt tatgtaagac 540
agatgtgaaa tccccgggct caacctggga actgcatttg tgactgcata gctagagtac 600
ggcagagggg gatggaattc cgcgtgtagc agtgaaatgc gtagatatgc ggaggaacac 660
cgatggcgaa ggcaatcccc tgggcctgta cnnnnncnnn atgcacgaaa gcgtggggag 720
caaacaggat tagataccct ggnagtccac gccctaacga tgtcaactgg tngttgggnn 780
ttcnctgact cannnngaag ctacgcgtga gttgaccgcc tgggggnnta cggccgcagg 840
ttgaaacttc aaaggaatt 859

<210> SEQ ID NO 36
<211> LENGTH: 759
<212> TYPE: DNA
<213> ORGANISM: Artificial Sequence
<220> FEATURE:
<223> OTHER INFORMATION: FM-1-8-27F_G01.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (645)..(646)
<223> OTHER INFORMATION: n is a, c, g, or t
<220> FEATURE:
<221> NAME/KEY: misc_feature
<222> LOCATION: (648)..(654)
<223> OTHER INFORMATION: n is a, c, g, or t
<220> FEATURE:
<221> NAME/KEY: misc_feature
<222> LOCATION: (656)..(657)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (661)..(662)
<223> OTHER INFORMATION: n is a, c, g, or t
<220> FEATURE:
<221> NAME/KEY: misc_feature
<222> LOCATION: (664)..(684)
<223> OTHER INFORMATION: n is a, c, g, or t
<220> FEATURE:
<221> NAME/KEY: misc_feature
<222> LOCATION: (686)..(692)
<223> OTHER INFORMATION: n is a, c, g, or t
<220> FEATURE:
<221> NAME/KEY: misc_feature
<222> LOCATION: (694)..(696)
<223> OTHER INFORMATION: n is a, c, g, or t
<220> FEATURE:
<221> NAME/KEY: misc_feature
<222> LOCATION: (704)..(706)
<223> OTHER INFORMATION: n is a, c, g, or t

<400> SEQUENCE: 36
cttanntgca gtcgaacggt aacaggtctt cggatgctga cgagtggcga acgggtgagt 60
aatacatcgg aacgtgcccg atcgtggggg ataacgaagc gaaagctttg ctaataccgc 120
ataagatcta aggatgaaag caggggaccg caaggccttg cgcgaacgga gcggccgatg 180

-continued

```
gcagattagg tagttggtgg gataaaagct taccaagccg acgatctgta gctggtctga    240

gaggacgacc agccacactg ggactgagac acggcccaga ctcctacggg aggcagcagt    300

ggggaatttt ggacaatggg cgaaagcctg atccagccat gccgcgtgca ggatgaaggc    360

cttcgggttg taaactgctt ttgtacggaa cgaaaagact ctggttaata cctggggtcc    420

atgacggtac cgtaagaata agcaccggct aactacgtgc cagcagccgc ggtaatacgt    480

agggtgcgag cgttaatcgg aattactggg cgtaaagcgt gcgcaggcgg ttatataaga    540

cagatgtgaa atccccgggc tcaacctggg aactgcattt gtgactgtat agctagagta    600

cggtagaggg ggatggaatt ccgcgtgtag cagtgaaatg cgnanngnnn nnnntnnanc    660

nncnnnnnnn nnnnnnnnnn nnnntnnnnn nnannnacgc aaannnaagc gtggggagca    720

aacaggatta gataccctgg tagtccacgc cctaaacga                           759


<210> SEQ ID NO 37
<211> LENGTH: 823
<212> TYPE: DNA
<213> ORGANISM: Artificial Sequence
<220> FEATURE:
<223> OTHER INFORMATION: FM-1-9-27F_G02.ab1
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (652)..(653)
<223> OTHER INFORMATION: n is a, c, g, or t
<220> FEATURE:
<221> NAME/KEY: misc_feature
<222> LOCATION: (655)..(656)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (684)..(685)
<223> OTHER INFORMATION: n is a, c, g, or t
<220> FEATURE:
<221> NAME/KEY: misc_feature
<222> LOCATION: (700)..(701)
<223> OTHER INFORMATION: n is a, c, g, or t
<220> FEATURE:
<221> NAME/KEY: misc_feature
<222> LOCATION: (705)..(708)
<223> OTHER INFORMATION: n is a, c, g, or t
<220> FEATURE:
<221> NAME/KEY: misc_feature
<222> LOCATION: (710)..(713)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (790)..(791)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (811)..(811)
```

```
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (815)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t

<400> SEQUENCE: 37

ggctgcctta nntgcaagtc gaacggtaac aggtcttcgg atgctgacga gtggcgaacg     60

ggtgagtaat acatcggaac gtgcccgatc gtgggggata acgaagcgaa agctttgcta    120

ataccgcata agatctaagg atgaaagcag gggaccgcaa ggccttgcgc gaacggagcg    180

gccgatggca gattaggtag ttggtgggat aaaagcttac caagccgacg atctgtagct    240

ggtctgagag gacgaccagc cacactggga ctgagacacg gcccagactc ctacgggagg    300

cagcagtggg gaattttgga caatgggcga aagcctgatc cagccatgcc gcgtgcagga    360

tgaaggcctt cgggttgtaa actgcttttg tacggaacga aaagactctg gttaatacct    420

ggggtccatg acggtaccgt aagaataagc accggctaac tacgtgccag cagccgcggt    480

aatacgtagg gtgcaagcgt taatcggaat tactgggcgt aaagcgtgcg caggcggtta    540

tataagacag atgtgaaatc cccgggctca acctgggaac tgcatttgtg actgtatagc    600

tagagtacgg tagaggggga tggaattccg cgtgtagcag tgaaatgcgt annanngngg    660

aggaacaccg gatggcgaag gcanncccct ggacctgtan ngacnnnnan nnnccgaaag    720

cgtggggagc aaacaggatt agataccctg gtagtcacgc ctaacgatgt cactggtngn    780

tgggtcttcn ntgactcant acgaagctaa ncncnnaant gac                      823


<210> SEQ ID NO 38
<211> LENGTH: 868
<212> TYPE: DNA
<213> ORGANISM: Artificial Sequence
<220> FEATURE:
<223> OTHER INFORMATION: Gam1-1-10-27F_C10.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (620)..(626)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (643)..(650)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (788)..(790)
<223> OTHER INFORMATION: n is a, c, g, or t
```

<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (812)..(813)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (854)..(855)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t

<400> SEQUENCE: 38
tncnntgcaa gtcgagcggc agcgggaaag tagcttgcta cttttgccgg cgagcggcgg 60
acgggtgagt aatgcctggg gatctgccca gtcgaggggg ataactactg gaaacggtag 120
ctaataccgc atacgcccta cgggggaaag caggggacct tcgggccttg cgcgattgga 180
tgaacccagg tgggattagc tagttggtga ggtaacggct caccaaggcg acgatcccta 240
gctggtctga gaggatgatc agccacactg gaactgagac acggtccaga ctcctacggg 300
aggcagcagt ggggaatatt gcacaatggg ggaaaccctg atgcagccat gccgcgtgtg 360
tgaagaaggc cttcgggttg taaagcactt tcagcgagga ggaaaggtca gtagctaata 420
tctgctggct gtgacgttac tcgcagaaga agcaccggct aactccgtgc cagcagccgc 480
ggtaatacgg agggtgcaag cgttaatcgg aattactggg cgtaaagcgc acgcaggcgg 540
ttggataagt tagatgtgaa agccccgggc tcaacctggg aattgcattt aaaactgtcc 600
agctagagtc ttgtagaggn nnnnnntatt ttccagggtg nannnnnnnn aaatgcgtag 660
agatctggag gaataccggt ggcgaaggcg gccccctgga caaagactga cgctcngtgc 720
gaaagcgtgg ggagcaaaca ggattagata ccctggtagt ccacgccgta acgatgtcga 780
tttggagnnn tgtntccntn agacgtgntt cnnagctaac gcgttaaatc gacnnngggg 840
antacggngc aagnnanctc aaatgaat 868

<210> SEQ ID NO 39
<211> LENGTH: 863
<212> TYPE: DNA
<213> ORGANISM: Artificial Sequence
<220> FEATURE:

<223> OTHER INFORMATION: Gam1-1-11-27F_C11.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (713)..(717)
<223> OTHER INFORMATION: n is a, c, g, or t

<400> SEQUENCE: 39
taacnntgca agtcgagcgg tagcacagga gagcttgctc tctgggtgac gagcggcgga 60
cgggtgagta atgtctggga aactgcctga tggaggggga taactactgg aaacggtagc 120
taataccgca taacgtcgca agaccaaaga gggggacctt cgggcctctt gccatcagat 180
gtgcccagat gggattagct agtaggtggg gtaacggctc acctaggcga cgatccctag 240
ctggtctgag aggatgacca gccacactgg aactgagaca cggtccagac tcctacggga 300
ggcagcagtg gggaatattg cacaatgggc gcaagcctga tgcagccatg ccgcgtgtat 360
gaagaaggcc ttcgggttgt aaagtacttt cagcggggag gaaggtgttg aggttaataa 420
cctcagcaat tgacgttacc cgcagaagaa gcaccggcta actccgtgcc agcagccgcg 480
gtaatacgga gggtgcaagc gttaatcgga attactgggc gtaaagcgca cgcaggcggt 540
ctgtcaagtc ggatgtgaaa tccccgggct caacctggga actgcattcg aaactggcag 600
gctagagtct tgtagagggg ggtagnnttc nccagggtgt agcggtgaaa tgcgtaggag 660
atctggagga ataccggtgg cgaangcggc cccctggaca aagactgacg ctnnnnngcg 720
aaagcgtggg gagcaaacag gattagatac cctggtagtc cacgccgtaa cgatgtcgac 780
ttggaggttg tgcccttgag gcgtggcttc cgggagctaa cgcgttaagt cgaccggcct 840
gggggagtac gggccgcaag gtt 863

<210> SEQ ID NO 40
<211> LENGTH: 843
<212> TYPE: DNA
<213> ORGANISM: Artificial Sequence
<220> FEATURE:
<223> OTHER INFORMATION: Gam1-1-12-27F_C12.ab1
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (639)..(640)
<223> OTHER INFORMATION: n is a, c, g, or t
<220> FEATURE:
<221> NAME/KEY: misc_feature
<222> LOCATION: (700)..(704)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (731)..(733)
<223> OTHER INFORMATION: n is a, c, g, or t

<400> SEQUENCE: 40
cnntgcaagt cgagcggcag cgggaaagta gcttgctact tttgccggcg agcggcggac 60
gggtgagtaa tgcctgggga tctgcccagt cgagggggat aactactgga aacggtagct 120
aataccgcat acgccctacg ggggaaagca ggggaccttc gggccttgcg cgattggatg 180
aacccaggtg ggattagcta gttggtgagg taacggctca ccaaggcgac gatccctagc 240
tggtctgaga ggatgatcag cacactggaa ctgagacacg gtccagactc ctacgggagg 300
cagcagtggg gaatattgca caatggggga aaccctgatg cagccatgcc gcgtgtgtga 360
agaaggcctt cgggttgtaa agcactttca gcgaggagga aaggtcagta gctaatatct 420
gctggctgtg acgttactcg cagaagaagc accggctaac tccgtgccag cagccgcggt 480
aatacggagg gtgcaagcgt taatcggaat tactgggcgt aaagcgcacg caggcggttg 540
gataagttag atgtgaaagc cccgggctca acctgagaat tgcatttaaa actgtccagc 600
tagagtcttg tagagggggg tagaattcca ggtgtaggnn tgaaatgcgt agagatctgg 660
aggaataccg gtggcgaagg cggccccctg gacaaagacn nnnngccnca gntgcnaaag 720
gcngtggggg nnncaaacag gattagatac cctggtagtc cacgcccgta aacgatgtcg 780
acttggaggt tgtgcccttg aggcgtggct tccggagcta acgcgttaag tcgaccgccc 840
tgg 843

<210> SEQ ID NO 41
<211> LENGTH: 794
<212> TYPE: DNA
<213> ORGANISM: Artificial Sequence
<220> FEATURE:
<223> OTHER INFORMATION: Gam1-1-1-27F_C01.ab1
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (616)..(617)
<223> OTHER INFORMATION: n is a, c, g, or t
<220> FEATURE:
<221> NAME/KEY: misc_feature
<222> LOCATION: (657)..(659)
<223> OTHER INFORMATION: n is a, c, g, or t
<220> FEATURE:

<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t

<400> SEQUENCE: 41
gnnacnntgc aagtcgaacg gtagcacaga ggagcttgct ccttgggtga cgagtggcgg 60
acgggtgagt aatgtctggg aaactgcccg atggaggggg ataactactg gaaacggtag 120
ctaataccgc ataacgtcgc aagaccaaag agggggacct tcgggcctct tgccatcgga 180
tgtgcccaga tgggattagc tagtaggtgg ggtaacggct cacctaggcg acgatcccta 240
gctggtctga gaggatgacc agccacactg gaactgagac acggtccaga ctcctacggg 300
aggcagcagt ggggaatatt gcacaatggg cgcaagcctg atgcagccat gccgcgtgta 360
tgaagaaggc cttcgggttg taaagtactt tcagcgagga ggaaggtgtt gtggttaata 420
actgcagcaa ttgacgttac tcgcagaaga agcaccggct aactccgtgc cagcagccgc 480
ggtaatacgg agggtgcaag cgttaatcgg aattactggg cgtaaagcgc acgcaggcgg 540
tctgtcaagt cggatgtgaa atccccgggc tcaacctggg aactgcatcc gaaactggcn 600
gctagagtct tgnagnnggg ggggtagaat tccaggtgta gcggtgaaat gcgtagnnnt 660
ctggaggaat accggtggcg aancggcccc tggacaaana ctgacgctca ntgcgatagc 720
gtnggnagca aacaggatta gataccctgg tagtccacgc cgtaaacgat tgtcnacttg 780
gaggttngtg cctt 794

<210> SEQ ID NO 42
<211> LENGTH: 884
<212> TYPE: DNA
<213> ORGANISM: Artificial Sequence
<220> FEATURE:
<223> OTHER INFORMATION: Gam1-1-13-27F_G06.ab1
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (603)..(605)
<223> OTHER INFORMATION: n is a, c, g, or t
<220> FEATURE:
<221> NAME/KEY: misc_feature
<222> LOCATION: (625)..(629)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (744)..(745)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (840)..(842)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t

<400> SEQUENCE: 42

```
tanncatgca gtcgagcggt aacacaggga gcttgctcct gggtgacgag cggcggacgg     60

gtgagtaatg tctgggaaac tgcctgatgg agggggataa ctactggaaa cggtagctaa    120

taccgcataa cgtcgcaaga ccaaagaggg ggaccttcgg gcctcttgcc atcagatgtg    180

cccagatggg attagctagt aggtggggta atggctcacc taggcgacga tccctagctg    240

gtctgagagg atgaccagcc acactggaac tgagacacgg tccagactcc tacgggaggc    300

agcagtgggg aatattgcac aatgggcgca agcctgatgc agccatgccg cgtgtatgaa    360

gaaggccttc gggttgtaaa gtactttcag cggggaggaa ggcgataagg ttaataacct    420

tgtcgattga cgttacccgc agaagaagca ccggctaact ccgtgccagc agccgcggta    480

atacggaggg tgcaagcgtt aatcggaatt actgggcgta aagcgcacgc aggcggtctg    540

tcaagtcgga tgtgaaatcc ccgggctcaa cctgggaact gcattcgaaa ctggcaggct    600

aannntttgg taagaggggg ggtannnnnc caggtgtagc ggtgaaatgc gtagagatct    660

ggaggaatac cggtggcgaa ngcggccccc tggacaaaga ctgacgctcn gtgcgaaagc    720

gtggggagca aacaggatta gatnncccng gtagtcacgc cgtaaacgat gtcgacttgg    780
```

agttgtgccc ttgaggcgtn gcttccgnag ctaacgngtt aagtcgacgn cngnnngagn 840
nngtacggcc gcangttaaa actcaaatga attgangggg gccc 884

<210> SEQ ID NO 43
<211> LENGTH: 876
<212> TYPE: DNA
<213> ORGANISM: Artificial Sequence
<220> FEATURE:
<223> OTHER INFORMATION: Gam1-1-15-27F_G08.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (620)..(622)
<223> OTHER INFORMATION: n is a, c, g, or t
<220> FEATURE:
<221> NAME/KEY: misc_feature
<222> LOCATION: (640)..(641)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (750)..(758)
<223> OTHER INFORMATION: n is a, c, g, or t
<220> FEATURE:
<221> NAME/KEY: misc_feature
<222> LOCATION: (764)..(765)
<223> OTHER INFORMATION: n is a, c, g, or t
<220> FEATURE:
<221> NAME/KEY: misc_feature
<222> LOCATION: (767)..(769)
<223> OTHER INFORMATION: n is a, c, g, or t
<220> FEATURE:
<221> NAME/KEY: misc_feature
<222> LOCATION: (776)..(778)
<223> OTHER INFORMATION: n is a, c, g, or t
<220> FEATURE:
<221> NAME/KEY: misc_feature
<222> LOCATION: (781)..(785)
<223> OTHER INFORMATION: n is a, c, g, or t
<220> FEATURE:
<221> NAME/KEY: misc_feature
<222> LOCATION: (791)..(792)
<223> OTHER INFORMATION: n is a, c, g, or t
<220> FEATURE:
<221> NAME/KEY: misc_feature
<222> LOCATION: (796)..(797)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t
<220> FEATURE:
<221> NAME/KEY: misc_feature
<222> LOCATION: (807)..(809)
<223> OTHER INFORMATION: n is a, c, g, or t
<220> FEATURE:
<221> NAME/KEY: misc_feature
<222> LOCATION: (811)..(811)
<223> OTHER INFORMATION: n is a, c, g, or t
<220> FEATURE:
<221> NAME/KEY: misc_feature
<222> LOCATION: (814)..(818)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (866)..(866)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t

<400> SEQUENCE: 43
tacnnatgca gtcgagcggt aacacaggga gcttgctcct gggtgacgag cggcggacgg 60
gtgagtaatg tctgggaaac tgcctgatgg agggggataa ctactggaaa cggtagctaa 120
taccgcataa cgtcgcaaga ccaaagaggg ggaccttcgg gcctcttgcc atcagatgtg 180
cccagatggg attagctagt aggtggggta atggctcacc taggcgacga tccctagctg 240
gtctgagagg atgaccagcc acactggaac tgagacacgg tccagactcc tacgggaggc 300
agcagtgggg aatattgcac aatgggcgca agcctgatgc agccatgccg cgtgtatgaa 360
gaaggccttc gggttgtaaa gcactttcag cgaggaggaa aggttggtag ctaatatctg 420
ccagctgtga cgttactcgc agaagaagca ccggctaact ccgtgccagc agccgcggta 480
atacggaggg tgcaagcgtt aatcggaatt actgggcgta aagcgcacgc aggcggttgg 540
ataagttaga tgtgaaagcc ccgggctcaa cctgggaatt gcatttaaaa ctgtccagct 600

-continued

```
agagtcttgt aaggggggggn nnaaattcca ggtgtagcgn ngaaatgcgt agagatctgg    660

aggaataccg gtggcgaagg cggccccctg gacaaaagac tgacgctcnc angtgcgaaa    720

gcgtgggagc aaacaggatt agataccctn nnnnnnnnca cgcnnannnt gatgcnnntt    780

nnnnnggctg nngtcnntga nanacgnnnc ncgnnnnnct agcnactnan tcaancgacn    840

gcnagnncag tncngncggc naggtnaant naaatg                               876
```

```
<210> SEQ ID NO 44
<211> LENGTH: 887
<212> TYPE: DNA
<213> ORGANISM: Artificial Sequence
<220> FEATURE:
<223> OTHER INFORMATION: Gam1-1-16-27F_G09.ab1
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (600)..(605)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (631)..(633)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (686)..(686)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (786)..(788)
<223> OTHER INFORMATION: n is a, c, g, or t
<220> FEATURE:
<221> NAME/KEY: misc_feature
<222> LOCATION: (825)..(828)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (841)..(841)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
```

<222> LOCATION: (873)..(873)
<223> OTHER INFORMATION: n is a, c, g, or t
<220> FEATURE:
<221> NAME/KEY: misc_feature
<222> LOCATION: (878)..(878)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t

<400> SEQUENCE: 44
taccntgcaa gtcgaacggt agcacagagg agcttgctcc ttgggtgacg agtggcggac 60
gggtgagtaa tgtctgggaa actgcccgat ggagggggat aactactgga aacggtagct 120
aataccgcat aacgtcgcaa gaccaaagag ggggaccttc gggcctcttg ccatcggatg 180
tgcccagatg ggattagcta gtaggtgggg taacggctca cctaggcgac gatccctagc 240
tggtctgaga ggatgaccag ccacactgga actgagacac ggtccagact cctacgggag 300
gcagcagtgg ggaatattgc acaatgggcg caagcctgat gcagccatgc cgcgtgtatg 360
aagaaggcct tcgggttgta aagtactttc agcgaggagg aaggtgttgt ggttaataac 420
cacagcaatt gacgttactc gcagaagaag caccggctaa ctccgtgcca gcagccgcgg 480
taatacggag ggtgcaagcg ttaatcggaa ttactgggcg taaagcgcac gcaggcggtc 540
tgtcaagtcg gatgtgaaat ccccgggctc aacctgggaa ctgcatccga aactggcagn 600
nnnnnattct ttgtagaggg gggtannant nnnaggtgta gcggtgaaat gcgtagagat 660
ctggaggaat accggtggcg aagngnggcc ccntgnggac aaagactgac gctcngtgcg 720
aaagcgtggg gagcaaacag gattagatac cctgggtagt ccacgccgta aacgatgtcg 780
acttgnnngt tgtgcccttg aggcgtggct tccggagcta acgcnnnntc gacnnngggg 840
ngtacggccg caggtaaact caaangaatt ganggggncc gccncaa 887

<210> SEQ ID NO 45
<211> LENGTH: 901
<212> TYPE: DNA
<213> ORGANISM: Artificial Sequence
<220> FEATURE:
<223> OTHER INFORMATION: Gam1-1-17-27F_G10.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:

<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (755)..(757)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (815)..(817)
<223> OTHER INFORMATION: n is a, c, g, or t
<220> FEATURE:
<221> NAME/KEY: misc_feature
<222> LOCATION: (820)..(821)
<223> OTHER INFORMATION: n is a, c, g, or t
<220> FEATURE:
<221> NAME/KEY: misc_feature
<222> LOCATION: (823)..(824)
<223> OTHER INFORMATION: n is a, c, g, or t
<220> FEATURE:
<221> NAME/KEY: misc_feature
<222> LOCATION: (831)..(834)
<223> OTHER INFORMATION: n is a, c, g, or t
<220> FEATURE:
<221> NAME/KEY: misc_feature
<222> LOCATION: (843)..(844)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (849)..(852)
<223> OTHER INFORMATION: n is a, c, g, or t
<220> FEATURE:
<221> NAME/KEY: misc_feature
<222> LOCATION: (857)..(861)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (881)..(881)
<223> OTHER INFORMATION: n is a, c, g, or t
<220> FEATURE:
<221> NAME/KEY: misc_feature
<222> LOCATION: (890)..(890)
<223> OTHER INFORMATION: n is a, c, g, or t
<220> FEATURE:
<221> NAME/KEY: misc_feature
<222> LOCATION: (892)..(892)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t

<400> SEQUENCE: 45

```
tacnntgcaa gtcgagcggc agcgggaaag tagcttgcta cttttgccgg cgagcggcgg     60

acgggtgagt aatgcctggg gatctgccca gtcgaggggg ataactactg gaaacggtag    120

ctaataccgc atacgcccta cgggggaaag caggggacct tcgggccttg cgcgattgga    180

tgaacccagg tgggattagc tagttggtga ggtaacggct caccaaggcg acgatcccta    240

gctggtctga gaggatgatc agccacactg gaactgagac acggtccaga ctcctacggg    300

aggcagcagt ggggaatatt gcacaatggg ggaaaccctg atgcagccat gccgcgtgtg    360

tgaagaaggc cttcgggttg taaagcactt tcagcgagga ggaaaggtca gtagctaata    420

tctgctggct gtgacgttac tcgcagaaga agcaccggct aactccgtgc cagcagccgc    480

ggtaatacgg agggtgcaag cgttaatcgg aattactggg cgtaaagcgc acgcaggcgg    540

ttggataagt tagatgtgaa agccccgggc tcaacctggg aattgcattt aaaactgtcc    600

agctagagtc ttgtagaggg gggtagaatt ccanggtgta gcggtgaaan gcgtagagat    660

ctggnggaat acnggtggcg aaggcggccc cctggacaaa gactgacgct cantgcgaaa    720

gcgtggggag caaacaggat aaatncccng ngntnnncnc cccgtaaacn atgtcgattt    780

ggaaggctgn ggtccttgaa aacgtggntt ccggnnnctn nanncgttaa nnnnacaccc    840

ccnngnggnn nnggagnnnn ncgggccgca nggttaaaac ncaaatgaan tngnangggg    900

g                                                                    901
```

<210> SEQ ID NO 46
<211> LENGTH: 884
<212> TYPE: DNA
<213> ORGANISM: Artificial Sequence
<220> FEATURE:
<223> OTHER INFORMATION: Gam1-1-18-27F_G11.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (624)..(625)
<223> OTHER INFORMATION: n is a, c, g, or t
<220> FEATURE:
<221> NAME/KEY: misc_feature
<222> LOCATION: (673)..(675)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:

<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (801)..(804)
<223> OTHER INFORMATION: n is a, c, g, or t
<220> FEATURE:
<221> NAME/KEY: misc_feature
<222> LOCATION: (807)..(811)
<223> OTHER INFORMATION: n is a, c, g, or t
<220> FEATURE:
<221> NAME/KEY: misc_feature
<222> LOCATION: (814)..(815)
<223> OTHER INFORMATION: n is a, c, g, or t
<220> FEATURE:
<221> NAME/KEY: misc_feature
<222> LOCATION: (821)..(823)
<223> OTHER INFORMATION: n is a, c, g, or t
<220> FEATURE:
<221> NAME/KEY: misc_feature
<222> LOCATION: (825)..(827)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (843)..(845)
<223> OTHER INFORMATION: n is a, c, g, or t
<220> FEATURE:
<221> NAME/KEY: misc_feature
<222> LOCATION: (848)..(849)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (866)..(867)
<223> OTHER INFORMATION: n is a, c, g, or t

<400> SEQUENCE: 46
cngncnnncn ntgcagtcga gcggtaacac agggagcttg ctcctgggtg acgagcggcg 60
gacgggtgag taatgtctgg gaaactgcct gatggagggg gataactact ggaaacggta 120
gctaataccg cataacgtcg caagaccaaa gagggggacc ttcgggcctc ttgccatcag 180
atgtgcccag atgggattag ctagtaggtg gggtaatggc tcacctaggc gacgatccct 240
agctggtctg agaggatgac cagccacact ggaactgaga cacggtccag actcctacgg 300
gaggcagcag tggggaatat tgcacaatgg gcgcaagcct gatgcagcca tgccgcgtgt 360
atgaagaagg ccttcgggtt gtaaagtact ttcagcgggg aggaaggcga taaggttaat 420
aaccttgtcg attgacgtta cccgcagaag aagcaccggc taactccgtg ccagcagccg 480
cggtaatacg gagggtgcaa gcgttaatcg gaattactgg gcgtaaagcg cacgcaggcg 540
gtctgtcaag tcggatgtga aatccccggg ctcaacctgg gaactgcatt cgaaactggc 600
aggctagagt cttgtagggg gggnnagaat tccaggtgta gcggtgaaat gcgtagagat 660
ctggaggaat acnnntggcg aaggcggccc cctggacaaa gactgacgct cagggtgcga 720
aagcgtgggg agcaaacagg attagatacc ctggnagtcc acgccgtaaa cgatgtcgac 780
ttggaaggtt gngngccctt nnnnggnnnn ngcnntccgg nnncnnnaac nccgttaagt 840
ccnnncgnnc ctgggggaga tnccgnnccg ccaagggtta aaac 884

<210> SEQ ID NO 47
<211> LENGTH: 806
<212> TYPE: DNA
<213> ORGANISM: Artificial Sequence
<220> FEATURE:
<223> OTHER INFORMATION: Gam1-1-19-27F_G02.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (702)..(704)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (773)..(775)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t

<400> SEQUENCE: 47
tgcnagtcga gcggtagcac agggagcttg ctcctgggtg acgagcggcg gacgggtgag 60
taatgtctgg gaaactgcct gatggagggg gataactact ggaaacggta gctaataccg 120
cataacgtcg caagaccaaa gagggggacc ttcgggcctc ttgccatcag atgtgcccag 180
atgggattag ctagtaggtg gggtaatggc tcacctaggc gacgatccct agctggtctg 240
agaggatgac cagccacact ggaactgaga cacggtccag actcctacgg gaggcagcag 300
tggggaatat tgcacaatgg gcgcaagcct gatgcagcca tgccgcgtgt atgaagaagg 360
ccttcgggtt gtaaagtact ttcagcgggg aggaaggtgt tgaggttaat aacctcagca 420
attgacgtta cccgcagaag aagcaccggc taactccgtg ccagcagccg cggtaatacg 480
gagggtgcaa gcgttaatcg gaattactgg gcgtaaagcg cacgcaggcg gtctgtcaag 540
tcggatgtga aatccccggg ctcaacctgg gaactgcatc cgaaactggc aggctagagt 600
cttgtagagg ggggtagaat tccaggtgta gcggtgaaat gcgtagagat ctggaggaat 660
accggtggcg aangcggccc cctggacaaa gactgacgct cnnngcnaaa agcgtgggga 720
gcnaacngga ttagataccc tggtagtcca cgccgtancg atgtcgactt ggnnntgtgc 780
ccttgagngn ggcttccgga nctaac 806

<210> SEQ ID NO 48
<211> LENGTH: 847
<212> TYPE: DNA
<213> ORGANISM: Artificial Sequence
<220> FEATURE:
<223> OTHER INFORMATION: Gam1-1-20-27F_H01.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (703)..(705)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t

<400> SEQUENCE: 48
tacnntgcag tcgagcggta gcacagggag cttgctcctg ggtgacgagc ggcggacggg 60
tgagtaatgt ctgggaaact gcctgatgga gggggataac tactggaaac ggtagctaat 120
accgcataac gtcgcaagac caaagagggg gaccttcggg cctcttgcca tcagatgtgc 180
ccagatggga ttagctagta ggtggggtaa tggctcacct aggcgacgat ccctagctgg 240
tctgagagga tgaccagcca cactggaact gagacacggt ccagactcct acgggaggca 300
gcagtgggga atattgcaca atgggcgcaa gcctgatgca gccatgccgc gtgtatgaag 360
aaggccttcg ggttgtaaag tactttcagc ggggaggaag gtgttgaggt taataacctc 420
agcaattgac gttacccgca gaagaagcac cggctaactc cgtgccagca gccgcggtaa 480
tacggagggt gcaagcgtta atcggaatta ctgggcgtaa agcgcacgca ggcggtctgt 540
caagtcggat gtgaaatccc cgggctcaac ctgggaactg cattcgaaac tggcaggcta 600
gagtcttgta gaggggggtg gaattcnggg tgtagcggtg aaatgcgtag agatctggag 660
gaataccggt ggcgaaggcg gccccctgga caaagactga cgnnncngtg cgaaagcgtg 720
gggagcaaac aggattagat accctggnag tccacgccgt aaacgatgtc gacttggagg 780
ttgtgccctt gaggcgtggc ttccgggagc taacgcgtta agtcgaccgg cctgggggga 840
gtacggg 847

<210> SEQ ID NO 49
<211> LENGTH: 851
<212> TYPE: DNA
<213> ORGANISM: Artificial Sequence
<220> FEATURE:
<223> OTHER INFORMATION: Gam1-1-21-27F_H02.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (602)..(604)
<223> OTHER INFORMATION: n is a, c, g, or t -continued
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (710)..(712)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (838)..(839)
<223> OTHER INFORMATION: n is a, c, g, or t
<220> FEATURE:
<221> NAME/KEY: misc_feature
<222> LOCATION: (844)..(844)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t

<400> SEQUENCE: 49
tacnntgcag tcgagcggta acacagggag cttgctcctg ggtgacgagc ggcggacggg 60
tgagtaatgt ctgggaaact gcctgatgga gggggataac tactggaaac ggtagctaat 120
accgcataac gtcgcaagac caaagagggg gaccttcggg cctcttgcca tcagatgtgc 180
ccagatggga ttagctagta ggtggggtaa cggctcacct aggcgacgat ccctagctgg 240
tctgagagga tgaccagcca cactggaact gagacacggt ccagactcct acgggaggca 300
gcagtgggga atattgcaca atgggcgcaa gcctgatgca gccatgccgc gtgtatgaag 360
aaggccttcg ggttgtaaag tactttcagc ggggaggaag gtgttgaggt taataacctc 420
agcaattgac gttacccgca gaagaagcac cggctaactc cgtgccagca gccgcggtaa 480
tacggagggt gcaagcgtta atcggaatta ctgggcgtaa agcgcacgca ggcggtctgt 540
caagtcggat gtgaaatccc cgggctcaac ctgggaactg cattcgaaac tggcaggcta 600
annntcttng aagagggggg gtaaaatttc cgggtgtagc ggtgaaatgc gtagagatct 660
ggaggaatac cggtggcgaa ngcggccccc tggacaaaga ctgacgctcn nngngcgaaa 720
gcgtggggag caaacaggat tagataccct ggtagtccac gccgtaacga tgtcgacttg 780
gagtntgccc ttgagcgtgn ttccggagct aacgngttaa gtcgaccgnc ctggggganna 840 cggncngcaa g 851

<210> SEQ ID NO 50

<211> LENGTH: 880
<212> TYPE: DNA
<213> ORGANISM: Artificial Sequence
<220> FEATURE:
<223> OTHER INFORMATION: Gam1-1-22-27F_H03.ab1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (604)..(604)
<223> OTHER INFORMATION: n is a, c, g, or t
<220> FEATURE:
<221> NAME/KEY: misc_feature
<222> LOCATION: (651)..(654)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t

<400> SEQUENCE: 50

```
gctacncatg caagtcgaac ggtagcacag aggagcttgc tccttgggtg acgagtggcg     60

gacgggtgag taatgtctgg gaaactgccc gatggagggg gataactact ggaaacggta    120

gctaataccg cataacgtcg caagaccaaa gagggggacc ttcgggcctc ttgccatcgg    180

atgtgcccag atgggattag ctagtaggtg gggtaacggc tcacctaggc gacgatccct    240

agctggtctg agaggatgac cagccacact ggaactgaga cacggtccag actcctacgg    300

gaggcagcag tggggaatat tgcacaatgg gcgcaagcct gatgcagcca tgccgcgtgt    360

atgaagaagg ccttcgggtt gtaaagtact ttcagcgggg aggaaggcga taaggttaat    420

aaccttgtcg attgacgtta cccgcagaag aagcaccggc taactccgtg ccagcagccg    480

cggtaatacg gagggtgcaa gcgttaatcg gaattactgg gcgtaaagcg cacgcaggcg    540

gtctgtcaag tcggatgtga aatccccggg ctcaacctgg gaactgcatt cganagnggc    600

nggntaagag ctcttgtaga ggggggtaga attccaggtg tagcgctgaa nnnncgtaga    660

gatctggagg aataccggtg gcgaaggcgg ccccctggac aaagactgac gctcangtgc    720

gaaagcgtgg ggagcaatca ggattagata ccctggtagt ccacgccgta aacgatgtcg    780

acttggagtt gtgcccttga ggcgtggctt ccgnagctaa cgcgttaagt cgaccgcctg    840

ggggagtacg gcngcaaggt taaaacntca aatgaatttg                          880
```

<210> SEQ ID NO 51
<211> LENGTH: 921
<212> TYPE: DNA
<213> ORGANISM: Artificial Sequence
<220> FEATURE:
<223> OTHER INFORMATION: Gam1-1-2-27F_C02.ab1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (589)..(596)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (616)..(619)
<223> OTHER INFORMATION: n is a, c, g, or t
<220> FEATURE:
<221> NAME/KEY: misc_feature
<222> LOCATION: (728)..(729)
<223> OTHER INFORMATION: n is a, c, g, or t
<220> FEATURE:
<221> NAME/KEY: misc_feature
<222> LOCATION: (804)..(805)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (823)..(825)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (843)..(847)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (863)..(864)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t
<220> FEATURE:

<221> NAME/KEY: misc_feature
<222> LOCATION: (892)..(892)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (901)..(905)
<223> OTHER INFORMATION: n is a, c, g, or t
<220> FEATURE:
<221> NAME/KEY: misc_feature
<222> LOCATION: (907)..(908)
<223> OTHER INFORMATION: n is a, c, g, or t
<220> FEATURE:
<221> NAME/KEY: misc_feature
<222> LOCATION: (912)..(914)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t

<400> SEQUENCE: 51
ctncnntgca agtcgagcgg cagcgggaaa gtagcttgct acttttgccg gcgagcggcg 60
gacgggtgag taatgtctgg gaaactgcct gatggagggg gataactact ggaaacggta 120
gctaataccg cataacgtcg caagaccaaa gagggggacc ttcgggcctc ttgccatcag 180
atgtgcccag atgggattag ctagtaggtg gggtaacggc tcacctaggc gacgatccct 240
agctggtctg agaggatgac cagccacact ggaactgaga cacggtccag actcctacgg 300
gaggcagcag tggggaatat tgcacaatgg gcgcaagcct gatgcagcca tgccgcgtgt 360
atgaagaagg ccttcgggtt gtaaagtact ttcagcgggg aggaaggtgt tgaggttaat 420
aacctcagca attgacgtta cccgcagaag aagcaccggc taactccgtg ccagcagccg 480
cggtaatacg gagggtgcaa gcgttaatcg gaattactgg gcgtaaagcg cacgcaggcg 540
gtctgtcaag tcggatgtga aatccccggg ctcaacctgg gaactgctnn nnnnnngtgg 600
caggctagan tcttgnnnng gggggtagaa ttccaggtgt agcggtgaaa tgcgtagaga 660
tctggaggaa taccggtggg aaaggcggcc ccctggacaa agactgacgc tcacgtgcga 720
aagcgtgnng agcaaacagg attagatacc ctggtagtcc acgccgtaaa cgatgtcgac 780
ttggaaggtt gtgcccttga ggcnnggctt cngcagctaa ctnnntcant tcanatcgac 840
tgnnnnnggt nagtacggnc gcnnagntta naaactcaaa ttgaantgga cngngggccc 900
nnnnnanncg gnnnggancc a 921

<210> SEQ ID NO 52
<211> LENGTH: 900
<212> TYPE: DNA
<213> ORGANISM: Artificial Sequence
<220> FEATURE:
<223> OTHER INFORMATION: Gam1-1-24-27F_H05.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (754)..(758)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t

<400> SEQUENCE: 52
gctanncntg cagtcgagcg gcagcgggaa agtagcttgc tacttttgcc ggcgagcggc 60
ggacgggtga gtaatgcctg ggatctgcc cagtcgaggg ggataactac tggaaacggt 120
agctaatacc gcatgcgccc tacgggggaa agcaggggac cttcgggcct tgcgcgattg 180
gatgaaccca ggtgggatta gctagttggt gaggtaacgg ctcaccaagg cgacgatccc 240
tagctggtct gagaggatga tcagccacac tggaactgag acacggtcca gactcctacg 300
ggaggcagca gtggggaata ttgcacaatg ggggaaaccc tgatgcagcc atgccgcgtg 360
tgtgaagaag gccttcgggt tgtaaagcac tttcagcgag gaggaaaggt cagtagctaa 420
tatctgctgg ctgtgacgtt actcgcagaa gaagcaccgg ctaactccgt gccagcagcc 480
gcggtaatac ggagggtgca agcgttaatc ggaattactg ggcgtaaagc gcacgcaggc 540
ggttggataa gttagatgtg aaagccccgg gctcaacctg ggaattgcat ttaaaactgt 600
ccagctagag tcttgtagag gggggtagaa ttccagggtg tagcggtgaa atgcgtagag 660
atctggagga ataccggtgg cgaaggcggc cccctggaca aagactgacg ctcngtgcga 720
aagcgtgggg agcaaacagg attagnatac cctnnnnntc caccnccgta aaccgatgtc 780
gatttgggag gctgtgtcct tgagacgtgg cttccggagc taacgncgtt aatcgacngc 840
ctggggggag tacggcngca agggttaaaa cttcaaatgn atttgaacgg ggggcccgcc 900

<210> SEQ ID NO 53
<211> LENGTH: 883
<212> TYPE: DNA
<213> ORGANISM: Artificial Sequence
<220> FEATURE:
<223> OTHER INFORMATION: Gam1-1-25-27F_H06.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:

<221> NAME/KEY: misc_feature
<222> LOCATION: (744)..(753)
<223> OTHER INFORMATION: n is a, c, g, or t
<220> FEATURE:
<221> NAME/KEY: misc_feature
<222> LOCATION: (755)..(759)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t

<400> SEQUENCE: 53
tacnntgcag tcgagcggca gcgggaaagt agcttgctac ttttgccggc gagcggcgga 60
cgggtgagta atgcctgggg atctgcccag tcgaggggga taactactgg aaacggtagc 120
taataccgca tgcgccctac gggggaaagc aggggacctt cgggccttgc gcgattggat 180
gaacccaggt gggattagct agttggtgag gtaacggctc accaaggcga cgatccctag 240
ctggtctgag aggatgatca gccacactgg aactgagaca cggtccagac tcctacggga 300
ggcagcagtg gggaatattg cacaatgggg gaaaccctga tgcagccatg ccgcgtgtgt 360
gaagaaggcc ttcgggttgt aaagcacttt cagcgaggag gaaaggttgg tagctaatat 420
ctgccagctg tgacgttact cgcagaagaa gcaccggcta actccgtgcc agcagccgcg 480
gtaatacgga gggtgcaagc gttaatcgga attactgggc gtaaagcgca cgcaggcggt 540
tggataagtt agatgtgaaa gccccgggct caacctggga attgcattta aaactgtcca 600
gctagagtct tgtagagggg ggtagaattc caggtgtagc ggtgaaatgc gtagagatct 660
ggaggaatac cggtggcgaa ngcggccccc tggacaaaga ctgacgctcn gtgcgaaagc 720
gtggggagca aacaggatta gaannnnnnn nnngnnnnnc gccgtaaacg atgtcgattt 780
ggaggctgtg tccttgagac gtggcttccg gagctaacgc gttaatcgac gcngggggag 840
tacggccgca gttaaactca aatgaaattg acgggggccc gcc 883

<210> SEQ ID NO 54
<211> LENGTH: 884
<212> TYPE: DNA
<213> ORGANISM: Artificial Sequence
<220> FEATURE:
<223> OTHER INFORMATION: Gam1-1-26-27F_H07.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (719)..(726)
<223> OTHER INFORMATION: n is a, c, g, or t
<220> FEATURE:
<221> NAME/KEY: misc_feature
<222> LOCATION: (728)..(740)
<223> OTHER INFORMATION: n is a, c, g, or t
<220> FEATURE:
<221> NAME/KEY: misc_feature
<222> LOCATION: (758)..(760)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (793)..(794)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t

```
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (829)..(830)
<223> OTHER INFORMATION: n is a, c, g, or t
<220> FEATURE:
<221> NAME/KEY: misc_feature
<222> LOCATION: (836)..(837)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (879)..(880)
<223> OTHER INFORMATION: n is a, c, g, or t

<400> SEQUENCE: 54

tacnntgcag tcgagcggta acacagggag cttgctcctg ggtgacgagc ggcggacggg      60

tgagtaatgt ctgggaaact gcctgatgga gggggataac tactggaaac ggtagctaat     120

accgcataac gtcgcaaaac caaagagggg gaccttcggg cctcttgcca tcagatgtgc     180

ccagatggga ttagctagta ggtggggtaa tggctcacct aggcgacgat ccctagctgg     240

tctgagagga tgaccagcca cactggaact gagacacggt ccagactcct acgggaggca     300

gcagtgggga atactgcaca atgggcgcaa gcctgatgca gccatgccgc gtgtatgaag     360

aaggccttcg ggttgtaaag tactttcagc ggggaggaag gtgttgaggt taataacctc     420

agcaattgac gttacccgca gaagaagcac cggctaactc cgtgccagca gccgcggtaa     480

tacggagggt gcaagcgtta atcggaatta ctgggcgtaa agcgcacgca ggcggtctgt     540

caagtcggat gtgaaatccc cgggctcaac ctgggaactg cattcgaaac tggcaggcta     600

gagtcttgta gaggggggta gaattccagg tgtagcggtg aaatgcgtag agatctggag     660

gaataccggt ggcgaaggcg gccccctgga caaagactga cgctcagtgc gaaagcgtnn     720

nnnnnnannn nnnnnnnnnn cctggtagtc cacgccgnnn aaacgaggtc gancttggag     780

ttgtgccctt ganngtggct tccggagcta acgcgtagtc gacncnggnn gtacgnncaa     840

gtaaactcaa angaattgac ggggcccgca caancgggnn ggga                      884


<210> SEQ ID NO 55
<211> LENGTH: 895
<212> TYPE: DNA
<213> ORGANISM: Artificial Sequence
<220> FEATURE:
<223> OTHER INFORMATION: Gam1-1-27-27F_H08.ab1
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (717)..(721)
```

<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t
<220> FEATURE:
<221> NAME/KEY: misc_feature
<222> LOCATION: (835)..(836)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (858)..(859)
<223> OTHER INFORMATION: n is a, c, g, or t
<220> FEATURE:
<221> NAME/KEY: misc_feature
<222> LOCATION: (872)..(873)
<223> OTHER INFORMATION: n is a, c, g, or t
<220> FEATURE:
<221> NAME/KEY: misc_feature
<222> LOCATION: (883)..(884)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t
<220> FEATURE:
<221> NAME/KEY: misc_feature
<222> LOCATION: (890)..(890)
<223> OTHER INFORMATION: n is a, c, g, or t
<220> FEATURE:
<221> NAME/KEY: misc_feature
<222> LOCATION: (893)..(893)
<223> OTHER INFORMATION: n is a, c, g, or t

<400> SEQUENCE: 55
taacncntgc agtcgagcgg taacacaggg agcttgctcc tgggtgacga gcggcggacg 60
ggtgagtaat gtctgggaaa ctgcctgatg gagggggata actactggaa acggtagcta 120
ataccgcata acgtcgcaag accaaagagg gggaccttcg ggcctcttgc catcagatgt 180
gcccagatgg gattagctag taggtggggt aacggctcac ctaggcgacg atccctagct 240
ggtctgagag gatgaccagc cacactggaa ctgagacacg gtccagactc ctacgggagg 300
cagcagtggg gaatattgca caatgggcgc aagcctgatg cagccatgcc gcgtgtatga 360
agaaggcctt cgggttgtaa agtactttca gcggggagga aggtgttgag gttaataacc 420
ttgtcaattg acgttacccg cagaagaagc accggctaac tccgtgccag cagccgcggt 480
aatacggagg gtgcaagcgt taatcggaat tactgggcgt aaagcgcacg caggcggtct 540
gtcaagtcgg atgtgaaatc cccgggctca acctgggaac tgcattcgaa actggcaggc 600
tagagtcttg tagagggggg tagaattcca ggtgtagcgg tgaaatgcgt agagatctgg 660
aggaataccg gtggcgaagg cggccccctg gacaaagact gacgctcngt gcgaaannnn 720
ngggagcaaa caggattaga taccctggna gtccacgccg taaacgatgt cgacttggag 780
gttgtgccct tgagcgtggc ttccggagct aacgcgttaa gtcgacgcng ggnanntncg 840
gccgcnnagg gttaaacnnc aatggaattg gnncgggggc cgnncncaan cgngg 895

<210> SEQ ID NO 56
<211> LENGTH: 882
<212> TYPE: DNA
<213> ORGANISM: Artificial Sequence
<220> FEATURE:
<223> OTHER INFORMATION: Gam1-1-28-27F_H09.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (699)..(703)
<223> OTHER INFORMATION: n is a, c, g, or t
<220> FEATURE:
<221> NAME/KEY: misc_feature
<222> LOCATION: (705)..(707)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (866)..(867)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t

<400> SEQUENCE: 56
gntacncatg caagtcgagc ggtaacacag ggagcttgct cctgggtgac gagcggcgga 60
cgggtgagta atgtctggga aactgcctga tggaggggga taactactgg aaacggtagc 120
taataccgca taacgtcgca agaccaaaga gggggacctt cgggcctctt gccatcagat 180
gtgcccagat gggattagct agtaggtggg gtaatggctc acctaggcga cgatccctag 240
ctggtctgag aggatgacca gccacactgg aactgagaca cggtccagac tcctacggga 300
ggcagcagtg gggaatattg cacaatgggc gcaagcctga tgcagccatg ccgcgtgtat 360
gaagaaggcc ttcgggttgt aaagtacttt cagcggggag gaaggcgata aggttaataa 420
ccttgtcgat tgacgttacc cgcagaagaa gcaccggcta actccgtgcc agcagccgcg 480
gtaatacgga gggtgcaagc gttaatcgga attactgggc gtaaagcgca cgcaggcggt 540
ctgtcaagtc ggacgtgaaa tccccgggct caacctggga actgcattcg aaactggcag 600
gctagagtct tgtagagggg ggtagaatcc caggtgtagc ggtgaaatgc gtagagatct 660
ggaggaatac cggtggcgaa ggcggccccc tggacaaann nnncnnntcn gtgcgaaagc 720
gtggggagca aacaggatta gataccctgg tagtccacgc cgtaaacgat gtcgatttgg 780

```
aggctgtgtc cttgagacgt ggcttccgga gctaacgcgt taaatcgacg cnggggggant    840

acggccgcaa ggttaancct caaatnnaat tgacggggnc cc                        882


<210> SEQ ID NO 57
<211> LENGTH: 938
<212> TYPE: DNA
<213> ORGANISM: Artificial Sequence
<220> FEATURE:
<223> OTHER INFORMATION: Gam1-1-29-27F_H10.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (602)..(603)
<223> OTHER INFORMATION: n is a, c, g, or t
<220> FEATURE:
<221> NAME/KEY: misc_feature
<222> LOCATION: (691)..(694)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (827)..(828)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (886)..(887)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (916)..(917)
<223> OTHER INFORMATION: n is a, c, g, or t
<220> FEATURE:
<221> NAME/KEY: misc_feature
<222> LOCATION: (919)..(920)
<223> OTHER INFORMATION: n is a, c, g, or t
<220> FEATURE:
<221> NAME/KEY: misc_feature
<222> LOCATION: (922)..(923)
<223> OTHER INFORMATION: n is a, c, g, or t
<220> FEATURE:
<221> NAME/KEY: misc_feature
<222> LOCATION: (926)..(927)
<223> OTHER INFORMATION: n is a, c, g, or t
<220> FEATURE:
<221> NAME/KEY: misc_feature
<222> LOCATION: (929)..(929)
<223> OTHER INFORMATION: n is a, c, g, or t
<220> FEATURE:
<221> NAME/KEY: misc_feature
<222> LOCATION: (934)..(935)
<223> OTHER INFORMATION: n is a, c, g, or t

<400> SEQUENCE: 57

tacnntgcag tcgagcggca gcgggaaagt agcttgctac ttttgccggc gagcggcgga     60

cgggtgagta atgcctgggg atctgcccaa tcgaggggga taactactgg aaacggtagc    120

taataccgca tacgccctac gggggaaagc aggggacctt cgggccttgc gcgattggat    180
```

gaacccaggt gggattagct agttggtgag gtaacggctc accaaggcga cgatccctag 240
ctggtctgag aggatgatca gccacactgg aactgagaca cggtccagac tcctacggga 300
ggcagcagtg gggaatattg cacaatgggg gaaaccctga tgcagccatg ccgcgtgtgt 360
gaagaaggcc ttcgggttgt aaagcacttt cagcgaggag gaaaggttgg tagctaatat 420
ctgccagctg tgacgttact cgcagaagaa gcaccggcta actccgtgcc agcagccgcg 480
gtaatacgga gggtgcaagc gttaatcgga attactgggc gtaaagcgca cgcaggcggt 540
tggataagtt agatgtgaaa gccccgggct caacctggga attgcattta aaactgtcca 600
gnnagagctc cttgtagagg gggggtaaga attccaggtg tagcggtgaa atgcgtagag 660
atctggagga atacccggtg gcgaaaggcg nnnncctgga caaagactga cgctcngtgc 720
gaaagcgtgg ggagcaaaca ggattagata ccctggtagt ccacgccgta aacgatgtcg 780
atttggaagg ctgtgtcctt gagacgtggc cttccggaag ctaaccnncg ttaaatcgac 840
cgccctgggg gagtacgggc cgccaagggt taaaanctcc aaaatnngaa attngaacgg 900
gggggcccnc ccaccnnann cnnggnngng gtgnnggc 938

<210> SEQ ID NO 58
<211> LENGTH: 866
<212> TYPE: DNA
<213> ORGANISM: Artificial Sequence
<220> FEATURE:
<223> OTHER INFORMATION: Gam1-1-30-27F_H11.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (691)..(692)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (785)..(786)
<223> OTHER INFORMATION: n is a, c, g, or t
<220> FEATURE:
<221> NAME/KEY: misc_feature
<222> LOCATION: (790)..(793)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (857)..(859)
<223> OTHER INFORMATION: n is a, c, g, or t

<400> SEQUENCE: 58
tacnntgcag tcgagcggta gcacaggaga gcttgctctc tgggtgacga gcggcggacg 60

-continued

```
ggtgagtaat gtctgggaaa ctgcctgatg gagggggata actactggaa acggtagcta    120

ataccgcata acgtcgcaag accaaagagg gggaccttcg ggcctcttgc catcagatgt    180

gcccagatgg gattagctag taggtggggt aacggctcac ctaggcgacg atccctagct    240

ggtctgagag gatgaccagc cacactggaa ctgagacacg gtccagactc ctacgggagg    300

cagcagtggg gaatattgca caatgggcgc aagcctgatg cagccatgcc gcgtgtatga    360

agaaggcctt cgggttgtaa agtactttca gcggggagga aggtgttgag gttaataacc    420

tcagcaattg acgttacccg cagaagaagc accggctaac tccgtgccag cagccgcggt    480

aatacggagg gtgcaagcgt taatcggaat tactgggcgt aaagcgcacg caggcggtcc    540

gtcaagtcgg atgtgaaatc cccgggctca acctgggaac tgcattcgaa actggcaggc    600

tagagtcttg tagagggggg tagaattcca ggtgtagcgg tgaaatgcgt agagatctgg    660

aggaatacng gtggcgaagg cggccccccg nncaaagact gacgctcngt gcgaaagcgt    720

gggggagcaa acaggattag ataccctggn agtccacgcc gtaaacgatg tcgacttgga    780

gttgnngccn nnngaggcgt gnttccgagc tacgcgttag tcgaccgcct gggggagtac    840

ggccgncaag gttaaannnt caaatt                                         866
```

```
<210> SEQ ID NO 59
<211> LENGTH: 792
<212> TYPE: DNA
<213> ORGANISM: Artificial Sequence
<220> FEATURE:
<223> OTHER INFORMATION: Gam1-1-32-27F_B01.ab1
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (697)..(705)
<223> OTHER INFORMATION: n is a, c, g, or t
<220> FEATURE:
<221> NAME/KEY: misc_feature
<222> LOCATION: (711)..(713)
<223> OTHER INFORMATION: n is a, c, g, or t
<220> FEATURE:
<221> NAME/KEY: misc_feature
<222> LOCATION: (789)..(790)
<223> OTHER INFORMATION: n is a, c, g, or t

<400> SEQUENCE: 59

tgcagtcgag cggtaacaca gggagcttgc tcctgggtga cgagcggcgg acgggtgagt     60

aatgtctggg aaactgcctg atggaggggg ataactactg gaaacggtag ctaataccgc    120

ataacgtcgc aagaccaaag agggggacct tcgggcctct tgccatcaga tgtgcccaga    180

tgggattagc tagtaggtgg ggtaatggct cacctaggcg acgatcccta gctggtctga    240

gaggatgacc agccacactg gaactgagac acggtccaga ctcctacggg aggcagcagt    300

ggggaatatt gcacaatggg cgcaagcctg atgcagccat gccgcgtgta tgaagaaggc    360

cttcgggttg taaagtactt tcagcgggga ggaaggcgat aaggttaata accttgtcga    420

ttgacgttac ccgcagaaga agcaccggct aactccgtgc cagcagccgc ggtaatacgg    480

agggtgcaag cgttaatcgg aattactggg cgtaaagcgc acgcaggcgg tctgtcaagt    540

cggatgtgaa atccccgggc tcaacctggg aactgcattc gaaactggca ggctagagtc    600

ttgtagaggg gggtagaatt ccaggtgtag cggtgaaatg cgtagagatc tggaggaata    660

ccggtggcga angcggcccc ctggacaaag actgacnnnn nnnnngcgaa nnncgtgggg    720

agcaaacagg attagatacc ctggtagtcc acgccgtaaa cgatgtcgac ttggaggttg    780
```

tgcccttgnn gg 792

<210> SEQ ID NO 60
<211> LENGTH: 792
<212> TYPE: DNA
<213> ORGANISM: Artificial Sequence
<220> FEATURE:
<223> OTHER INFORMATION: Gam1-1-3-27F_H02.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (729)..(731)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t

<400> SEQUENCE: 60
tgcnagtcga acggtagcac agaggagctt gctccttggg tgacgagtgg cggacgggtg 60
agtaatgtct gggaaactgc ccgatggagg gggataacta ctggaaacgg tagctaatac 120
cgcataacgt cgcaagacca aagaggggga ccttcgggcc tcttgccatc ggatgtgccc 180
agatgggatt agctagtagg tggggtaacg gctcacctag gcgacgatcc ctagctggtc 240
tgagaggatg accagccaca ctggaactga gacacggtcc agactcctac gggaggcagc 300
agtggggaat attgcacaat gggcgcaagc ctgatgcagc catgccgcgt gtatgaagaa 360
ggccttcggg ttgtaaagta ctttcagcgg ggaggaaggc gataaggtta ataaccttgt 420
cgattgacgt tacccgcaga agaagcaccg gctaactccg tgccagcagc cgcggtaata 480
cggagggtgc aagcgttaat cggaattact gggcgtaaag cgcacgcagg cggtctgtca 540
agtcggatgt gaaatccccg ggctcaacct gggaactgca ttcgaaactg gcaggctaga 600
gtcttgtaga ggggggtaga attccaggtg tagcggtgaa atgcgtagag atctggagga 660
ataccggtgg cgaangcggc cccctggaca aagactgacg ctcnggngcg aaagcgtggg 720
gagcaatcnn nantagatac cctggtagtc cacgccgtaa acgatgtcga cttggaggtt 780
gtgcccttna gg 792

<210> SEQ ID NO 61
<211> LENGTH: 828
<212> TYPE: DNA
<213> ORGANISM: Artificial Sequence
<220> FEATURE:
<223> OTHER INFORMATION: Gam1-1-33-27F_B02.ab1
<220> FEATURE:
<221> NAME/KEY: misc_feature
<222> LOCATION: (3)..(5)

<223> OTHER INFORMATION: n is a, c, g, or t
<220> FEATURE:
<221> NAME/KEY: misc_feature
<222> LOCATION: (701)..(703)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (771)..(775)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (787)..(789)
<223> OTHER INFORMATION: n is a, c, g, or t
<220> FEATURE:
<221> NAME/KEY: misc_feature
<222> LOCATION: (791)..(794)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (824)..(825)
<223> OTHER INFORMATION: n is a, c, g, or t

<400> SEQUENCE: 61
tgnnntcgag cggtaacaca gggagcttgc tcctgggtga cgagcggcgg acgggtgagt 60
aatgtctggg aaactgcctg atggaggggg ataactactg gaaacggtag ctaataccgc 120
ataacgtcgc aagaccaaag agggggacct tcgggcctct tgccatcaga tgtgcccaga 180
tgggattagc tagtaggtgg ggtaacggct cacctaggcg acgatcccta gctggtctga 240
gaggatgacc agccacactg gaactgagac acggtccaga ctcctacggg aggcagcagt 300
ggggaatatt gcacaatggg cgcaagcctg atgcagccat gccgcgtgta tgaagaaggc 360
cttcgggttg taaagtactt tcagcgggga ggaaggtgtt gaggttaata acctcagcaa 420
ttgacgttac ccgcagaaga agcaccggct aactccgtgc cagcagccgc ggtaatacgg 480

```
agggtgcaag cgttaatcgg aattactggg cgtaaagcgc acgcaggcgg tctgtcaagt    540

cggatgtgaa atccccgggc tcaacctggg aactgcattc gaaactggca ggctagagtc    600

ttgtagaggg gggtagaatt ccaggtgtag cggtgaaatg cgtagagatc tggaggaata    660

ccggtggcga aggcggcccc ctggacaaag actgacgctc nnntgcgaaa gcgtggggag    720

caaacaggat tagataccct ggnagtccac gccgtaancg atgtcgactt nnnnntngtg    780

cccttgnnng nnnntccgna nctaacgcnt tnagtcnanc gncnnggg                 828
```

```
<210> SEQ ID NO 62
<211> LENGTH: 755
<212> TYPE: DNA
<213> ORGANISM: Artificial Sequence
<220> FEATURE:
<223> OTHER INFORMATION: Gam1-1-35-27F_B04.ab1
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (671)..(673)
<223> OTHER INFORMATION: n is a, c, g, or t
<220> FEATURE:
<221> NAME/KEY: misc_feature
<222> LOCATION: (683)..(686)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (700)..(702)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (717)..(718)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (750)..(751)
```

<223> OTHER INFORMATION: n is a, c, g, or t

<400> SEQUENCE: 62
gcnngtcgag cggtaacaca gggagcttgc tcctgggtga cgagcggcgg acgggtgagt 60
aatgtctggg aaactgcctg atggaggggg ataactactg gaaacggtag ctaataccgc 120
ataacgtcgc aagaccaaag agggggacct tcgggcctct tgccatcaga tgtgcccaga 180
tgggattagc tagtaggtgg ggtaatggct cacctaggcg acgatcccta gctggtctga 240
gaggatgacc agccacactg gaactgagac acggtccaga ctcctacggg aggcagcagt 300
ggggaatatt gcacaatggg cgcaagcctg atgcagccat gccgcgtgta tgaagaaggc 360
cttcgggttg taaagtactt tcagcgggga ggaaggcgat aaggttaata accttgtcga 420
ttgacgttac ccgcagaaga agcaccggct aactccgtgc cagcagccgc ggtaatacgg 480
agggtgcaag cgttaatcgg aattactggg cgtaaagcgc acgcaggcgg ttggataagt 540
tagatgtgaa agccccgggc tcaacctggg aactgcattc gaaactggca ggctagagtc 600
ttgtagaggg gggtagaatt ccaggtgtag cggtgaaatg cgtagagatc tggaggaata 660
ccggtggcga nnnggccccc tgnnnnaana ctgacgctcn nntgcnaaag cgtgggnngn 720
ancnggatta gataccctgn tantcncncn naaac 755

<210> SEQ ID NO 63
<211> LENGTH: 780
<212> TYPE: DNA
<213> ORGANISM: Artificial Sequence
<220> FEATURE:
<223> OTHER INFORMATION: Gam1-1-36-27F_B05.ab1
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (774)..(778)
<223> OTHER INFORMATION: n is a, c, g, or t

<400> SEQUENCE: 63
agtcgagcgg tagcacaggg agcttgctcc tgggtgacga gcggcggacg ggtgagtaat 60
gtctgggaaa ctgcctgatg gagggggata actactggaa acggtagcta ataccgcata 120
acgtcgcaag accaaagagg gggaccttcg ggcctcttgc catcagatgt gcccagatgg 180
gattagctag taggtggggt aatggctcac ctagacgacg atccctagct ggtctgagag 240
gatgaccagc cacactggaa ctgagacacg gtccagactc ctacgggagg cagcagtggg 300
gaatattgca caatgggcgc aagcctgatg cagccatgcc gcgtgtatga agaaggcctt 360
cgggttgtaa agtactttca gcggggagga aggtgttgag gttaataacc tcagcaattg 420
acgttacccg cagaagaagc accggctaac tccgtgccag cagccgcggt aatacggagg 480
gtgcaagcgt taatcggaat tactgggcgt aaagcgcacg caggcggtct gtcaagtcgg 540
atgtgaaatc cccgggctca acctgggaac tgcattcgaa actggcaggc tagagtcttg 600
tagagggggg tagaattcca ggtgtagcgg tgaaatgcgt agagatctgg aggaataccg 660
gtgncgaang cggccccctg gacaaagact gacgctcagg tgcnnaagcg tggggagcaa 720
acaggantag ataccctggt agtccacgcc gtaaacgatg tcnacttgga ggtnnnnncc 780

<210> SEQ ID NO 64
<211> LENGTH: 854
<212> TYPE: DNA
<213> ORGANISM: Artificial Sequence
<220> FEATURE:
<223> OTHER INFORMATION: Gam1-1-37-27F_B06.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (702)..(704)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (758)..(759)
<223> OTHER INFORMATION: n is a, c, g, or t
<220> FEATURE:
<221> NAME/KEY: misc_feature
<222> LOCATION: (767)..(767)
<223> OTHER INFORMATION: n is a, c, g, or t
<220> FEATURE:
<221> NAME/KEY: misc_feature
<222> LOCATION: (772)..(775)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (788)..(789)
<223> OTHER INFORMATION: n is a, c, g, or t
<220> FEATURE:
<221> NAME/KEY: misc_feature
<222> LOCATION: (792)..(794)
<223> OTHER INFORMATION: n is a, c, g, or t
<220> FEATURE:
<221> NAME/KEY: misc_feature
<222> LOCATION: (797)..(798)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:

<221> NAME/KEY: misc_feature
<222> LOCATION: (819)..(820)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (827)..(829)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (838)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (852)..(853)
<223> OTHER INFORMATION: n is a, c, g, or t

<400> SEQUENCE: 64

```
tgcnngtcga gcggtaacac agggagcttg ctcctgggtg acgagcggcg gacgggtgag     60

taatgtctgg gaaactgcct gatggagggg gataactact ggaaacggta gctaataccg    120

cataacgtcg caagaccaaa gagggggacc ttcgggcctc ttgccatcag atgtgcccag    180

atgggattag ctagtaggtg gggtaatggc tcacctaggc gacgatccct agctggtctg    240

agaggatgac cagccacact ggaactgaga cacggtccag actcctacgg gaggcagcag    300

tggggaatat tgcacaatgg gcgcaagcct gatgcagcca tgccgcgtgt atgaagaagg    360

ccttcgggtt gtaaagtact ttcagcgggg aggaaggcga taaggttaat aaccttgtcg    420

attgacgtta cccgcagaag aagcaccggc taactccgtg ccagcagccg cggtaatacg    480

gagggtgcaa gcgttaatcg gaattactgg gcgtaaagcg cacgcaggcg gtctgtcaag    540

tcggatgtga aatccccggg ctcaacctgg gaactgcatt cgaaactggc aggctagagt    600

cttgtagagg ggggtagaat tccaggtgta gcggtggaat gcgtagagat ctggaggaat    660

accggtggcg aangcggccc cctggacaaa gactgacgct cnnngtgcga aagcgtgggg    720

agcaaacagg antanatacc ctggtagtcc acgccgtnnc gatgtcnact tnnnnttgng    780

cccntganng tnnntcnnan ctaacgcgtt aagtcnacnn cnggggnnna cggncgcnnn    840

gtnaaactcn anng                                                      854
```

<210> SEQ ID NO 65
<211> LENGTH: 830
<212> TYPE: DNA
<213> ORGANISM: Artificial Sequence
<220> FEATURE:
<223> OTHER INFORMATION: Gam1-1-38-27F_B07.ab1
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (648)..(665)
<223> OTHER INFORMATION: n is a, c, g, or t
<220> FEATURE:
<221> NAME/KEY: misc_feature
<222> LOCATION: (668)..(670)
<223> OTHER INFORMATION: n is a, c, g, or t
<220> FEATURE:
<221> NAME/KEY: misc_feature
<222> LOCATION: (675)..(688)
<223> OTHER INFORMATION: n is a, c, g, or t
<220> FEATURE:
<221> NAME/KEY: misc_feature
<222> LOCATION: (690)..(692)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (769)..(772)
<223> OTHER INFORMATION: n is a, c, g, or t
<220> FEATURE:
<221> NAME/KEY: misc_feature
<222> LOCATION: (790)..(791)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (806)..(809)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (825)..(827)
<223> OTHER INFORMATION: n is a, c, g, or t

<400> SEQUENCE: 65
tgnnnntcga gcggtaacac agggagcttg ctcctgggtg acgagcggcg gacgggtgag 60
taatgtctgg gaaactgcct gatggagggg gataactact ggaaacggta gctaataccg 120
cataacgtcg caagaccaaa gagggggacc ttcgggcctc ttgccatcag atgtgcccag 180
atgggattag ctagtaggtg gggtaacggc tcacctaggc gacgatccct agctggtctg 240
agaggatgac cagccacact ggaactgaga cacggtccag actcctacgg gaggcagcag 300
tggggaatat tgcacaatgg gcgcaagcct gatgcagcca tgccgcgtgt atgaagaagg 360
ccttcgggct gtaaagtact ttcagcgggg aggaaggcga taaggttaat aaccttgtcg 420
attgacgtta cccgcagaag aagcaccggc taactccgtg ccagcagccg cggtaatacg 480
gagggtgcaa gcgttaatcg gaattactgg gcgtaaagcg cacgcaggcg gtctgtcaag 540
tcggatgtga aatccccggg ctcaacctgg gaactgcatt cgaaactggc aggctagagt 600
cttgtagagg ggggtagaat tccaggtgta gcggtgaaat gcgtagannn nnnnnnnnnn 660
nnnnnccnnn ccccnnnnnn nnnnnnnnan nngacgctca ngtgcgaaag cgtggggagc 720
aaacaggatt agataccctg gtagtccacg ccgtancgat gtcnacttnn nngttgtgcc 780
cttgaggcgn ngnttcnggn anctannnng ttaagtcnac cgccnnnggg 830

<210> SEQ ID NO 66
<211> LENGTH: 703
<212> TYPE: DNA
<213> ORGANISM: Artificial Sequence
<220> FEATURE:
<223> OTHER INFORMATION: Gam1-1-39-27F_B08.ab1
<220> FEATURE:
<221> NAME/KEY: misc_feature
<222> LOCATION: (23)..(28)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t

<400> SEQUENCE: 66
gcaagtcgag cggtagcaca ggnnnnnntg ctctctgggt gacgagcggc ggacgggtga 60
gtaatgtctg ggaaactgcc tgatggaggg ggataactac tggaaacggt agctaatacc 120
gcataacgtc gcaagaccaa agagggggac cttcgggcct cttgccatca gatgtgccca 180
gatgggatta gctagtaggt ggggtaacgg ctcacctagg cgacgatccc tagctggtct 240
gagaggatga ccagccacac tggaactgag acacggtcca gactcctacg ggaggcagca 300
gtggggaata ttgcacaatg ggcgcaagcc tgatgcagcc atgccgcgtg tatgaagaag 360
gccttcgggt tgtaaagtac tttcagcggg gaggaaggtg ttgaggttaa taacctcagc 420
aattgacgtt acccgcagaa gaagcaccgg ctaactccgt gccagcagcc gcggtaatac 480
ggagggtgca agcgttaatc ggaattactg ggcgtaaagc gcacgcaggc ggtctgtcaa 540
gtcggatgtg aaatccccgg gctcaacctg ggaactgcat tcgaaactgg caggctagag 600
tcttgtagag gggggtagaa ttccaggtgt agcggtgaaa tgcgtagaga tctggaggaa 660
taccggtggc gaangngggc cccctggaca aagactgacg ctc 703

<210> SEQ ID NO 67
<211> LENGTH: 777
<212> TYPE: DNA
<213> ORGANISM: Artificial Sequence
<220> FEATURE:
<223> OTHER INFORMATION: Gam1-1-40-27F_B09.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (700)..(702)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (706)..(707)
<223> OTHER INFORMATION: n is a, c, g, or t
<220> FEATURE:
<221> NAME/KEY: misc_feature
<222> LOCATION: (729)..(732)
<223> OTHER INFORMATION: n is a, c, g, or t
<220> FEATURE:
<221> NAME/KEY: misc_feature
<222> LOCATION: (734)..(736)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (754)..(756)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (775)..(776)
<223> OTHER INFORMATION: n is a, c, g, or t

<400> SEQUENCE: 67
caagtcnngn ggtagcacag ggagcttgct cctgggtgac gagcggcgga cgggtgagta 60
atgtctggga aactgcctga tggaggggga taactactgg aaacggtagc taataccgca 120
taacgtcgca agaccaaaga gggggacctt cgggcctctt gccatcagat gtgcccagat 180
gggattagct agtaggtggg gtaatggctc acctagacga cgatccctag ctggtctgag 240
aggatgacca gccacactgg aactgagaca cggtccagac tcctacggga ggcagcagtg 300
gggaatattg cacaatgggc gcaagcctga tgcagccatg ccgcgtgtat gaagaaggcc 360
ttcgggttgt aaagtacttt cagcggggag gaaggtgttg aggttaataa cctcagcaat 420
tgacgttacc cgcagaagaa gcaccggcta actccgtgcc agcagccgcg gtaatacgga 480
gggtgcaagc gttaatcgga attactgggc gtaaagcgca cgcaggcggt ctgtcaagtc 540
ggatgtgaaa tccccgggct caacctggga actgcattcg aaactggcag gctagagtct 600
tgtagagggg ggtagaattc caggtgtagc ggtgaaatgc gtagagatct ggaggaatac 660
cggtggcgaa ggcggccccc tggacaaaga ctgacgctcn nngncnnaag cgtggggagc 720
aaacaggann nnannncctg gtantccacg ccgnnnacga tgtcnacttg gaggnng 777

<210> SEQ ID NO 68
<211> LENGTH: 895
<212> TYPE: DNA
<213> ORGANISM: Artificial Sequence
<220> FEATURE:
<223> OTHER INFORMATION: Gam1-1-4-27F_C04.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:

-continued

<221> NAME/KEY: misc_feature
<222> LOCATION: (613)..(614)
<223> OTHER INFORMATION: n is a, c, g, or t
<220> FEATURE:
<221> NAME/KEY: misc_feature
<222> LOCATION: (691)..(692)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (703)..(705)
<223> OTHER INFORMATION: n is a, c, g, or t
<220> FEATURE:
<221> NAME/KEY: misc_feature
<222> LOCATION: (771)..(776)
<223> OTHER INFORMATION: n is a, c, g, or t
<220> FEATURE:
<221> NAME/KEY: misc_feature
<222> LOCATION: (781)..(784)
<223> OTHER INFORMATION: n is a, c, g, or t
<220> FEATURE:
<221> NAME/KEY: misc_feature
<222> LOCATION: (787)..(790)
<223> OTHER INFORMATION: n is a, c, g, or t
<220> FEATURE:
<221> NAME/KEY: misc_feature
<222> LOCATION: (793)..(794)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (814)..(821)
<223> OTHER INFORMATION: n is a, c, g, or t
<220> FEATURE:
<221> NAME/KEY: misc_feature
<222> LOCATION: (828)..(830)
<223> OTHER INFORMATION: n is a, c, g, or t
<220> FEATURE:
<221> NAME/KEY: misc_feature
<222> LOCATION: (843)..(845)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (855)..(856)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t
<220> FEATURE:
<221> NAME/KEY: misc_feature
<222> LOCATION: (878)..(879)
<223> OTHER INFORMATION: n is a, c, g, or t
<220> FEATURE:
<221> NAME/KEY: misc_feature
<222> LOCATION: (887)..(887)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t

<400> SEQUENCE: 68
tacnntgcaa gtcgagcggt agcacaggag agcttgctct ctgggtgacg agcggcggac 60
gggtgagtaa tgtctgggaa actgcctgat ggagggggat aactactgga aacggtagct 120
aataccgcat aacgtcgcaa gaccaaagag ggggaccttc gggcctcttg ccatcagatg 180
tgcccagatg ggattagcta gtaggtgggg taacggctca cctaggcgac gatccctagc 240
tggtctgaga ggatgaccag ccacactgga actgagacac ggtccagact cctacgggag 300
gcagcagtgg ggaatattgc acaatggggg aaaccctgat gcagccatgc cgcgtgtgtg 360
aagaaggcct tcgggttgta aagcactttc agcgaggagg aaaggttggt agctaatatc 420
tgccagctgt gacgttactc gcagaagaag caccggctaa ctccgtgcca gcagccgcgg 480
taatacggag ggtgcaagcg ttaatcggaa ttactgggcg taaagcgcac gcaggcggtt 540
ggataagtta gatgtgaaag ccccgggctc aacctgggaa ttgcatttaa aactgtccag 600
ctagantcna gannggggggg ggtagattcc aggtgtagcg gtgaaatgcg tagagatctg 660
gaggaatacc ggtggcgaag gcggcccccct nngnaanaaa nannngacgc tcaggcgcga 720
aagcgtgggg agcaaacagg attagatacc ctggtagtcc acgccgtaaa nnnnnngtct 780
nnnnttnnnn ggnnggctgt gtcntgagac gtcnnnnnnn nctacgcnnn aatcgaacgc 840
tgnnntacgn gcagnnaaan tnaatganga cggggccnnc acagcgngga ncatg 895

<210> SEQ ID NO 69
<211> LENGTH: 925
<212> TYPE: DNA
<213> ORGANISM: Artificial Sequence
<220> FEATURE:
<223> OTHER INFORMATION: Gam1-1-5-27F_C05.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (703)..(703)

<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (772)..(773)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (799)..(800)
<223> OTHER INFORMATION: n is a, c, g, or t
<220> FEATURE:
<221> NAME/KEY: misc_feature
<222> LOCATION: (805)..(806)
<223> OTHER INFORMATION: n is a, c, g, or t
<220> FEATURE:
<221> NAME/KEY: misc_feature
<222> LOCATION: (823)..(823)
<223> OTHER INFORMATION: n is a, c, g, or t
<220> FEATURE:
<221> NAME/KEY: misc_feature
<222> LOCATION: (825)..(826)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t
<220> FEATURE:
<221> NAME/KEY: misc_feature
<222> LOCATION: (847)..(848)
<223> OTHER INFORMATION: n is a, c, g, or t
<220> FEATURE:
<221> NAME/KEY: misc_feature
<222> LOCATION: (850)..(851)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (872)..(872)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (892)..(892)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (910)..(910)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t

<400> SEQUENCE: 69

```
gcctacnntg caagtcgagc ggtagcacag ggagcttgct cctgggtgac gagcggcgga     60

cgggtgagta atgtctggga aactgcctga tggaggggga taactactgg aaacggtagc    120

taataccgca taacgtcgca agaccaaaga gggggacctt cgggcctctt gccatcagat    180

gtgcccagat gggattagct agtaggtggg gtaatggctc acctaggcga cgatccctag    240

ctggtctgag aggatgacca gccacactgg aactgagaca cggtccagac ttctacggga    300

ggcagcagtg gggaatattg cacaatgggc gcaagcctga tgcagccatg ccgcgtgtat    360

gaagaaggcc ttcgggttgt aaagtacttt cagcggggag gaaggtgttg aggttaataa    420

cctcagcaat tgacgttacc cgcagaagaa gcaccggcta actccgtgcc agcagccgcg    480

gtaatacgga gggtgcaagc gttaatcgga attactgggc gtaaagcgca cgcaggcggt    540

ctgtcaagtc ggatgtgaaa tccccgggct caacctggga actgcattcg aaactggcag    600

ccnananttc ttgnagaggg gggtagnant ccaggtgtag cggtgaaatg cgtagagatc    660

tggaggaata ccggtggcga aggcggcccc ctggacaaaa acnganctcn tcnggtgcga    720

aagcgtgggg agcaaacagg attagatacc ctggtagtcc acgccgtaaa cnnatgtcga    780

cttggangtt gngcccttnn aggcnnggct tccggaagct aancnncgtt aagttcgacc    840

gnccggnngn ngtacgtncn gccagcnatg gntacaaact tcanaatgaa tnggangggg    900

cggcccgncn caagggcggn tgggg                                          925
```

<210> SEQ ID NO 70
<211> LENGTH: 900
<212> TYPE: DNA
<213> ORGANISM: Artificial Sequence
<220> FEATURE:
<223> OTHER INFORMATION: Gam1-1-6-27F_C06.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (728)..(737)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (744)..(746)
<223> OTHER INFORMATION: n is a, c, g, or t
<220> FEATURE:
<221> NAME/KEY: misc_feature
<222> LOCATION: (748)..(749)

<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (803)..(804)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (814)..(815)
<223> OTHER INFORMATION: n is a, c, g, or t
<220> FEATURE:
<221> NAME/KEY: misc_feature
<222> LOCATION: (837)..(839)
<223> OTHER INFORMATION: n is a, c, g, or t
<220> FEATURE:
<221> NAME/KEY: misc_feature
<222> LOCATION: (841)..(844)
<223> OTHER INFORMATION: n is a, c, g, or t
<220> FEATURE:
<221> NAME/KEY: misc_feature
<222> LOCATION: (847)..(850)
<223> OTHER INFORMATION: n is a, c, g, or t
<220> FEATURE:
<221> NAME/KEY: misc_feature
<222> LOCATION: (854)..(855)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (881)..(882)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t

<400> SEQUENCE: 70
gcctacnntg caagtcgagc ggtaacacag ggagcttgct cctgggtgac gagcggcgga 60
cgggtgagta acgtctggga aactgcctga tggaggggga taactactgg aaacggtagc 120
taataccgca taacgtcgca agaccaaaga gggggacctt cgggcctctt gccatcagat 180
gtgcccagat gggattagct agtaggtggg gtaacggctc acctaggcga cgatccctag 240
ctggtctgag aggatgacca gccacactgg aactgagaca cggtccagac tcctacggga 300
ggcagcagtg gggaatattg cacaatgggc gcaagcctga tgcagccatg ccgcgtgtat 360
gaagaaggcc ttcgggttgt aaagtacttt cagcggggag gaaggtgttg aggttaataa 420
cctcagcaat tgacgttacc cgcagaagaa gcaccggcta actccgtgcc agcagccgcg 480
gtaatacgga gggtgcaagc gttaatcgga attactgggc gtaaagcgca cgcaggcggt 540
ctgtcaagtc ggatgtgaaa tccccgggct caacctggga actgcattcg aaactggcag 600
gctagagtct tgtagagggg ggtagaattc caggtgtagc ggtgaaatgc gtagagatct 660
ggaggaatac cggtggcgaa ggcggccccc tggacaaaga ctgacgctca ngtgcgaaag 720
cgtggggnnn nnnnnnntta ancnnncnnt ggtncnccac nccnataaca cgnatgtcga 780
cttggaaggt tgtgcccntg agnngtgntt tccnnagcta acgcgtttaa gtcgacnnng 840
nnnntannnn gcannaaact caatgattga nggggcccgc nncaancngg nggnancatg 900

<210> SEQ ID NO 71
<211> LENGTH: 892
<212> TYPE: DNA
<213> ORGANISM: Artificial Sequence
<220> FEATURE:
<223> OTHER INFORMATION: Gam1-1-7-27F_C07.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (673)..(675)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (800)..(801)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (878)..(880)
<223> OTHER INFORMATION: n is a, c, g, or t
<220> FEATURE:

<221> NAME/KEY: misc_feature
<222> LOCATION: (888)..(888)
<223> OTHER INFORMATION: n is a, c, g, or t

<400> SEQUENCE: 71

```
ctannatgca agtcgagcgg taacacaggg agcttgctcc tgggtgacga gcggcggacg     60

ggtgagtaat gtctgggaaa ctgcctgatg gagggggata actactggaa acggtagcta    120

ataccgcata acgtcgcaag accaaagagg gggaccttcg ggcctcttgc catcagatgt    180

gcccagatgg gattagctag taggtggggt aacggctcac ctaggcgacg atccctagct    240

ggtctgagag gatgaccagc cacactggaa ctgagacacg gtccagactc ctacgggagg    300

cagcagtggg gaatattgca caatgggcgc aagcctgatg cagccatgcc gcgtgtatga    360

agaaggcctt cgggttgtaa agtactttca gcggggagga aggcgataag gttaataacc    420

ttgtcgattg acgttacccg cagaagaagc accggctaac tccgtgccag cagccgcggt    480

aatacggagg gtgcaagcgt taatcggaat tactgggcgt aaagcgcacg caggcggtct    540

gtcaagtcgg atgtgaaatc cccgggctca acctgggaac tgcattcgaa actggcaggc    600

tagagtcttg taaggggggg gtagaattcc aggtgtagcg gtgaaatgcg tagagatctg    660

gaggaatacc ggnnncgaag gcggcccccct ggacaaagac tgacgctcag gtgcgaaagc    720

gtggggagca aacaggatta gataccctgg nagtccacgc cgtaaacgat gtcgacttgg    780

agttgtgccc ttgagcgtgn ntccggagct aacgcgttaa gtcgacgctg gggantacgg    840

cgcaggttaa actcaaatna attgacgggg gccngncnnn agcgggtngg ga            892
```

<210> SEQ ID NO 72
<211> LENGTH: 938
<212> TYPE: DNA
<213> ORGANISM: Artificial Sequence
<220> FEATURE:
<223> OTHER INFORMATION: Gam1-1-8-27F_C08.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (697)..(701)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (800)..(802)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (830)..(834)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (907)..(907)
<223> OTHER INFORMATION: n is a, c, g, or t
<220> FEATURE:
<221> NAME/KEY: misc_feature
<222> LOCATION: (919)..(921)
<223> OTHER INFORMATION: n is a, c, g, or t
<220> FEATURE:
<221> NAME/KEY: misc_feature
<222> LOCATION: (923)..(924)
<223> OTHER INFORMATION: n is a, c, g, or t
<220> FEATURE:
<221> NAME/KEY: misc_feature
<222> LOCATION: (929)..(929)
<223> OTHER INFORMATION: n is a, c, g, or t
<220> FEATURE:
<221> NAME/KEY: misc_feature
<222> LOCATION: (932)..(932)
<223> OTHER INFORMATION: n is a, c, g, or t
<220> FEATURE:
<221> NAME/KEY: misc_feature
<222> LOCATION: (934)..(935)
<223> OTHER INFORMATION: n is a, c, g, or t

<400> SEQUENCE: 72
gntancnntg caagtcgagc ggcagcggga aagtagcttg ctacttttgc cggcgagcgg 60
cggacgggtg agtaatgcct ggggatctgc ccagtcgagg gggataacta ctggaaacgg 120
tagctaatac cgcatacgcc ctacggggga aagcagggga ccttcgggcc ttgcgcgatt 180
ggatgaaccc aggtgggatt agctagttgg tgaggtaacg gctcaccaag gcgacgatcc 240
ctagctggtc tgagaggatg atcagccaca ctggaactga gacacggtcc agactcctac 300
gggaggcagc agtggggaat attgcacaat gggggaaacc ctgatgcagc catgccgcgt 360
gtgtgaagaa ggccttcggg ttgtaaagca ctttcagcga ggaggaaagg tcagtagcta 420
atatctgctg gctgtgacgt tactcgcaga agaagcaccg gctaactccg tgccagcagc 480

```
cgcggtaata cggagggtgc aagcgttaat cggaattact gggcgtaaag cgcacgcagg    540

cggttggata agttagatgt gaaagccccg ggctcaacct gggaattgca tttaaaactg    600

tccagctaga gttngntaga gggggggggta gaattccagg tgtagcggtg aaatgcgtag   660

agatctggag gaataccggt ggcgaaaggg cggcccnnnn nanaaaaant gagacgctca    720

ggtgcgaaag cgtgggggag caaacaggat ttagataccc tggtagtcca cgccgtaaac    780

gatgtcgatt tggaaggctn nngtccttga agacntngcc tcccggancn nnnngncgtt    840

aattcaatcg acctgnctgn gtgcagtacg gacngcnaag attaaaacct caaatgaaat    900

ttgaacnggg ggcccgccnn nanncgggng gnanncca                            938
```

```
<210> SEQ ID NO 73
<211> LENGTH: 894
<212> TYPE: DNA
<213> ORGANISM: Artificial Sequence
<220> FEATURE:
<223> OTHER INFORMATION: Gam1-1-9-27F_C09.ab1
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (624)..(628)
<223> OTHER INFORMATION: n is a, c, g, or t
<220> FEATURE:
<221> NAME/KEY: misc_feature
<222> LOCATION: (655)..(656)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t

<400> SEQUENCE: 73

gnnancnntg cnagtcgagc ggtagcacag gagagcttgc tctctgggtg acgagcggcg     60

gacgggtgag taatgtctgg gaaactgcct gatggagggg gataactact ggaaacggta    120

gctaataccg cataacgtcg caagaccaaa gagggggacc ttcgggcctc ttgccatcag    180

atgtgcccag atgggattag ctagtaggtg gggtaacggc tcacctaggc gacgatccct    240

agctggtctg agaggatgac cagccacact ggaactgaga cacggtccag actcctacgg    300
```

```
gaggcagcag tggggaatat tgcacaatgg gcgcaagcct gatgcagcca tgccgcgtgt    360

atgaagaagg ccttcgggtt gtaaagtact ttcagcgggg aggaaggtgt tgaggttaat    420

aacctcagca attgacgtta cccgcagaag aagcaccggc taactccgtg ccagcagccg    480

cggtaatacg gagggtgcaa gcgttaatcg gaattactgg gcgtaaagcg cacgcaggcg    540

gtctgtcaag tcggatgtga aatccccggg ctcaacctgg gaactgcatt cgaaactggc    600

aggctagagt cttgtagagg ggtnnnnnat ttcgggggtg aaggggtgaa atggnntana    660

agatcggggn agaaaatacc ggtggcgaag gcggccccct ggacaaagac tgacgctcng    720

tgcgaaagcg tggggagcaa acaggattag ataccctggt agtccacgcc gtaaacgatg    780

tcnacttgga ggttgtgccc ttgaggcgtg gcttccggag ctaacgcgtt agtcgaccgc    840

cngggggagt acggccgcaa ggttaaaact caaatggaat ttgacggggg cccg          894
```

```
<210> SEQ ID NO 74
<211> LENGTH: 813
<212> TYPE: DNA
<213> ORGANISM: Artificial Sequence
<220> FEATURE:
<223> OTHER INFORMATION: Gam1-1-41-27F_B10.ab1
<220> FEATURE:
<221> NAME/KEY: misc_feature
<222> LOCATION: (694)..(710)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (766)..(766)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:
<221> NAME/KEY: misc_feature
<222> LOCATION: (777)..(779)
<223> OTHER INFORMATION: n is a, c, g, or t
<220> FEATURE:
<221> NAME/KEY: misc_feature
<222> LOCATION: (783)..(785)
<223> OTHER INFORMATION: n is a, c, g, or t
<220> FEATURE:
<221> NAME/KEY: misc_feature
<222> LOCATION: (795)..(796)
<223> OTHER INFORMATION: n is a, c, g, or t
<220> FEATURE:
<221> NAME/KEY: misc_feature
<222> LOCATION: (798)..(799)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (804)..(804)
```

<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t

<400> SEQUENCE: 74

```
tgcaagtcga gcggcagcgg gaaagtagct tgctactttt gccggcgagc ggcggacggg     60

tgagtaatgc ctggggatct gcccagtcga gggggataac tactggaaac ggtagctaat    120

accgcatacg ccctacgggg gaaagcaggg gaccttcggg ccttgcgcga ttggatgaac    180

ccaggtggga ttagctagtt ggtgaggtaa cggctcacca aggcgacgat ccctagctgg    240

tctgagagga tgatcagcca cactggaact gagacacggt ccagactcct acgggaggca    300

gcagtgggga atattgcaca atgggcgcaa gcctgatgca gccatgctgc gtgtatgaag    360

aaggccttcg ggttgtaaag tactttcagc ggggaggaag gtgttgaggt taataacctc    420

agcaattgac gttacccgca gaagaagcac cggctaactc cgtgccagca gccgcggtaa    480

tacggagggt gcaagcgtta atcggaatta ctgggcgtaa agcgcacgca ggcggtctgt    540

caagtcggat gtgaaatccc cgggctcaac ctgggaactg cattcgaaac tggcaggcta    600

gagtcttgta gaggggggta gaattccagg tgtagcggtg aaatgcgtag agatctggag    660

gaataccggt ggcgaaggcg gccccctgga caannnnnnn nnnnnnnnnn gcgaaagcgt    720

ggggagcaaa cnggattaga taccctggta ntcnacgccn taaacnatgt cnacttnnng    780

gtnnngccct tgagnngnng nttncggan c taa                                813
```

<210> SEQ ID NO 75
<211> LENGTH: 803
<212> TYPE: DNA
<213> ORGANISM: Artificial Sequence
<220> FEATURE:
<223> OTHER INFORMATION: Gam1-1-42-27F_B11.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (702)..(704)
<223> OTHER INFORMATION: n is a, c, g, or t
<220> FEATURE:
<221> NAME/KEY: misc_feature
<222> LOCATION: (726)..(732)
<223> OTHER INFORMATION: n is a, c, g, or t
<220> FEATURE:
<221> NAME/KEY: misc_feature
<222> LOCATION: (734)..(735)
<223> OTHER INFORMATION: n is a, c, g, or t
<220> FEATURE:
<221> NAME/KEY: misc_feature
<222> LOCATION: (737)..(739)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (773)..(779)
<223> OTHER INFORMATION: n is a, c, g, or t
<220> FEATURE:
<221> NAME/KEY: misc_feature
<222> LOCATION: (782)..(782)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (795)..(798)
<223> OTHER INFORMATION: n is a, c, g, or t

<400> SEQUENCE: 75

```
tgcnagtcga gcggtaacac agggagcttg ctcctgggtg acgagcggcg gacgggtgag     60

taatgtctgg gaaactgcct gatggagggg gataactact ggaaacggta gctaataccg    120

cataacgtcg caagaccaaa gagggggacc ttcgggcctc ttgccatcag atgtgcccag    180

atgggattag ctagtaggtg gggtaatggc tcacctaggc gacgatccct agctggtctg    240

agaggatgac cagccacact ggaactgaga cacggtccag actcctacgg gaggcagcag    300

tggggaatat tgcacaatgg gcgcaagcct gatgcagcca tgccgcgtgt atgaagaagg    360

ccttcgggtt gtaaagtact ttcagcgggg aggaaggcga taaggttaat aaccttgtcg    420

attgacgtta cccgcagaag aagcaccggc taactccgtg ccagcagccg cggtaatacg    480

gagggtgcaa gcgttaatcg gaattactgg gcgtaaagcg cacgcaggcg gttggataag    540

ttagatgtga aagccccggg ctcaacctgg gaactgcatt cgaaactggc aggctagagt    600

cttgtagagg ggggtagaat tccaggtgta gcggtgaaat gcgtagagat ctggaggaat    660

accggtggcg aangcggccc cctggacaaa gactgacgct cnnntgcgaa agcgtgggga    720

gcaaannnnn nntnnannnc cntggtagtc cacgccgtaa acgatgtcna ctnnnnnnnt    780

gngcccttna gncgnnnntt ccg                                            803
```

<210> SEQ ID NO 76
<211> LENGTH: 777
<212> TYPE: DNA
<213> ORGANISM: Artificial Sequence
<220> FEATURE:
<223> OTHER INFORMATION: Gam1-1-43-27F_B12.ab1
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (709)..(711)
<223> OTHER INFORMATION: n is a, c, g, or t
<220> FEATURE:
<221> NAME/KEY: misc_feature
<222> LOCATION: (734)..(736)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (761)..(764)
<223> OTHER INFORMATION: n is a, c, g, or t
<220> FEATURE:

<221> NAME/KEY: misc_feature
<222> LOCATION: (773)..(774)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t

<400> SEQUENCE: 76

```
ctnnnntgca gtcgagcggt agcacaggag agcttgctct ctgggtgacg agcggcggac      60

gggtgagtaa tgtctgggaa actgcctgat ggagggggat aactactgga aacggtagct     120

aataccgcat aacgtcgcaa gaccaaagag ggggaccttc gggcctcttg ccatcagatg     180

tgcccagatg ggattagcta gtaggtgggg taacggctca cctaggcgac gatccctagc     240

tggtctgaga ggatgaccag ccacactgga actgagacac ggtccagact cctacgggag     300

gcagcagtgg ggaatattgc acaatgggcg caagcctgat gcagccatgc cgcgtgtatg     360

aagaaggcct tcgggttgta aagtactttc agcggggagg aaggtgttga ggttaataac     420

ctcagcaatt gacgttaccc gcagaagaag caccggctaa ctccgtgcca gcagccgcgg     480

taatacggag ggtgcaagcg ttaatcggaa ttactgggcg taaagcgcac gcaggcggtc     540

tgtcaagtcg gatgtgaaat ccccgggctc aacctgggaa ctgcattcga aactggcagg     600

ctagagtctt gtagaggggg gtagaattcc aggtgtagcg gtgaaatgcg tagagatctg     660

gaggaatacc ggtggcgaan gcggccccct ggacaaagac tgacgctcnn ntgcgaaagc     720

gtggggagca aacnnnatta gataccctgg tagtccacnc nnnnaacgat gtnnant        777
```

<210> SEQ ID NO 77
<211> LENGTH: 793
<212> TYPE: DNA
<213> ORGANISM: Artificial Sequence
<220> FEATURE:
<223> OTHER INFORMATION: GS1-1-1-27F_H01.ab1
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (679)..(680)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (687)..(689)
<223> OTHER INFORMATION: n is a, c, g, or t
<220> FEATURE:
<221> NAME/KEY: misc_feature
<222> LOCATION: (691)..(693)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (697)..(698)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (718)..(720)
<223> OTHER INFORMATION: n is a, c, g, or t
<220> FEATURE:
<221> NAME/KEY: misc_feature
<222> LOCATION: (722)..(726)
<223> OTHER INFORMATION: n is a, c, g, or t
<220> FEATURE:
<221> NAME/KEY: misc_feature
<222> LOCATION: (728)..(734)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t

<400> SEQUENCE: 77

```
cctacnntgc agtcgaacgg taacagaaag cagcttgctg ctttgctgac gagtggcgga     60

cgggtgagta atgtctggga aactgcctga tggaggggga taactactgg aaacggtagc    120

taataccgca taacgtcttc ggaccaaagt gggggacctt cgggcctcat gccatcagat    180

gtgcccagat gggattagct agtaggtggg gtaatggctc acctaggcga cgatccctag    240

ctggtctgag aggatgacca gccacactgg aactgagaca cggtccagac tcctacggga    300

ggcagcagtg gggaatattg cacaatgggc gcaagcctga tgcagccatg ccgcgtgtat    360

gaagaaggcc ttcgggttgt aaagtacttt cagcgaggag gaaggcgtta aggttaataa    420

ccttagtgat tgacgttact cgcagaagaa gcaccggcta actccgtgcc agcagccgcg    480

gtaatacgga gggtgcaagc gttaatcgga attactgggc gtaaagcgca cgcaggcggt    540

ctgtcaagtc ggatgtgaaa tccccgggct caacctggga actgcattcg aaactggcaa    600

gctagagtct tgtagagggg ggtagaattc caggtgtagc ggtgaaatgc gtagagatct    660

ggaggaatac cggtggcgnn gccncannng nnnangnngc ngacgctngg ngngagannn    720

cnnnnngnnn nnnncaggat tagataccct ggtagtccac gccgtaacga tgtcgacttg    780

gaggtnttcc ctt                                                       793
```

<210> SEQ ID NO 78
<211> LENGTH: 885
<212> TYPE: DNA
<213> ORGANISM: Artificial Sequence
<220> FEATURE:
<223> OTHER INFORMATION: GS1-1-2-27F_H02.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(703)
<223> OTHER INFORMATION: n is a, c, g, or t
<220> FEATURE:

<221> NAME/KEY: misc_feature
<222> LOCATION: (705)..(706)
<223> OTHER INFORMATION: n is a, c, g, or t
<220> FEATURE:
<221> NAME/KEY: misc_feature
<222> LOCATION: (708)..(711)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (733)..(735)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (750)..(751)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t
<220> FEATURE:
<221> NAME/KEY: misc_feature
<222> LOCATION: (808)..(809)
<223> OTHER INFORMATION: n is a, c, g, or t
<220> FEATURE:
<221> NAME/KEY: misc_feature
<222> LOCATION: (811)..(817)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (849)..(850)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (878)..(879)
<223> OTHER INFORMATION: n is a, c, g, or t

<400> SEQUENCE: 78
ctacnntgca agtcgagcgg tagcacaggg agcttgctcc tgggtgacga gcggcggacg 60
ggtgagtaat gtctgggaaa ctgcctgatg gagggggata actactggaa acggtagcta 120
ataccgcata acgtcttcgg accaaagtgg gggaccttcg ggcctcatgc catcagatgt 180

```
gcccagatgg gattagctag taggtggggt aatggctcac ctaggcgacg atccctagct    240

ggtctgagag gatgaccagc cacactggaa ctgagacacg gtccagactc ctacgggagg    300

cagcagtggg gagtattgca caatgggcgc aagcctgatg cagccatgcc gcgtgtatga    360

agaaggcctt cgggttgtaa agtactttca gcgaggagga aggcgttaag gttaataacc    420

ttagcgattg acgttactcg cagaagaagc accggctaac tccgtgccag cagccgcggt    480

aatacggagg gtgcaagcgt taatcggaat tactgggcgt aaagcgcacg caggcggttt    540

gtcaagtcgg atgtgaaatc cccgggctca acctgggaac tgcattcgaa actggcaagc    600

tagagtcttg tagagggggg tagaattcca ggtgtagcgg tgaaatgcgt agagatctgg    660

aggaataccg gtggcgaang cggccccctg gacaaagant gnngnngnnn nggggnaggg    720

ggaggggaga acnnnaggan taanataccn ngngtagtcc accnccgtaa acgatgtcga    780

cttggaaggt tgttcccttg aggantgnnt nnnnnnntaa cgccgttaan tccnccgcct    840

ggggantann gccgcaagnt aaacctcaaa atgaaatnna cgggg                   885
```

<210> SEQ ID NO 79
<211> LENGTH: 832
<212> TYPE: DNA
<213> ORGANISM: Artificial Sequence
<220> FEATURE:
<223> OTHER INFORMATION: GS1-1-3-27F_H03.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (706)..(712)
<223> OTHER INFORMATION: n is a, c, g, or t
<220> FEATURE:
<221> NAME/KEY: misc_feature
<222> LOCATION: (714)..(718)
<223> OTHER INFORMATION: n is a, c, g, or t
<220> FEATURE:
<221> NAME/KEY: misc_feature
<222> LOCATION: (722)..(723)
<223> OTHER INFORMATION: n is a, c, g, or t
<220> FEATURE:
<221> NAME/KEY: misc_feature
<222> LOCATION: (728)..(734)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (807)..(808)
<223> OTHER INFORMATION: n is a, c, g, or t
<220> FEATURE:
<221> NAME/KEY: misc_feature
<222> LOCATION: (821)..(821)

<223> OTHER INFORMATION: n is a, c, g, or t

<400> SEQUENCE: 79

```
ggctacnntg caagtcgaac ggtaacagaa agcagcttgc tgctttgctg acgagtggcg     60
gacgggtgag taatgtctgg gaaactgcct gatggagggg gataactact ggaaacggta    120
gctaataccg cataacgtct tcggaccaaa gtgggggacc ttcgggcctc atgccatcag    180
atgtgcccag atgggattag ctagtaggtg gggtaatggc tcacctaggc gacgatccct    240
agctggtctg agaggatgac cagccacact ggaactgaga cacggtccag actcctacgg    300
gaggcagcag tggggaatat tgcacaatgg gcgcaagcct gatgcagcca tgccgcgtgt    360
atgaagaagg ccttcgggtt gtaaagtact ttcagcgagg aggaaggcgt taaggttaat    420
aaccttagtg attgacgtta ctcgcagaag aagcaccggc taactccgtg ccagcagccg    480
cggtaatacg gagggtgcaa gcgttaatcg gaattactgg gcgtaaagcg cacgcaggcg    540
gtctgtcaag tcggatgtga aatccccggg ctcaacctgg gaactgcatt cgaaactgac    600
aggctagagt cttgtagagg ggggtagaat tccaggtgta gcggtgaaat gcgtagagat    660
ctggaggaat accggtggcg aaggcggccc cctggacaaa gactgnnnnn nnannnnnaa    720
gnnggggnnn nnnnacngga ttagatccnc tggtagtcca cgncngtaaa cgatgtcgac    780
ttggaaggtn gtgcccttga ggcgtgnntc cggagctacg ngttaagtcg ac            832
```

<210> SEQ ID NO 80
<211> LENGTH: 865
<212> TYPE: DNA
<213> ORGANISM: Artificial Sequence
<220> FEATURE:
<223> OTHER INFORMATION: GS1-1-4-27F_H04.ab1
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (647)..(652)
<223> OTHER INFORMATION: n is a, c, g, or t
<220> FEATURE:
<221> NAME/KEY: misc_feature
<222> LOCATION: (654)..(655)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (664)..(667)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (752)..(752)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (759)..(760)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (768)..(770)
<223> OTHER INFORMATION: n is a, c, g, or t
<220> FEATURE:
<221> NAME/KEY: misc_feature
<222> LOCATION: (772)..(777)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t
<220> FEATURE:
<221> NAME/KEY: misc_feature
<222> LOCATION: (810)..(812)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
<222> LOCATION: (818)..(822)
<223> OTHER INFORMATION: n is a, c, g, or t
<220> FEATURE:
<221> NAME/KEY: misc_feature
<222> LOCATION: (830)..(832)
<223> OTHER INFORMATION: n is a, c, g, or t
<220> FEATURE:
<221> NAME/KEY: misc_feature
<222> LOCATION: (837)..(839)
<223> OTHER INFORMATION: n is a, c, g, or t
<220> FEATURE:
<221> NAME/KEY: misc_feature
<222> LOCATION: (843)..(844)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (852)..(853)
<223> OTHER INFORMATION: n is a, c, g, or t
<220> FEATURE:
<221> NAME/KEY: misc_feature
<222> LOCATION: (857)..(859)

<223> OTHER INFORMATION: n is a, c, g, or t

<400> SEQUENCE: 80
ctacctgcaa gtcgaacggt aacaggaagc agcttgctgc ttcgccgacg agtggcggac 60
gggtgagtaa tgtctgggaa actgcctgat ggagggggat aactactgga aacggtagct 120
aataccgcat aacgtcttcg gaccaaagag ggggaccttc gggcctcttg ccatcagatg 180
tgcccagatg ggattagcta gtaggtgggg taatggctca cctaggcgac gatccctagc 240
tggtctgaga ggatgaccag ccacactgga actgagacac ggtccagact cctacgggag 300
gcagcagtgg ggaatattgc acaatgggcg caagcctgat gcagccatgc cgcgtgtatg 360
aagaaggcct tcgggttgta aagtactttc agcgaggagg aaggcgttaa ggttaataac 420
cttagcgatt gacgttactc gcagaagaag caccggctaa ctccgtgcca gcagccgcgg 480
taatacggag ggtgcaagcg ttaatcggaa ttactgggcg taaagcgcac gcaggcggtc 540
tgtcaagtcg gatgtgaaat ccccgggctc aacctgggaa ctgcattcga aactgacagg 600
ctagagtctt gtagaggggg gtagaattcc aggtgtagcg gtgangnnnn nncnncnggg 660
gggnnnngng cngccggggg cccccgcgaa aaancaaaga ctgacgctca ngtgcgaaag 720
cgtggggagc aaacaggatt agataccctg gnaatnccnn cncnaaannn annnnnnttt 780
ggnaggtngg nccctcttga ngggnggggn nntncggnnn nnaacgctan nnagtcnnna 840
ccnncnagcg gnngggnnnt acggc 865

<210> SEQ ID NO 81
<211> LENGTH: 868
<212> TYPE: DNA
<213> ORGANISM: Artificial Sequence
<220> FEATURE:
<223> OTHER INFORMATION: GS1-1-5-27F_H05.ab1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (762)..(763)
<223> OTHER INFORMATION: n is a, c, g, or t
<220> FEATURE:
<221> NAME/KEY: misc_feature
<222> LOCATION: (777)..(781)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t
<220> FEATURE:
<221> NAME/KEY: misc_feature

```
<222> LOCATION: (835)..(836)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (856)..(858)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t

<400> SEQUENCE: 81

ctaccntgca gtcgagcggt agcacaggga gcttgctcct gggtgacgag cggcggacgg     60

gtgagtaatg tctgggaaac tgcctgatgg agggggataa ctactggaaa cggtagctaa    120

taccgcataa cgtcttcgga ccaaagtggg ggaccttcgg gcctcatgcc atcagatgtg    180

cccagatggg attagctagt aggtgaggta atggctcacc taggcgacga tccctagctg    240

gtctgagagg atgaccagcc acactggaac tgagacacgg tccagactcc tacgggaggc    300

agcagtgggg aatattgcac aatgggcgca agcctgatgc agccatgccg cgtgtatgaa    360

gaaggccttc gggttgtaaa gtactttcag cgaggaggaa ggcgttaagg ttaataacct    420

tagcgattga cgttactcgc agaagaagca ccggctaact ccgtgccagc agccgcggta    480

atacggaggg tgcaagcgtt aatcggaatt actgggcgta aagcgcacgc aggcggtctg    540

tcaagtcgga tgtgaaatcc ccgggctcaa cctgggaact gcattcgaaa ctgacaggct    600

agagtcttgt agaggggggt agaattccag gtgtagcggt gaaatgcgta gagatctgga    660

ggaataccgg tggcgaaggc ggccccctgg acaaagactg acgctcaggt gcgaaagcgt    720

ggggagcaaa caggattaga taccctggna gtccacgccg tnncgatgtc gacttgnnnn    780

ngttcccttg agngtgnttc cggagctacg cgttagtcga cgcnggggan tangnncagt    840

aaactcaaat gnantnnncn gggggccc                                        868
```

COMPOSITION FOR CONTROLLING FISH

CROSS-REFERENCE TO RELATED APPLICATIONS

This application claims benefit of U.S. provisional application Ser. No. 61/158,121 filed Mar. 6, 2009.

FIELD OF THE INVENTION

The present invention is based on the development of a technology related to controlling the behavior of non-plant aquatic life. In particular, the technology may be used as an incitant to modify the feeding activities of fish. The present invention provides bacterial preparations that may be used to alter the feeding propensity of fish. The preparations may be useful for enhancing and or altering the diet preference of fish. The invention may include compositions that act as feeding incitants.

BACKGROUND OF THE INVENTION

Compositions for modifying fish behavior are well known in the art. Typically, such compositions include a liquid or particulate odor and/or taste or light attractant dispersed within a carrier material (see for example U.S. Pat. Nos. 5,097,616 and 5,393,537). Commonly used attractants include fish oils such as cod oil, herring oil, and salmon oil; extracts of various fishes and fish by-products including particulate fish parts; extracts and residues of earthworms; grubs and insects; anise oil; certain amino acids; fish egg extract; fish meal homogenate; morpholine; mineral oil; fragrances; fish scent; garlic oil; and extracts from shrimp, crabs, clams or artificial equivalents. Steroidal hormones have also been demonstrated to influence feeding behavior in fish (U.S. Pat. No. 7,335,349). Further, peptides, free amino acids, carbohydrates, organic nitrogen bases, nucleotides and nucleosides, and fatty acids may all be chemical cues/signals capable of eliciting and regulating behaviors of animals in aquatic environments (Zimmer 2008, Howe and Sheikh 1975; Pawlik 1992; Painter et al. 1998; Krug and Manzi 1999; Hardege et al. 2004; Cummins et al. 2005; Kicklighter et al. 2007).

Much research has been performed on coating compositions used as odor/taste attractants. For example, new forms of fish attracting compositions are disclosed in Meyers, U.S. Pat. No. 4,505,936, relating to an odor/taste attractant formed from shellfish waste and processed with certain additives, which prevent spoilage of the attractant; Valentincic, U.S. Pat. No. 5,185,164 relates to a catfish bait composition having at least one of a selected group of isolated amino acids; and Rittschof, U.S. Pat. No. 4,704,286 disclosing an attractant made of ground fish and certain other additives, which encourage a fish not to release bait once it has bitten it.

In addition, certain types of bacteria have been used with differing bait compositions. For instance, Ott, U.S. Pat. No. 4,369,176 relates to an insect bait composition that includes spore-producing bacteria of the genera *Bacillus*, selected because the bacterium secrets enzymes that ferment exogenous sugars yielding metabolic byproducts with insect-attractant values. Moreover, Asai, U.S. Pat. No. 4,202,905, attracts fish using luminous bait comprising a light producing bacteria.

Although many differing compositions have previously been used in attempts to attract fish, the specific use of bacteria related to or corresponding to a natural fish taste or smell has not previously been described or proposed. In addition, there is a growing need for a composition that controls specific species of fish with respect to specific dietary requirements (Naylor, Goldburg et al. 2000). Farming of carnivore/predator fishes places additional demands on the source of fish meal (e.g. marine feeder fish), and so a composition that could specifically incite feeding behavior in fishes, even in the absence of the preferred feeder fish, would be highly desirable. The present invention addresses this unmet need by providing compositions and methods to incite feeding behavior in fishes even when the preferred feeder fish is not present, either in whole or in part (i.e. fish homogenates, extracts, and the like).

Citation or identification of any document in this application is not admission that such document is available as prior art to the present invention.

SUMMARY OF THE INVENTION

The present invention relates to methods for obtaining bacteria from source aquatic animals and to methods of using said bacteria to elicit specific behaviors in target aquatic animals. Bacteria obtained according to said methods are specifically associated with, and released by, the source aquatic animals, and are responsible for the behaviors exhibited by the target aquatic animals in response to the presence of the source aquatic animals. The behavior-eliciting bacteria tend to be distinct from the bacteria commonly found in the surrounding water. The present invention further relates to behavior-eliciting compositions comprising said behavior-eliciting bacteria, which can be used to control aquatic non-plant life, including fish, crustaceans, larvae (hereinafter collectively referred to as fish), avians, and marine mammals. More particularly, the present invention provides compositions that can be incitants and/or attractants and/or repellents for fish, avians, and marine mammals depending upon the target species of fish, avian, and marine mammal and upon the composition used.

The present invention further relates to a method for preparing the behavior-eliciting compositions. The method may comprise extracting behavior-eliciting bacteria from a source fish, culturing the bacteria, then adding an effective amount of the bacteria to a substrate or carrier to produce the compositions. The compositions may comprise bacteria and may be used to modify the behavior of fish, avians, or marine mammals. Both live and inactivated bacteria may be used to produce the behavior-eliciting compositions. The bacteria may be prepared according to the methods disclosed herein, which includes the steps of extracting said bacteria from a source fish and culturing them in a suitable medium. The bacteria may be obtained from Fat Head Minnows (FHM) and be used to elicit feeding behavior in Largemouth Bass. The behavior-eliciting bacteria obtained from several common, commercially relevant source fish include those of the family Aeromonadaceae, Comamonadaceae, Enterobacteriaceae, and Moraxcellaceae, and of the genus *Acinetobacter, Aeromonas, Acidovorax*, and *Enterobacter*, though it will be obvious to those of ordinary skill in the art that the methods according to the present invention can be used to obtain and identify behavior-eliciting bacteria from any number of different source fish varieties. Any behavior-eliciting composition prepared according to the methods disclosed herein may be within the scope of the present invention.

The specific strain of the bacteria produced, such as the specific strain of *Acidovorax*, may be dependent on the type of fish from which the bacteria is extracted. Now that the methods and compositions of the present invention have been disclosed in great detail, an ordinarily skilled person or team will find it obvious to identify bacteria that may incite very specific feeding responses in specific target fish, avians, or marine mammals. For example, specific fish or feeder fish may be associated with specific strains of bacteria, and said strains may be responsible for the feeding behavior exhibited by a carnivore/predator fish, avian, or marine mammal. The extracted bacteria may be cultured in a dark environment in a minimal medium. The minimal medium may comprise organic compounds having carbon sources that may be simple and clearly defined.

Still another feature of the present invention may be that different bacterial strains may be selected based upon their ability to elicit different behavioral responses in fish, avians, or marine mammals. For example, the selected bacterial strain may either elicit feeding or avoidance behavior in a species of fish, avian, or marine mammal. Thus, the present invention provides for compositions that may be applied to artificial baits and/or incorporated into food to elicit feeding behavior in game fish, avians, or marine mammals. It will be immediately appreciated by a skilled person that with the appropriate selection of a source/feeder fish, the compositions according to the present invention may be used as a shark repellant. In addition, the compositions can be introduced into paint, and a composition-painted surface (for example, the hull of a boat or ship) may protect a boat, ship, or other vessel from, for example, barnacle attachment. Composition-painted surfaces could also cause marine mammals to avoid boats, ships or other vessels, thereby reducing injury to said mammals. In addition, the present compositions may be used to relocate spawning grounds or to alter migratory patterns.

To summarize, the present application fully discloses and describes an invention which addresses significant and long-felt needs, particularly in the field of aquaculture. Compositions according to the present application may be used to reduce or even eliminate the use of fish meal to feed fish, which addresses regulatory agency concerns of depleting wild small/feeder fish populations. The compositions may also reduce the cost of fish feed by encouraging fish to feed upon inexpensive, high quality protein sources which the fish would normally avoid due to lack of appropriate odor/taste signals. The compositions may reduce early stage mortality and optimize early stage growth, which would increase the profitability of aquaculture/farming. The compositions may also enable the farming of fish that normally would only eat "live" feed, thus producing new market opportunities. And finally, but not exhaustively, because the behavior-eliciting compositions comprise bacteria which are derived from fish already found in nature, environmental concerns are kept to a minimum, and organic labeling of fish fed the compositions should be fully supported.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other features and advantages of the present invention will be apparent to those skilled in the art from a careful reading of the Detailed Description of a Preferred Embodiment presented below.

BRIEF DESCRIPTION OF THE DRAWINGS

The following detailed description, given by way of examples, but not intended to limit the invention solely to the specific embodiments described, may best be understood in conjunction with the accompanying drawings, in which:

FIG. 9 is a listing of the SEQ ID NOs present in the sequence listing;

DETAILED DESCRIPTION OF THE INVENTION

Figure 1:
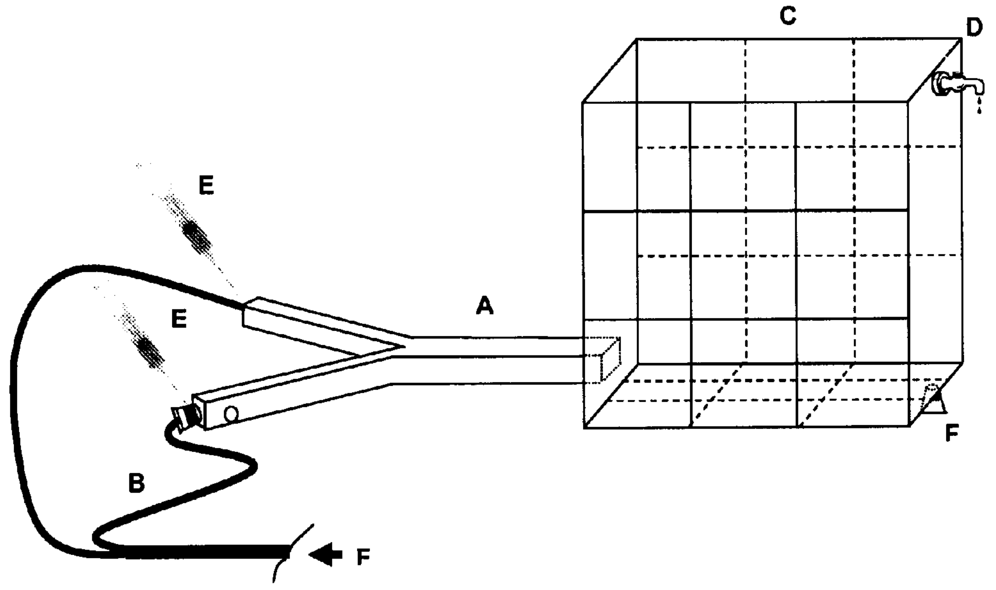
FIG. 1 is a diagram of the test chamber used to quantify fish response to introduced stimuli: A=Y-shaped inflow channel; B=plastic tubing leading from water source; C=chamber with grid lines; D=drain/overflow port; E=hypodermic syringe; F=drain plug.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicate otherwise.

Fish in general have sensitive chemoreceptors that contribute to their feeding and social behavior (Fisknes and Doving 1982; Hara 1992). In addition, different types of fish release distinct odor/taste to their surrounding waters. The distinctive odor/taste released by fish induce different responses in other nearby fish (Reutter, Boudriot et al. 2000). For example, the odor/taste of a minnow elicits a different response from surrounding fish than does that of a bass. Therefore, when a bass senses the stimulating odor/taste of a minnow, the bass will exhibit a predatory response, darting at the source of the odor/taste. In comparison, when a minnow senses the odor/taste released by a bass, the minnow responds with a fright response. The present invention is founded upon these responses to incitant stimuli i.e. odor/taste to control fish avians, or marine mammals.

In an embodiment of the present invention, certain bacteria determined to be associated with a given fish species are responsible for a distinctive odor/taste of that fish. Furthermore, such a distinctive odor/taste is normally released into the natural habitat of said fish. Upon isolation and presentation to fish, the olfactory and/or taste stimulating bacteria have been shown to affect the behavior of fish. These naturally occurring bacteria elicit responses depending on the bacterium used as the source odor/taste, and the species of the fish, avians, or marine mammal sensing the odor/taste. For example, introduction of certain bacterial strains into an environment causes a rapid, overt feeding reaction in one species of fish, while causing the opposite reaction (such as an escape reaction) in another species of fish. As expected, a fish exposed to an odor/taste of potential prey exhibit characteristic feeding behavior whereas a fish exposed to the odor/taste of a potential predator fish are repelled by the odor/taste.

As used herein, a "source fish" is hereby defined as a fish from which the bacteria are extracted. A source fish is customarily chosen because of the response it elicits from a second fish, avian, or marine mammal species. The "second species" hereby defined as the target (fish, avian, or marine mammal) is a species in which a desired response is elicited. For example, the target is the species of fish, avian, or marine mammal that is subject to incitant activity, i.e. the target is incited by the bacterial composition to exhibit either feeding or avoidance behavior. When water is used as a carrier, a mixture in the form of a suspension is formed with the bacteria. The concentration of the bacteria in the mixture is preferably at least approximately $1\times10^{12}$ bacteria per milliliter of water. This mixture can then be used, for example, to spray coat low-cost high quality protein sources to make said protein attractive to carnivore/predator fish.

It is believed that the bacteria responsible for the signal sent to carnivore/predator fish, whether it is smell, taste or both, may be largely of the genera *Acinetobacter, Aeromonas, Acidovorax*, and *Enterobacter*. The Fat Head Minnow (FHM) source fish were determined to largely harbor bacteria of the genus *Acidovorax*, though other behavior-eliciting bacteria may be associated with FHM. The data indicates that the carnivore/predator fish sense the odor/taste of these bacteria. The present invention suggests that different fish species harbor inherently different strains of *Acinetobacter, Aeromonas, Acidovorax*, and *Enterobacter* that emit different odors or tastes or signals from one another. Therefore, the specific bacteria used in the present invention are dependent on the fish species from which the bacteria are extracted. The specific bacteria are also dependent upon the desired behavior: if one wants to elicit feeding behavior, the bacteria will likely be isolated from source/feeder fish; if one wants to elicit avoidance behavior, the bacteria will likely be isolated from predator fish.

In some embodiments, the behavior-eliciting compositions may include a pharmaceutically or veterinarily acceptable carrier and/or diluent and/or excipient and bacteria. The bacteria used in the composition according to the present invention may be of the Aeromonadaceae, Comamonadaceae, Enterobacteriaceae, or Moraxcellaceae family, or of the *Acinetobacter, Aquamonas, Aeromonas, Citrobacter, Enterobacter, Erwina, Escherichia, Plesiomonas*, and *Salmonella* genus, or of the *Acidovorax* genus. The compositions may comprise bacteria which possess specific properties that stimulate a specific, desired response or behavior in fish, avians, or marine mammals.

In some embodiments, the compositions may include bacteria from TABLE 4 which lists the names and other characteristic information of bacteria which share significant sequence homology with bacteria isolated from Bluegills (BR), Golden Shiners (GS), Fathead Minnows (FHM), and Mosquitofish (Gam). Each of these fish species (supra) are appropriate feeder/source fish for the farming of economically useful predator fish.

In some embodiments, behavior-eliciting compositions made according to the instant application may comprise *Acinetobacter* sp. WH084, *Acinetobacter* sp. WH374, *Acinetobacter tjernbergiae, Aeromonas jandaei, Aeromonas jandaei* (T), *Aeromonas* sp. ', *Aeromonas* sp. DH14, *Aeromonas* sp. DH46, *Aeromonas* sp. DH57, *Aeromonas* sp. Lgg5.7, *Aeromonas* sp. MCCB 141, *Aeromonas* sp. RC278, *Aeromonas veronii*, bacterium SL2.12, or other "equivalent bacteria" which may be associated with and released by source fish, for example BR, GS, FHM, or Gam, to elicit behaviors in fish, avians, or marine mammals. As used herein "equivalent bacteria" means bacteria that possess an inherent odor/taste that allows them to elicit a reasonably equivalent response in a fish, avian, or marine mammals. The compositions may comprise bacteria having nucleotide sequences that have greater than 80% sequence homology with the nucleotide sequences as set forth in SEQ ID NOs:1-23.

In other embodiments, the behavior-eliciting compositions may comprise *Acidovorax facilis, Acidovorax* sp. ', *Acidovorax* sp. 12M7, *Acidovorax* sp. g32, *Acidovorax* sp. MG61, *Acidovorax* sp. R-24667, *Acidovorax* sp. Z022, *Aeromonas jandaei, Aeromonas jandaei* (T), *Aeromonas* sp., *Aeromonas* sp. ', *Aeromonas* sp. DH14, *Aeromonas* sp. DH54, *Aeromonas* sp. DH57, *Aeromonas* sp. DH58, *Aeromonas* sp. DH69, *Aeromonas* sp. Lgg5.7, *Aeromonas* sp. MBRG 4.2, *Aeromonas* sp. RC278, *Aeromonas veronii*, bacterium 2AT1, bacterium c07-4b, bacterium CYB24, bacterium E8, bacterium E8, bacterium G2, bacterium SL2.12, bacterium SNR2-1, *Buttiauxella agrestis, Buttiauxella* sp. 01WB03.2-68, *Citrobacter freundii, Citrobacter* sp. I101-10, *Citrobacter* sp. T40, endophytic bacterium HA04, endophytic bacterium HB02, *Enterobacter asburiae, Enterobacter cloacae* subsp. *cloacae, Enterobacter* sp. 196, *Enterobacter* sp. DH40-2, *Enterobacter* sp. DW56, *Enterobacter* sp. Mn2, *Enterobacter* sp. ZXM215, Enterobacteriaceae bacterium R-31537, filamentous bacterium J8, *Klebsiella pneumoniae, Microbacterium* sp. K10, *Pantoea agglomerans, Pantoea* sp. DW39, *Pseudomonas fluorescens, Salmonella enterica, Salmonella enterica* subsp. *enterica, Serratia* sp. R-17665, uncultured *Acidovorax* sp., uncultured beta proteobacterium, uncultured *Citrobacter* sp., uncultured Comamonadaceae bacterium, uncultured *Enterobacter* sp., uncultured Enterobacteriaceae bacterium, uncultured gamma proteobacterium, uncultured *Klebsiella* sp., uncultured proteobacterium, uncultured *Serratia* sp., or other "equivalent bacteria". The compositions may comprise bacteria having nucleotide sequences that have greater than 80% sequence homology with the nucleotide sequences as set forth in SEQ ID NOs:24-37.

In yet other embodiments, the behavior-eliciting compositions may comprise *Aeromonas jandaei, Aeromonas jandaei* (T), *Aeromonas* sp., *Aeromonas* sp. ', *Aeromonas* sp. DH14, *Aeromonas* sp. DH25, *Aeromonas* sp. DH46, *Aeromonas* sp. DH54, *Aeromonas* sp. DH57, *Aeromonas* sp. DH58, *Aeromonas* sp. DH69, *Aeromonas* sp. Lgg5.7, *Aeromonas* sp. MBRG 4.2, *Aeromonas* sp. RC278, *Aeromonas veronii*, bacterium 2AT1, bacterium c07-4-b, bacterium G2, bacterium SL2.12, bacterium SNR2-1, *Citrobacter freundii, Citrobacter* sp. I101-10, *Citrobacter* sp. T40, endophytic bacterium HA04, endophytic bacterium HB02, *Enterobacter*

*asburiae, Enterobacter cloacae* subsp. *cloacae, Enterobacter* sp. 196, *Enterobacter* sp. DH40-2, *Enterobacter* sp. DW56, *Enterobacter* sp. Mn2, *Enterobacter* sp. ZXM215, Enterobacteriaceae bacterium R-31537, *Klebsiella pneumoniae, Microbacterium* sp. K10, *Pantoea agglomerans, Pantoea* sp. DW39, *Pseudomonas fluorescens, Salmonella enterica, Salmonella enterica* subsp. *enterica, Salmonella enterica* subsp. *enterica* serovar *Dublin, Salmonella enterica* subsp. *enterica* serovar *Enteritidis, Salmonella enterica* subsp. *enterica* serovar *Typhi, Salmonella enterica* subsp. *enterica* serovar *Typhimurium, Serratia* sp. R-17665, uncultured *Citrobacter* sp., uncultured *Enterobacter* sp., uncultured Enterobacteriaceae bacterium, uncultured gamma proteobacterium, uncultured *Klebsiella* sp., uncultured proteobacterium, uncultured *Serratia* sp., or other equivalent bacteria. The compositions may comprise bacteria having nucleotide sequences that have greater than 80% sequence homology with the nucleotide sequences as set forth in SEQ ID NOs:38-76.

In other embodiments, the compositions may comprise bacterium E8, *Buttiauxella agrestis, Buttiauxella* sp. 01WB03.2-68, Enterobacteriaceae bacterium R-31537, *Serratia* sp. R-17665, uncultured *Citrobacter* sp., uncultured *Enterobacter* sp., uncultured proteobacterium, uncultured *Serratia* sp., or other equivalent bacteria. The compositions may comprise bacteria having nucleotide sequences that have greater than 80% sequence homology with the nucleotide sequences as set forth in SEQ ID NOs:77-81.

As used herein, the terms "pharmaceutically or veterinarily acceptable carrier" and "pharmaceutically or veterinarily acceptable vehicle" and "pharmaceutically or veterinarily acceptable excipient" are interchangeable and refer to a substrate that can be consumed by a target species without significant adverse effects. Suitable pharmaceutically acceptable carriers known in the art include, but are not limited to, sterile water, saline, glucose, or buffered solutions. Carriers may include auxiliary agents including, but not limited to feed, diluents, stabilizers (i.e., sugars and amino acids), preservatives, wetting agents, emulsifying agents, pH buffering agents, viscosity enhancing additives, colors and the like. The pharmaceutically or veterinarily acceptable carriers or vehicles or excipients are well known to the one skilled in the art. For example, a pharmaceutically or veterinarily acceptable carrier or vehicle or excipient can be a NaCl (e.g., saline) solution or a phosphate buffer. In another example, the excipient, carrier or vehicle may be fish, avian or marine mammal food such as, but not limited to, meal, pellets, or slurries. Amounts and volumes are herein discussed in the general description and can also be determined by the skilled artisan from this disclosure read in conjunction with the knowledge in the art, without any undue experimentation.

In one embodiment, the bacteria of the behavior-eliciting compositions may be prepared by isolating bacteria from a species of fish (source fish) by removing an aliquot of conditioned water (water from the aquaria that the source fish have inhabited, for example, for >30 minutes), inoculating growth media with a portion of said aliquot, propagating said bacteria in growth media, streaking said bacteria to form single colony isolates on nutrient agar plates/slants, and subsequently subculturing such isolates in growth media.

To obtain a composition having a certain odor/taste, a specific species of source/feeder fish, such as fathead minnows, are placed in a container of water and allowed to swim for a sufficient amount of time, reasonably at least ten minutes. To prevent any undesirable contaminants, i.e. algae, bacteria, parasites, etc. in the final composition, the aquaria water used is initially chlorinated and is subsequently dechlorinated and passed through a 0.45 μm filter prior to the addition of subject fish. The fish will release bacteria into the dechlorinated water immediately, however, the longer the fish is exposed to the water the greater the amount of bacteria that will be released ultimately yielding the conditioned water. After a sufficient amount of time (10 minutes to 1.0 hour), a culturing medium is inoculated with an aliquot of the conditioned water.

Any suitable growth medium capable of culturing the bacteria released by the fish may be used; however a minimal medium is may be more effective. Minimal media contains the minimum nutrients possible for colony growth, generally without the presence of amino acids, and typically contains: 1) a carbon source for bacterial growth, which may be a sugar such as glucose, or a less energy-rich source like citrate; 2) various salts, which may vary amongst the specific bacterium of the composition and growing conditions; these salts generally provide essential elements such as magnesium, nitrogen, phosphorus, and sulfur to allow the bacteria to synthesize protein and nucleic acid; 3) water (Davis, Dulbecco et al. 1990). For the present invention, a suitable minimal medium may comprise: potassium phosphate-dibasic, potassium phosphate-monobasic, ammonium sulfate, sodium citrate, magnesium sulfate and deionized water. The entire volume of prepared minimal medium is then sterilized by passage through a 0.45 μm filter. The citrate of the sodium citrate is the carbon source in that particular minimal medium. In another embodiment, sterile glucose (autoclaved or sterile-filtered) is added to the above mentioned minimal medium as a carbon source.

In another embodiment of the present invention the minimal medium may comprise: potassium phosphate-dibasic, present in an amount of approximately 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0%, frequently 0.7% by weight; potassium phosphate-monobasic, present in an amount of approximately 0.1%, 0.2%, 0.3%, 0.4%, 0.5%, 0.6%, 0.7%, 0.8%, 0.9%, or 1.0%, frequently 0.3% by weight; ammonium sulfate, present in an amount of approximately 0.01%, 0.02%, 0.03%, 0.04%, 0.05%, 0.06%, 0.07%, 0.08%, 0.09%, 0.10%, 0.20%, 0.3%, 0.4%, 0.5%, 0.6%, 0.7%, or 0.8%, frequently 0.1% by weight; sodium sulfatecitrate, present in an amount of approximately 0.005%, 0.15%, 0.20%, 0.25%, 0.30%, 0.35%, 0.40%, 0.45%, 0.50%, or 0.55%, frequently 0.051% by weight; magnesium sulfate, present in an amount between approximately 0.001%, 0.002%, 0.003%, 0.004%, 0.005%, 0.006%, 0.007%, 0.008%, 0.009%, 0.010%, 0.020%, or 0.03%, frequently 0.01% by weight; distilled water, present in an amount of approximately 70%, 71%, 72%, 73%, 74%, 75%, 76% 78%, 79%, 80%, 81%, 82%, 83%, 84%, 85%, 86% 88%, 89%, 90%, 91%, 92%, 93%, 94%, 95%, 96% 97%, 98%, or 99%, most frequently 94% by weight; and a concentrated solution of sterile glucose (about 10 to 70% w/v) diluted in the final medium to a weight volume concentration of approximately 1.0%, 2.0%, 3.0%, 4.0%, 5.0%, 6.0%, 7.0%, 8.0%, 9.0% or 10.0%, frequently 5.0%.

The bacteria (isolated as described above) were cultured in a dark environment to reduce the growth of algae that may be present in the initial sample. Bacterial growth began immediately upon inoculation of the culture medium and continued through logarithmic phase until stationary phase was reached, at approximately 48 hours post inoculation (Davis, Dulbecco et al. 1990). No adverse effects were experienced from culturing for times periods greater or less than 48 hours. Culturing for fewer than 48 hours decreased the quantity of the composition produced and culturing for more than 48 hours had little or no effect on the concentration of the final composition.

Bacteria were grown in minimal culture media for approximately 48 hours to achieve stationary phase (Davis, Dulbecco et al. 1990). Subsequently, the bacteria were killed by adding 37% formaldehyde to the culture to a final concentration of 1.0% (v/v). The bacteria were separated (pelleted) from the medium by centrifugation at 7,000×G for 10 minutes at 20° C. To ensure adequate removal of formaldehyde, the supernatant is separated from the bacterial cell pellet by filtering, decanting, or aspiration, and the pelleted bacteria were resuspended in a volume of distilled water equivalent to the volume of the initial culture. The resuspended bacteria were pelleted again using the same centrifugation parameters. The bacterial cell pellet was resuspended in distilled water. This process was repeated two (2) more times, discarding the supernatant obtained from the centrifugation step. The final cell pellet was then mixed with an appropriate volume of desired solution or excipient to form a bacterial suspension (i.e. a behavior-eliciting composition).

In another embodiment, the bacteria are resuspended with an appropriate volume of distilled water to form a composition with a bacterial concentration of approximately $1.0\times10^{7}$, $1.5\times10^{7}$, $1.0\times10^{8}$, $1.5\times10^{8}$, $1.0\times10^{9}$, $1.5\times10^{9}$, $1.0\times10^{19}$, $1.5\times10^{19}$, or $1.0\times10^{11}$ bacteria per milliliter. In one embodiment, the water/composition mixture is applied to an object of interest, such as fish food. Application of the mixture may be accomplished by any means known in the art, such as spraying, soaking, mixing etc. When used to enhance the attractiveness of fish food, the amount of the composition applied on, mixed with, or associated with one pound of fish food is approximately $1.0\times10^{9}$, $1.5\times10^{9}$, $1.0\times10^{10}$, $1.5\times10^{10}$, or $1.0\times10^{11}$, $1.0\times10^{10}$, $1.5\times10^{10}$, $1.0\times10^{11}$, $1.5\times10^{11}$, $1.0\times10^{12}$, $1.5\times10^{12}$, $1.0\times10^{13}$, or $1.5\times10^{13}$ bacteria. Alternative substrates can be used depending on the purpose of the composition. For example, the composition can be mixed with food at the time of formulation, and solutions/substrates compatible with the formulation process as necessary.

Feed is the largest production cost for commercial aquaculture (for example, most farming of salmon, other marine finfish and shrimp), and thus improving feed efficiency in industrial systems is a priority (Naylor, Goldberg et al. 2000). A primary advantage of the present invention is that the behavior-eliciting compositions can be incorporated into low cost, high protein food for fish, avians, or marine mammals. There are a number of commercial food suppliers (Purinamills, AquaMax, Gray Summit Mo.; Cargill, Aquaxcel, Franklinton La.; Zeigler Bros., Gardners Pa.) that offer low cost fish foods. Typically, such low cost high protein foods are efficient, and economically viable, (Lim and Webster 2001) but unfortunately they are usually unpalatable (Subcommittee-Fish-Nutrition 1993). For example, many types of fish refuse to eat inexpensive high protein food sources containing casein. In fact, certain bass fish will starve rather than eat casein. However, when a composition comprising cultured bacteria extracted from a normal bass prey fish, such as minnow source fishes, is applied to casein-based food, the bass will eat and sustain a reasonable amount of growth on the casein diet. Therefore, behavior-eliciting compositions according to the present invention inexpensively transform otherwise unpalatable high protein food sources into efficient palatable food sources. A further aspect of the present invention is that the bacterial compositions additionally possess inherent nutritional value.

Another feature of the present invention is the combination of the cultured bacteria and particular carriers. By combining the bacteria with low-cost protein sources, for example, fish will consume the protein whereas without the bacteria, said fish would find it unpalatable, and in some cases, they would starve. This aspect is particularly important during the process of weaning fish to commercially available fish food, where mortality can exceed 60%. Behavior-eliciting compositions according to the present invention may dramatically reduce fish mortality, thus significantly reducing aquaculture costs.

All documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Example 1

Test Chamber

In the present invention, a test chamber was designed and used for quantitative analysis of feeding, predator avoidance, and other behaviors of test subjects. The test chamber shown in FIG. 1 was constructed of clear poly(methyl 2-methylpropenoate) (PLEXIGLAS) and consists of a main chamber with a "Y-shaped" inflow channel. The chamber volume is 28 cm×29 cm×27 cm and has a capacity of ~22.0 Liters. The inflow channel allows introduction of substrates and compositions of interest. Each section of the inflow channel is square in cross-section (13.69 $cm^2$) and 30.0 cm in length.

During operation, dechlorinated tap water (prepared as described below) was continuously fed through both arms of the inflow channels. The two water streams from each inflow channel converge and enter the main chamber at the bottom/center of the main chamber. The water in the main chamber overflowed through an opening near the top of the main chamber on the side opposite the inflow channels. Lines marked on the two sides and bottom of the main chamber formed nine squares on each face of the apparatus. The lines delineate 27 virtual cubic "compartments" in the main chamber.

Fish were introduced to the main chamber through the open top of the apparatus. Each time a fish moved from one of the 27 virtual cubic compartments (see above) to another, the move was recorded as an event by the observer. Substances in solution were added to the incoming water stream by penetrating a rubber septum at the entry port of either inflow arm with a hypodermic needle. Solutions and compositions of interest were added as single injections via a syringe attached to the injection needle or continuously pumped into the water stream.

Dechlorination.

A 20 Liter plastic carboy, with a bottom spigot, served as a dechlorinating vessel. Tap water flowed in to the top of the carboy through plastic tubing at a rate of 3.0 Liters per minute. A peristaltic pump was used to add 0.2 M sodium thiosulfate to the carboy at a rate of 2.5 milliliters per minute to remove the chlorine. Chlorine removal (Eaton, Clesceri et al. 1992) was monitored with a Hach Chlorine Test Kit (Hach Co., Loveland Colo., Model CN-66F).

Flow dynamics for the apparatus were tested by injecting 1.0% methylene blue into one of the inflow arms through the designated port followed by visual observation of the distribution of blue color. The degree of dilution of test substances in each cubic grid compartment of the main chamber was assessed using pH measurements. Briefly, with water flowing through the chamber, 10.0 ml volumes of 1.0 N HCl were injected through one of the inflow arms of the apparatus. At intervals, 10.0 ml samples of water were removed from the center of each cubic grid compartment with a pipette. Measurement of pH in the samples allowed calculation of dilution factors in the various grid compartments.

Water temperatures in the test chamber were adjusted to be within 1° C. of the source aquaria.

Example 2

Use of the Test Chamber

The test chamber described above (FIG. 1) was designed to allow monitoring of the swimming movements of fish in response to components in flowing water. Similar chambers have been used by others for quantitative and semi-quantitative evaluations of various kinds of fish behaviors evoked by components in solution. (Kleerekoper 1969; Bardach and Villars 1974; Pfeiffer 1982). In essence, hungry fish exhibit increased swimming movements in response to positive stimuli, i.e. natural and synthetic amino acids (Carr 1988) and extracts of prey fish specific to the fish species being observed.

In all tests, individual fish were observed during three sequential 10 minute periods. The first 10 minutes in the test chamber served as an acclimation period. The second 10 minute interval served as a control period during which only dechlorinated tap water was injected and fish movements were recorded. At the beginning of the last period, the experimental period, the composition of interest was injected and fish movements were recorded.

Results from the test chamber consist of recordings of movements for each fish through the grids within the test chamber during the control period and the experimental period. Mean movements during control and experimental periods were accompanied by standard errors. Differences between means were tested using the t-test for paired comparisons (Sokal and Rohlf 1969). This test evaluates the significance of the difference between the two means obtained in experimental condition where a significance requires a p value $\leq 0.05$.

Example 3

Determining the Response of Fish to Another Fish Species "Odor/Taste"

Figure 2:
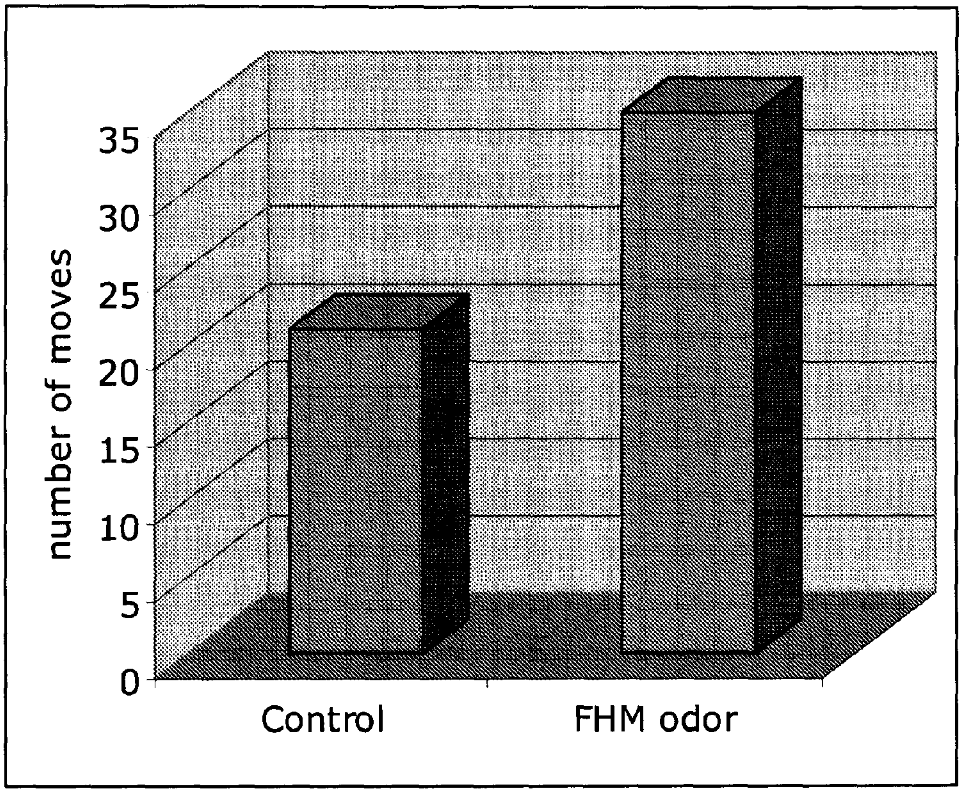
FIG. 2 is a graph depicting the movements of hungry largemouth bass in response to fathead minnow odor/taste.
Figure 3:
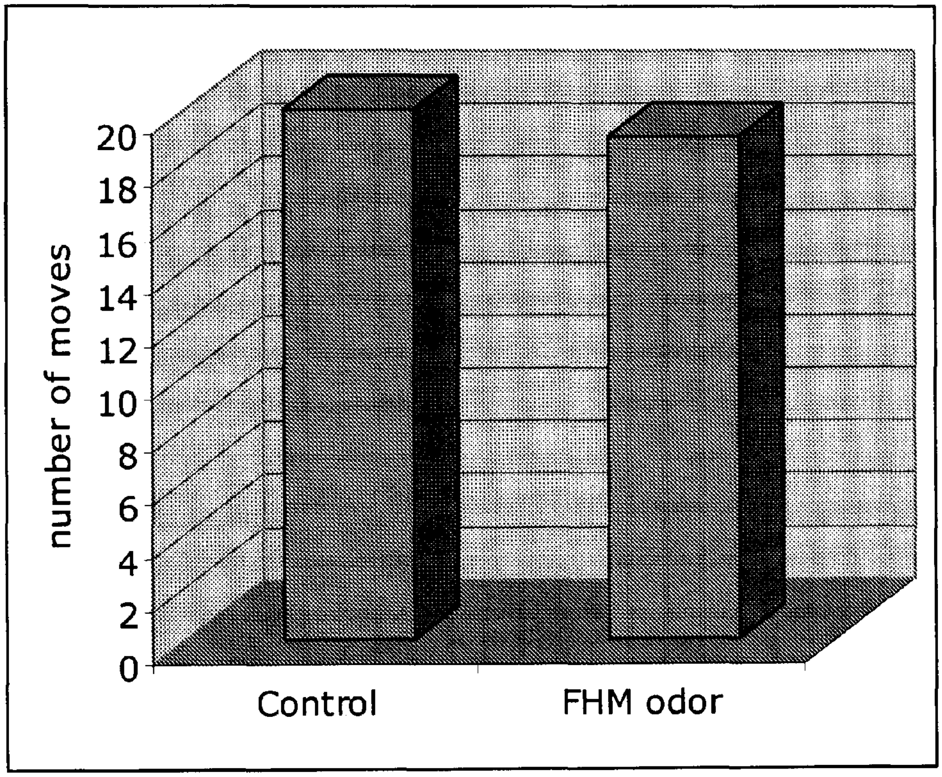
FIG. 3 is a graph illustrating the movements of recently fed largemouth bass in response to fathead minnow odor/taste.

The olfactometric/taste test chamber (FIG. 1) was used to determine how largemouth bass and several species of small fish react to each other's odor/taste (measurements as per Example 2, above). It was observed that small fish (yellow fin shiner, fathead minnow) often react to bass odor/taste by becoming motionless (fright response), whereas hungry bass responded to the odor/taste of the small fish with searching movements, also referred to as exploratory feeding behavior (FIG. 2). Bass that had just been fed ignored the odor/taste of the small fish (see FIG. 3).

Characterization of the Avoidance Odor/Taste Response.

Water was taken from an aquarium which housed a largemouth bass for tests of avoidance by small fish (said water will be hereinafter referred to as "bass water" or "conditioned bass water"). The bass water was tested immediately after removal from the tank. In this embodiment, FHM and YFS were tested as described below.

Conditioned bass water was obtained from aquaria in which bass had been 1) swimming, 2) housed, or from a 3) new tank that had housed bass fish for 30 minutes. The bass were removed by netting them, and the resulting 3 types of conditioned bass water were used as described below to determine the nature of the response said water would elicit in FHM.

Behavior.

The response of each species to bass water appeared to depend on whether or not the test fish were hungry. Hungry FHM stopped swimming for between one (1) and two (2) minutes when exposed to bass water. The FHM slowly resumed swimming as the bass water was diluted. Satiated FHM exhibited a slight reduction in their swimming activity when exposed to bass water (P=0.11). Hungry YFS responded to bass water with rapid darting, followed by entry into the inflow channel in 60% of the trials. This entry was delayed until the inflow channel had been flushed of the bass water (average 7.6 min). Satiated YFS did respond to bass water with moderate swimming activity, but did not enter the inflow channel.

Filtration Removes the Bass Odor/Taste.

Conditioned bass water was sterile-filtered through a 0.45 μm filter (e.g., Millipore Corp., Billerica Mass., # SJHVM4710, 0.45 μm), and was then tested in the chamber as described above. After filtration, the FHM responses elicited by bass water were similar to those elicited by the dechlorinated control water, indicating that no avoidance. In this experiment, the FHM fish increased their movement similar to the dechlorinated tap water control. These results show that the odor/taste responsible for the avoidance behavior of FHM is particulate and can be removed by filtration.

Centrifugation.

Thirty (30.0) ml of conditioned bass water was transferred to sterile conical centrifuge tubes. The tubes were centrifuged at room temperature for 10 minutes at 7,000×G. An aliquot of the supernatant was removed from the centrifuge tube, and was used in a 'finger' bowl experiment in which one FHM fish was added to a small 'finger' bowl containing 230 ml of dechlorinated tap water. The fish was allowed to acclimate for 15 minutes and then 1.0 ml of conditioned bass water was added to the bowl and the fish motion was monitored. In the finger bowl experiments, the FHM fish increased their movement, similar to the response observed with the dechlorinated tap water controls and the 0.45 μm filtered water. Consequently, this result shows that the odor/taste responsible for the avoidance behavior in FHM can be removed from aqueous solution at low centrifugal forces that are typically used to pellet bacteria.

The Odor/Taste is Bacteria.

The experiments described above strongly suggested that bacteria were the odor/taste to which the FHM were responding. To explore this possibility, 1.0 ml of conditioned bass water was plated on sterile nutrient agar plates (agar solidified in 15 cm covered Petri dishes). Petri dishes were incubated at 25° C. for 24 hours. Plating on nutrient agar generated ~4,000 bacterial colonies per ml of conditioned bass water. Control dechlorinated tap water yielded <100 colonies per ml. Using a sterile loop, bacteria from isolated colonies on nutrient agar plates were used to inoculate: agar slants (storage copies), nutrient broth medium, and minimal medium as described above. Growth in both nutrient medium (4 days at 25° C.) and minimal medium (6 days at 25° C.) yielded bacterial growth to levels of ~$1.0\times10^9$ bacterial per ml. Bacterial from nutrient broth and minimal medium were diluted to $1.0\times10^6$ per ml. These bacteria were used in the finger bowl assay (described above) to determine the effect on FHM fish. Results showed that bacteria grown on nutrient broth had no effect on FHM response, similar to controls. More importantly, however, it was observed that in the presence of bacteria grown on minimal medium, the FHM fish froze in a typical avoidance behavior. The response was identical to that observed conditioned bass medium (described above). This finding showed that bacteria inherently associated with bass fish were sufficient to elicit the odor/taste response in FHM fish (i.e. the avoidance behavior).

Typing of the Bacterial (Composition) as *Citrobacter*.

Individual colonies that formed from streaking the minimal media agar plates were used to inoculate minimal growth medium, minimal medium agar slants, and minimal medium agar Petri dishes. The resultant bacterial cultures were used as a source for subsequent analyses. Gram staining of selected individual cultures as well as the starting culture exhibited gram-negative characteristics (Bergey 1994). Aliquots of liquid cultured material were microscopically observed using oil-immersion at 1000× magnification. The bacteria were found to be rod-shaped and typically as attached duplets. Since the bacteria were Gram negative and rod shaped (bacillus), the diagnostic test employed for typing was the API 20E test strip (BioMerieux, Inc., #20100 api 20E). The API 20E system consists of a plastic strip of 20 individual, miniaturized tests tubes (cupules) each containing a different reagent used to determine the metabolic capabilities, and, ultimately, the genus and species of enteric bacteria in the family Enterobacteraceae. Single colonies from six different cultures were used to inoculate a 0.85% saline solution, and after mixing, the inoculated saline solution was applied to API 20E strips rehydrating the dried reagent in each tube on the strip. Some of the tubes are completely filled (tests CIT, VP and GEL), whereas others were topped off with mineral oil so that the anaerobic reactions (reactions that occur in the absence of oxygen) could be carried out (tests ADH, LDC, ODC, H2S, URE). The strips were then incubated in a small, plastic humidity chamber for 18-24 hours at 37° C. Living bacteria produce metabolites and wastes as part of the business of being a functioning cell. The reagents in the cupules are specifically designed to test for the presence of products of bacterial metabolism specific to certain kinds of bacteria. After incubation, each tube (an individual test) was assessed for a specific color change indicating the presence of a metabolic reaction that sheds light on the microbe's identity. Some of the cupule contents changed color due to pH differences, others contained end products that must be identified using additional reagents. Interpretation of the 20 reactions, in addition to the oxidase reaction (which was done separately), was converted to a seven-digit code. Results of the analysis yielded an API code of 0604532 that corresponded to the bacterial identifier *Citrobacter freundii*.

Odor/Taste is Ubiquitous in Fish Species Tested.

In a manner similar to that described above, bacteria specific to a given fish species can be shown to be the causative agent for avoidance or attraction to a second fish, avian, or marine mammal. For example, FHM fish (prey fish) were found to harbor bacteria that elicit feeding behavior in bass fish (predator fish). As illustrated by FIG. 2, hungry largemouth bass moved significantly more in response to the fathead minnow (FHM) odor/taste, as compared to control water. In contrast, recently fed largemouth bass do not respond significantly differently to fathead minnow odor/taste, as compared to control water (FIG. 2). In sum, these results indicated that bass preferentially responded to FHM odor/taste only when they were hungry. Bass also responded equally well to formaldehyde-inactivated bacteria.

FHM responses were then tested using samples of the minimal medium containing bass bacteria (with appropriate controls) as well as formaldehyde-fixed, washed bacteria. Both kinds of samples caused fright responses in the minnows, just as fresh bass water had. These results showed that the bacteria did not have to be live to elicit behavioral responses from the minnows. Therefore, the present application is intended to encompass compositions which comprise bacteria that have been inactivated by any well-known method that still preserve the ability of the bacteria to elicit a desired behavior in a target fish, avian or marine mammal. The ability to use either live or inactivated bacteria offers a clear advantage to customers that may exhibit a preference for one over the other.

Example 4

Preparation of the Bacteria (Composition)

The Seed Culture.

The behavior-eliciting composition was obtained by allowing fathead minnows (FHM) to swim in a container of sterile dechlorinated tap water for between 15 minutes to one (1) hour. After this time period, a 1.0 ml aliquot of this water was removed using a sterile pipette and is subsequently transferred to 1.0 L of minimal medium (prepared according to the ingredients listed in TABLE 1) in a 3.0 L Erlenmeyer flask.

TABLE 1 components of the minimal medium.

| Component | Amount |
|---|---|
| Potassium Phosphate - Dibasic | 7.0 gm |
| Potassium Phosphate - Monobasic | 3.0 gm |
| Ammonium Sulfate | 1.0 gm |
| Sodium Citrate | 0.5 gm |
| Magnesium sulfate | 0.1 gm |
| Distilled Water | 950.0 ml |

The prepared medium was stored in covered 3.0 L Erlenmeyer flasks and was sterilized in a suitable apparatus, preferably an autoclave. After sterilization, 50.0 milliliters of a sterilized 4% glucose solution was aseptically added to the sterilized culture medium to form the preferred minimal medium.

Growth of the Composition.

A 1.0 ml aliquot of the seed bacteria (see above) was subsequently added to 1.0 L of the preferred minimal medium in a 3.0 L flask. The flask was placed in a dark environment at 20° C. for 48 hours, to avoid or minimize any possible algal growth. After 48 hours of growth, the bacteria (composition) were fixed, centrifuged, and washed at least 2 times with an appropriate volume of distilled water. Bacteria were centrifuged a final time, the supernatant discarded, and the packed cells resuspended with water to form a behavior-eliciting composition having a bacterial concentration of $1.0\times10^{12}$ bacteria per milliliter.

Example 5

In view of the response elicited by the fathead minnow, Example 5 demonstrates how bacteria extracted from prey fish might be useful in enhancing the acceptability of fish chows, potentially allowing a reduction in the cost of the chow without affecting the growth of the fish. Feeding experiments using hybrid striped bass fingerlings and fry were conducted using various mixtures of Trout Chow and casein.

Figure 10:
FIG. 10 is an EM photomicrograph of fish food coated with compositions according to the present invention.

For all the feeding experiments, approximately 24 pounds of feed was coated in two 12 pound lots—one was to receive the high level of behavior-eliciting composition/coating, and the other would receive the low level of composition/coating. For the coating, 22 liters of FHM-derived bacterial culture was grown and then concentrated and washed to a final packed volume of 900 ml. The 900 ml was divided into 600 ml for the high coating and 300 ml for the low coating. Each aliquot was resuspended in about 1 liter and hand sprayed onto the pellets of feed using a standard garden-type sprayer. The pellets were carefully mixed and spread on aluminum foil to dry overnight. A representative micro-photograph of coated feed is presented in FIG. 10.

Four (4) different diets were tested. Three tanks of ten fish were fed Trout Chow (TC). Other groups of three tanks were fed the 60% casein/40% Trout Chow mixture without any top-coating (C) (see TABLE 2 for the contents of the casein formula), the 60% casein/40% Trout Chow mixture coated with a low level of the present composition (chosen arbitrarily and designated K1); and the 60% casein/40% Trout Chow mixture coated with a high level of the present composition, which was twice the level of the low level (K2). It had already been determined that the hybrid striped bass did not gain much weight on the Trout Chow/Casein diet alone. The behavior-eliciting composition was prepared as described and comprised inactivated bacteria that had been extracted from fathead minnows (FHM).

Figure 4:
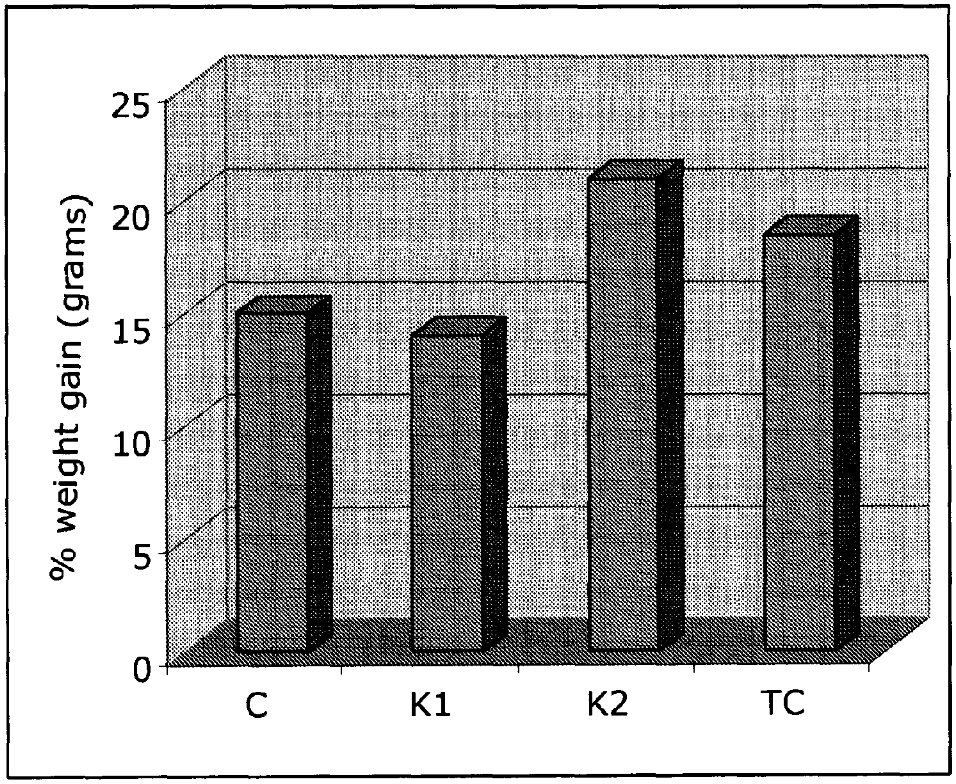
FIG. 4 is a graph illustrating the percent weight gain of hybrid striped bass fingerlings on four diets (TC) Trout Chow; (C) a 40/60 Trout Chow-casein mixture; (K1) Trout Chow-casein mixture coated with a low level of the behavior-eliciting composition; and (K2) Trout Chow-casein mixture coated with a high level of the present composition.

One hundred-twenty hybrid striped bass fingerlings were distributed among twelve tanks supplied with recirculating water. The fish were fed 90 grams of food per day for 28 days. They were weighed at the beginning and end of the experiment. Fish eating the casein/TC diet with the high level of coating gained 14.13±2.83 g, compared to the weight gain on Trout Chow of 12.14±2.62 g. Weight gains on the uncoated and medium-level coated casein/TC diet were 10.36±1.47 g and 10.21±0.63 g, respectively. FIG. 4 shows the percent weight gains of the hybrid striped bass on each of the diets. This experiment illustrates that the fish eating the casein/TC diet with the high level of coating not only gained more weight than those on the uncoated diet, but also gained more weight than those fish eating Trout Chow.

TABLE 2

| Casein diet composition (g/100 g)* | |
|---|---|
| Casein | 36.50 |
| Cornstarch | 4.60 |
| Cellulose | 32.40 |
| Fed. Vit. #30 | 0.20 |
| Ascorbic Acid (coated) | 0.10 |
| Chlorine Cl | 0.20 |
| NaCl | 0.75 |

TABLE 2-continued

| Casein diet composition (g/100 g)* | |
|---|---|
| USWF Mineral | 0.05 |
| Menhaden oil | 14.20 |
| CMC | 2.00 |

*Experiments with 40/60 Trout Chow/Casein Diet

The above mentioned diets had a protein level of 35% and contained 3.5 kcal/g.

Example 6

Figure 5:
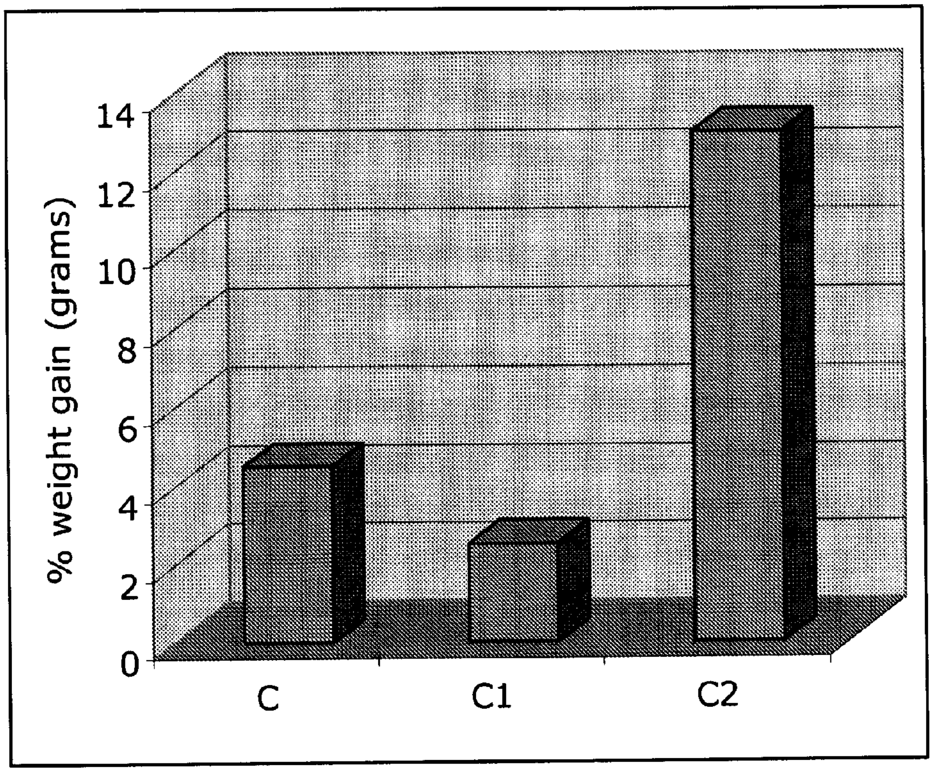
FIG. 5 is a graph illustrating the percent weight gain (g) of hybrid striped bass fingerlings in three diets: (C) casein; (C1) casein coated with a low level of the behavior-eliciting composition; and (C2) casein coated with a high level of the present composition.

A casein diet (with no added Trout Chow) was coated with the fathead minnow (FHM) derived behavior-eliciting composition, and a poultry meal diet was coated similarly or with a 2-fold diluted FHM composition. Weight gains on these diets were compared to weight gains by fish eating uncoated diets. The ingredients of the poultry diet are listed in Table 3. Twenty four tanks of 10 hybrid striped bass fingerlings each were used. Three tanks of fish were fed Trout Chow (Purina Mills LLC, AQUAMAX). It should be noted that the fish had already become acclimated to a Trout Chow diet, so the latter three groups of fish did not require any time to adjust to a new diet. Groups of 3 tanks were fed the casein diet with no coating (C); an intermediate level of coating with the present invention (C1); and a high level of coating with the present invention (C2). The coating levels were the same as those used in Example 5. The experiment was continued for 34 days. The results are shown in FIG. 5.

Figure 6:
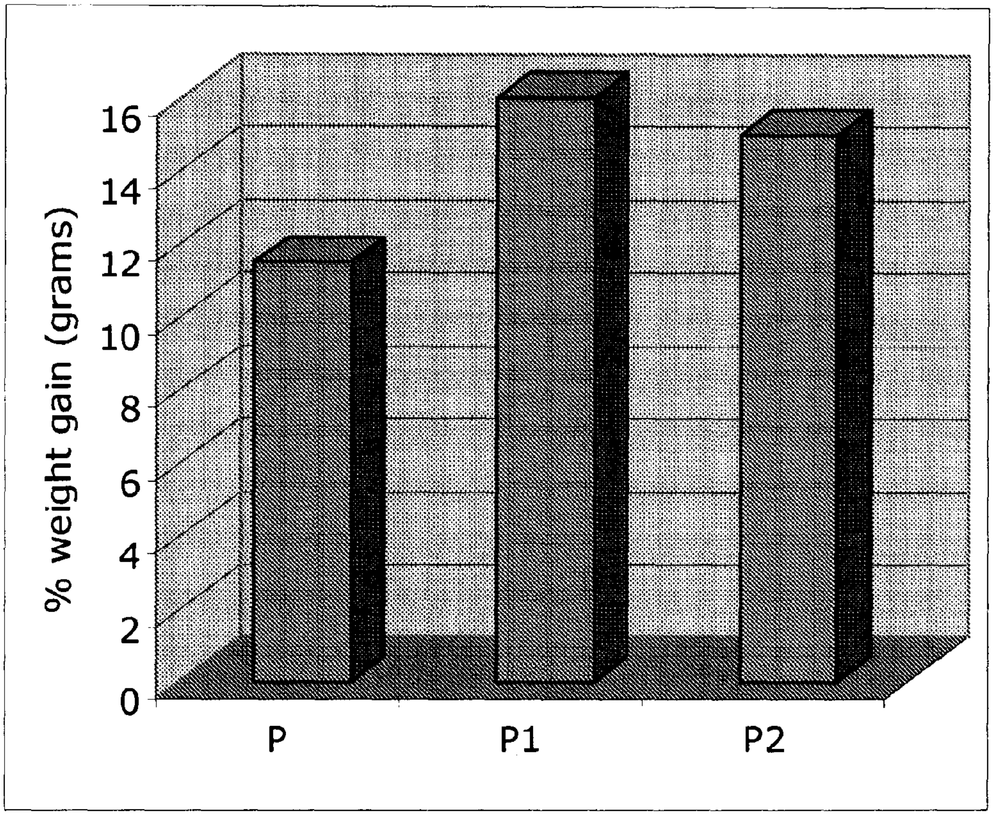
FIG. 6 is a graph illustrating the percent weight gain of hybrid striped bass fingerlings on three diets: (P) and uncoated poultry diet; (P1) a poultry diet coated with low level of the present composition; and (P2) a poultry diet coated with a high level of the behavior-eliciting composition.

Although the fish did quite well on the Trout Chow, as expected, the primary experiment was to determine the effect the behavior-eliciting composition coating had on the lower-cost, less-palatable casein and poultry diets. Three tanks of fish were fed Poultry pellets (Ziegler Brothers, Gardeners Pa.). Groups of 3 tanks were fed the Poultry diet with no coating (P); an intermediate level of coating with the present invention (P1); and a high level of coating with the present invention (P2). The coating levels were the same as those used in Example 5. The experiment/feeding was continued for 34 days. There was significant filamentous growth in the tanks, likely the result of low-level fungal or bacterial contamination of the Poultry pellets not controlled in the manufacture of the pellets (Ziegler Brothers, Gardeners Pa.). However, as shown in FIG. 6, the fish did gain more weight on the poultry diet as a function of the behavior-eliciting coating the Poultry pellets with the composition. Fish eating the Poultry diet did gain slightly less weight on the diet with the high level of coating compared to those eating the Poultry diet with the lower level coating, but the difference was not significant. Both levels of coating exhibited ~2% weight gains over uncoated diet. FIGS. 5 and 6 summarize the above mentioned data.

TABLE 3

| Poultry diet composition (g/100 g)* | |
|---|---|
| Poultry meal | 52.00 |
| Wheat middlings | 28.00 |
| Fed. Vit. #30 | 0.20 |
| Ascorbic acid | 0.10 |
| Chlorine Cl | 0.20 |
| NaCl | 0.75 |
| USWF Mineral | 0.05 |
| Menhaden oil | 15.00 |
| CMC | 2.00 |

*amounts of poultry meal, salt and menhaden oil varied as a function of the protein, lipid and fiber levels of ingredients used The above diet had a protein level of 35% and contained 3.5 kcal/g.

Example 7

Figure 7:
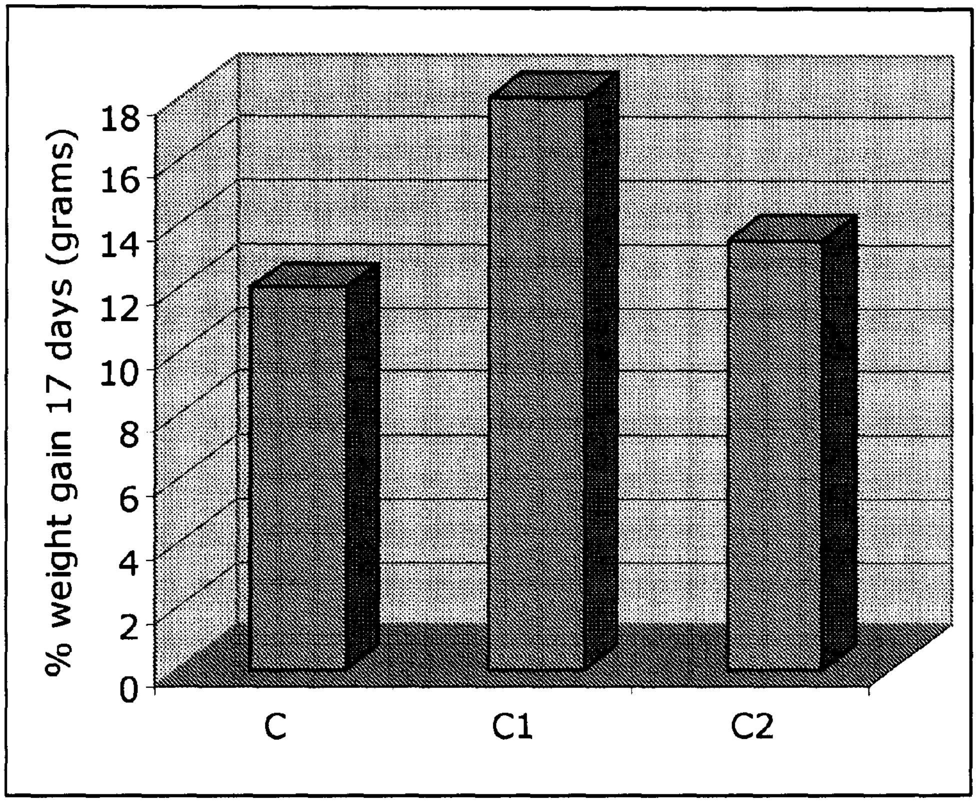
FIG. 7 is a graph illustrating the percent weight gain of hybrid striped bass fry after 17 days of feeding on three diets: (C) a casein diet; (C1) casein coated with a low level of the present composition containing fathead minnow bacteria; and (C2) casein coated with a high level of the present composition containing fathead minnow bacteria.
Figure 8:
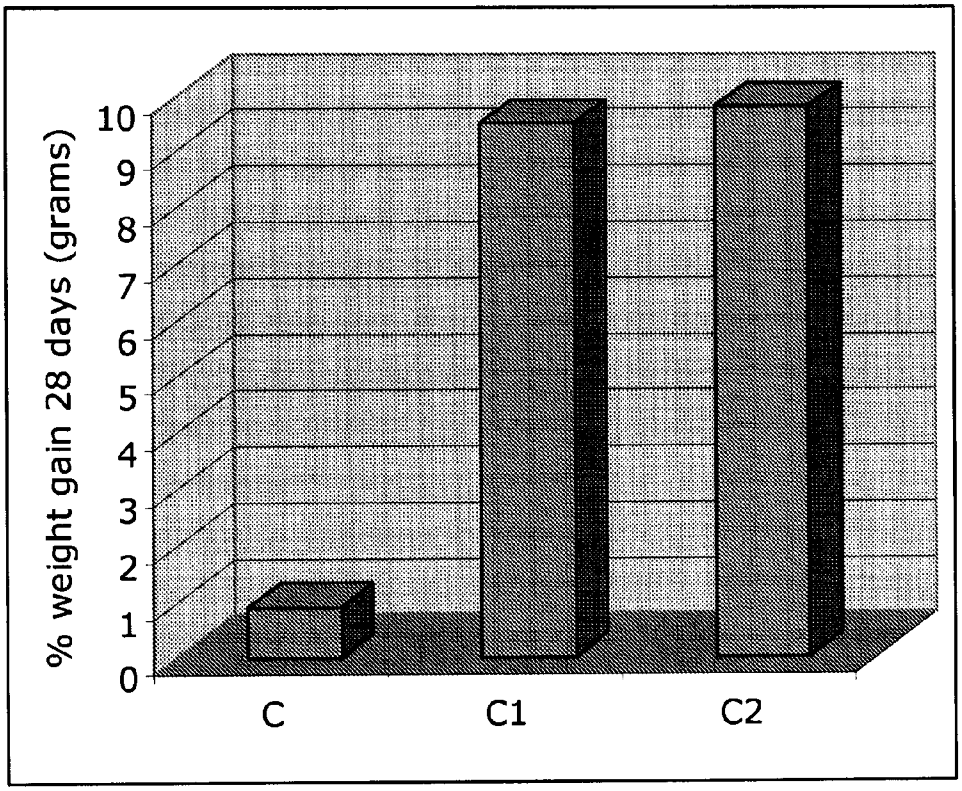
FIG. 8 is a graph illustrating the percent weight gain of the same hybrid striped bass fry as shown in FIG. 6, but weights shown are after 28 days of feeding the three diets: (C) a casein diet; (C1) casein coated with a low level of the present composition containing fathead minnow bacteria; (C2) casein coated with a high level of the present composition containing fathead minnow bacteria.

The tests of the casein diet used in Example 5 (no Trout Chow mixed with it) were repeated but with smaller fish (beginning weights about 0.6 g compared to the average beginning weight of about 10 g in Example 5. Ninety fish were weighed and distributed among 9 tanks Groups of 3 tanks were fed either the plain casein pellets (C) or top-coated pellets at low (C1) and high levels (C2). Fish were weighed at the end of 17 days (FIG. 7) and 28 days (FIG. 8). The experiment was terminated at the end of 28 days because the fish were beginning to appear unhealthy on this diet. The coated casein pellets allowed greater weight gain at 17 days (FIG. 7) and greater weight retention at 28 days (FIG. 8). In contrast, those fish on the uncoated diet lost almost all the weight they had gained previously.

Example 8

Sequences Encoding Portions of 16S RNA Obtained from Bacteria Isolated According to the Present Invention Bacteria were isolated from Bluegills (BR), Fathead Minnows (FHM), Mosquitofish (Gam), and Golden Shiners (GS) in accordance with the techniques described in the instant application. DNA was amplified and PCR products were sequenced essentially as previously described (see Bano et al., 2007). Briefly, bacteria were collected from incubations by filtration through 0.22 μm pore size Sterivex cartridge filters (Millipore; Billerica, Mass.). DNA extraction was completed using the MoBio PowerSoil DNA Extraction Kit. DNA was amplified using Bacteria-specific 16S rRNA primers 27F/1492R (Baker et al., 2003), cloned with the TOPO TA cloning kit (Invitrogen; Carlsbad, Calif.) using vector and *E. coli* competent cells. Clones were selected randomly and sequenced by Genewiz (South Plainfield, N.J.).

Results were compared to the sequences available at the Ribosomal Database Project website (http://rdp.cme.msu.edu/, Cole et al., 2008)

TABLE 4 presents summary data for the bacteria that were associated with the indicated fish. SEQ ID NOs:1-23 are sequences obtained from “Br” or bluegill-associated bacteria. SEQ ID NOs:24-37 are from “FHM” or fathead minnow-associated bacteria. SEQ ID NOs:38-76 are from “Gam” or mosquitofish, or *Gambusia*-associated bacteria. SEQ ID NOs:77-81 are from “GS” is golden shiner-associated bacteria. For each SEQ ID NO, the names and accession numbers for 10 of the closest matching 16S RNA sequences are indicated.

TABLE 4

| SEQ | RDP_ID | Identity | Match Name | Match Name | Access. # |
|---|---|---|---|---|---|
| 1 | S000967841 | 99.224 | *Aeromonas* sp. DH46 | EU260226 | |
| 1 | S000967819 | 99.187 | *Aeromonas* sp. DH14 | EU260204 | |
| 1 | S000705518 | 93.356 | uncult. bac. | aab57c04 | DQ813907 |
| 1 | S000705477 | 93.356 | uncult. bac. | aaa26g10 | DQ813866 |
| 1 | S000705469 | 93.356 | uncult. bac. | aaa25h11 | DQ813858 |
| 1 | S000438730 | 93.356 | *Aeromonas* sp. ’ | CDC 787-80’ | U88662 |
| 1 | S000428865 | 93.356 | *Aeromonas jandaei* | B10 | AF099026 |
| 1 | S000428864 | 93.356 | *Aeromonas jandaei* | M34 | AF099025 |
| 1 | S000008085 | 93.356 | *Aeromonas jandaei* (T) | ATCC 49568T | X74678 |
| 1 | S000005395 | 93.356 | *Aeromonas* sp. RC278 | RC278(MM85) | AF063003 |
| 2 | S000705798 | 93.266 | uncult. bac. | aab65b03 | DQ814187 |
| 2 | S000705528 | 93.266 | uncult. bac. | aab57d03 | DQ813917 |
| 2 | S000705518 | 93.266 | uncult. bac. | aab57c04 | DQ813907 |
| 2 | S000705469 | 93.266 | uncult. bac. | aaa25h11 | DQ813858 |
| 2 | S000438730 | 93.266 | *Aeromonas* sp. ’ | CDC 787-80’ | U88662 |
| 2 | S000428865 | 93.266 | *Aeromonas jandaei* | B10 | AF099026 |
| 2 | S000428864 | 93.266 | *Aeromonas jandaei* | M34 | AF099025 |
| 2 | S000008085 | 93.266 | *Aeromonas jandaei* (T) | ATCC 49568T | X74678 |
| 2 | S000005395 | 93.266 | *Aeromonas* sp. RC278 | RC278(MM85) | AF063003 |
| 2 | S000705477 | 93.154 | uncult. bac. | aaa26g10 | DQ813866 |
| 3 | S000967819 | 99.674 | *Aeromonas* sp. DH14 | EU260204 | |
| 3 | S000456820 | 99.365 | *Aeromonas* sp. ’ | 10.5 MW-3’ | AY826604 |
| 3 | S000967841 | 99.214 | *Aeromonas* sp. DH46 | EU260226 | |
| 3 | S000458103 | 99.005 | *Aeromonas veronii* | N63 | AB182225 |
| 3 | S000458050 | 99.005 | *Aeromonas veronii* | N09 | AB182172 |
| 3 | S000458110 | 99 | *Aeromonas veronii* | N70 | AB182232 |
| 3 | S000458040 | 99 | *Aeromonas veronii* | 105F | AB182099 |
| 3 | S000458039 | 99 | *Aeromonas veronii* | 104F | AB182098 |
| 3 | S000458034 | 99 | *Aeromonas veronii* | 99F | AB182093 |
| 3 | S000706450 | 96.34 | uncult. bac. | aab54c05 | DQ814839 |
| 4 | S000967819 | 100 | *Aeromonas* sp. DH14 | EU260204 | |
| 4 | S000967841 | 99.843 | *Aeromonas* sp. DH46 | EU260226 | |
| 4 | S000705528 | 94.138 | uncult. bac. | aab57d03 | DQ813917 |
| 4 | S000705518 | 94.138 | uncult. bac. | aab57c04 | DQ813907 |
| 4 | S000705469 | 94.138 | uncult. bac. | aaa25h11 | DQ813858 |
| 4 | S000438730 | 94.138 | *Aeromonas* sp. ’ | CDC 787-80’ | U88662 |
| 4 | S000428865 | 94.138 | *Aeromonas jandaei* | B10 | AF099026 |
| 4 | S000428864 | 94.138 | *Aeromonas jandaei* | M34 | AF099025 |
| 4 | S000005395 | 94.138 | *Aeromonas* sp. RC278 | RC278(MM85) | AF063003 |
| 4 | S000705477 | 94.025 | uncult. bac. | aaa26g10 | DQ813866 |
| 5 | S000705798 | 98.405 | uncult. bac. | aab65b03 | DQ814187 |
| 5 | S000705528 | 98.405 | uncult. bac. | aab57d03 | DQ813917 |
| 5 | S000705518 | 98.405 | uncult. bac. | aab57c04 | DQ813907 |
| 5 | S000705477 | 98.405 | uncult. bac. | aaa26g10 | DQ813866 |
| 5 | S000705469 | 98.405 | uncult. bac. | aaa25h11 | DQ813858 |
| 5 | S000438730 | 98.405 | *Aeromonas* sp. ’ | CDC 787-80’ | U88662 |

TABLE 4-continued

| SEQ | RDP_ID | Identity | Match Name | Match Name | Access. # |
|---|---|---|---|---|---|
| 5 | S000428865 | 98.405 | *Aeromonas jandaei* | B10 | AF099026 |
| 5 | S000428864 | 98.405 | *Aeromonas jandaei* | M34 | AF099025 |
| 5 | S000008085 | 98.405 | *Aeromonas jandaei* (T) | ATCC 49568T | X74678 |
| 5 | S000005395 | 98.405 | *Aeromonas* sp. RC278 | RC278(MM85) | AF063003 |
| 6 | S000705798 | 97.816 | uncult. bac. | aab65b03 | DQ814187 |
| 6 | S000705528 | 97.816 | uncult. bac. | aab57d03 | DQ813917 |
| 6 | S000705518 | 97.816 | uncult. bac. | aab57c04 | DQ813907 |
| 6 | S000705477 | 97.816 | uncult. bac. | aaa26g10 | DQ813866 |
| 6 | S000705469 | 97.816 | uncult. bac. | aaa25h11 | DQ813858 |
| 6 | S000438730 | 97.816 | *Aeromonas* sp. ' | CDC 787-80' | U88662 |
| 6 | S000428865 | 97.816 | *Aeromonas jandaei* | B10 | AF099026 |
| 6 | S000428864 | 97.816 | *Aeromonas jandaei* | M34 | AF099025 |
| 6 | S000008085 | 97.816 | *Aeromonas jandaei* (T) | ATCC 49568T | X74678 |
| 6 | S000005395 | 97.816 | *Aeromonas* sp. RC278 | RC278(MM85) | AF063003 |
| 7 | S000967819 | 100 | *Aeromonas* sp. DH14 | EU260204 | |
| 7 | S000705518 | 92.189 | uncult. bac. | aab57c04 | DQ813907 |
| 7 | S000705477 | 92.189 | uncult. bac. | aaa26g10 | DQ813866 |
| 7 | S000705469 | 92.189 | uncult. bac. | aaa25h11 | DQ813858 |
| 7 | S000438730 | 92.189 | *Aeromonas* sp. ' | CDC 787-80' | U88662 |
| 7 | S000428865 | 92.189 | *Aeromonas jandaei* | B10 | AF099026 |
| 7 | S000428864 | 92.189 | *Aeromonas jandaei* | M34 | AF099025 |
| 7 | S000008085 | 92.189 | *Aeromonas jandaei* (T) | ATCC 49568T | X74678 |
| 7 | S000005395 | 92.189 | *Aeromonas* sp. RC278 | RC278(MM85) | AF063003 |
| 7 | S000705497 | 92.061 | uncult. bac. | aaa28h03 | DQ813886 |
| 8 | S000967819 | 100 | *Aeromonas* sp. DH14 | EU260204 | |
| 8 | S000705518 | 90.805 | uncult. bac. | aab57c04 | DQ813907 |
| 8 | S000705477 | 90.805 | uncult. bac. | aaa26g10 | DQ813866 |
| 8 | S000705469 | 90.805 | uncult. bac. | aaa25h11 | DQ813858 |
| 8 | S000438730 | 90.805 | *Aeromonas* sp. ' | CDC 787-80' | U88662 |
| 8 | S000428865 | 90.805 | *Aeromonas jandaei* | B10 | AF099026 |
| 8 | S000428864 | 90.805 | *Aeromonas jandaei* | M34 | AF099025 |
| 8 | S000008085 | 90.805 | *Aeromonas jandaei* (T) | ATCC 49568T | X74678 |
| 8 | S000005395 | 90.805 | *Aeromonas* sp. RC278 | RC278(MM85) | AF063003 |
| 8 | S000705497 | 90.69 | uncult. bac. | aaa28h03 | DQ813886 |
| 9 | S000967841 | 99.689 | *Aeromonas* sp. DH46 | EU260226 | |
| 9 | S000967819 | 99.674 | *Aeromonas* sp. DH14 | EU260204 | |
| 9 | S001265172 | 91.716 | *Aeromonas* sp. MCCB 141 | FJ573178 | |
| 9 | S000705477 | 91.716 | uncult. bac. | aaa26g10 | DQ813866 |
| 9 | S000705469 | 91.716 | uncult. bac. | aaa25h11 | DQ813858 |
| 9 | S000438730 | 91.716 | *Aeromonas* sp. ' | CDC 787-80' | U88662 |
| 9 | S000428865 | 91.716 | *Aeromonas jandaei* | B10 | AF099026 |
| 9 | S000428864 | 91.716 | *Aeromonas jandaei* | M34 | AF099025 |
| 9 | S000008085 | 91.716 | *Aeromonas jandaei* (T) | ATCC 49568T | X74678 |
| 9 | S000005395 | 91.716 | *Aeromonas* sp. RC278 | RC278(MM85) | AF063003 |
| 10 | S000967841 | 99.844 | *Aeromonas* sp. DH46 | EU260226 | |
| 10 | S000967819 | 99.837 | *Aeromonas* sp. DH14 | EU260204 | |
| 10 | S000705518 | 97.419 | uncult. bac. | aab57c04 | DQ813907 |
| 10 | S000705477 | 97.419 | uncult. bac. | aaa26g10 | DQ813866 |
| 10 | S000705469 | 97.419 | uncult. bac. | aaa25h11 | DQ813858 |
| 10 | S000438730 | 97.419 | *Aeromonas* sp. ' | CDC 787-80' | U88662 |
| 10 | S000428865 | 97.419 | *Aeromonas jandaei* | B10 | AF099026 |
| 10 | S000428864 | 97.419 | *Aeromonas jandaei* | M34 | AF099025 |
| 10 | S000008085 | 97.419 | *Aeromonas jandaei* (T) | ATCC 49568T | X74678 |
| 10 | S000005395 | 97.419 | *Aeromonas* sp. RC278 | RC278(MM85) | AF063003 |
| 11 | S000705888 | 96.709 | uncult. bac. | aab66d03 | DQ814277 |
| 11 | S000705518 | 96.709 | uncult. bac. | aab57c04 | DQ813907 |
| 11 | S000705477 | 96.709 | uncult. bac. | aaa26g10 | DQ813866 |
| 11 | S000705469 | 96.709 | uncult. bac. | aaa25h11 | DQ813858 |
| 11 | S000438730 | 96.709 | *Aeromonas* sp. ' | CDC 787-80' | U88662 |
| 11 | S000428865 | 96.709 | *Aeromonas jandaei* | B10 | AF099026 |
| 11 | S000428864 | 96.709 | *Aeromonas jandaei* | M34 | AF099025 |
| 11 | S000008085 | 96.709 | *Aeromonas jandaei* (T) | ATCC 49568T | X74678 |
| 11 | S000005395 | 96.709 | *Aeromonas* sp. RC278 | RC278(MM85) | AF063003 |
| 11 | S000706024 | 96.587 | uncult. bac. | aab68c10 | DQ814413 |
| 12 | S000705528 | 97.335 | uncult. bac. | aab57d03 | DQ813917 |
| 12 | S000705518 | 97.335 | uncult. bac. | aab57c04 | DQ813907 |
| 12 | S000705477 | 97.335 | uncult. bac. | aaa26g10 | DQ813866 |
| 12 | S000705469 | 97.335 | uncult. bac. | aaa25h11 | DQ813858 |
| 12 | S000438730 | 97.335 | *Aeromonas* sp. ' | CDC 787-80' | U88662 |
| 12 | S000428865 | 97.335 | *Aeromonas jandaei* | B10 | AF099026 |
| 12 | S000428864 | 97.335 | *Aeromonas jandaei* | M34 | AF099025 |
| 12 | S000008085 | 97.335 | *Aeromonas jandaei* (T) | ATCC 49568T | X74678 |
| 12 | S000005395 | 97.335 | *Aeromonas* sp. RC278 | RC278(MM85) | AF063003 |
| 12 | S000705633 | 97.208 | uncult. bac. | aab58e12 | DQ814022 |
| 13 | S000705798 | 97.576 | uncult. bac. | aab65b03 | DQ814187 |
| 13 | S000705528 | 97.576 | uncult. bac. | aab57d03 | DQ813917 |
| 13 | S000705518 | 97.576 | uncult. bac. | aab57c04 | DQ813907 |
| 13 | S000705477 | 97.576 | uncult. bac. | aaa26g10 | DQ813866 |

TABLE 4-continued

| SEQ | RDP_ID | Identity | Match Name | Match Name | Access. # |
|---|---|---|---|---|---|
| 13 | S000705469 | 97.576 | uncult. bac. | aaa25h11 | DQ813858 |
| 13 | S000438730 | 97.576 | *Aeromonas* sp. ' | CDC 787-80' | U88662 |
| 13 | S000428865 | 97.576 | *Aeromonas jandaei* | B10 | AF099026 |
| 13 | S000428864 | 97.576 | *Aeromonas jandaei* | M34 | AF099025 |
| 13 | S000008085 | 97.576 | *Aeromonas jandaei* (T) | ATCC 49568T | X74678 |
| 13 | S000005395 | 97.576 | *Aeromonas* sp. RC278 | RC278(MM85) | AF063003 |
| 14 | S000967819 | 100 | *Aeromonas* sp. DH14 | EU260204 | |
| 14 | S000708278 | 93.132 | uncult. bac. | aaa97a08 | DQ816667 |
| 14 | S000705477 | 93.132 | uncult. bac. | aaa26g10 | DQ813866 |
| 14 | S000705469 | 93.132 | uncult. bac. | aaa25h11 | DQ813858 |
| 14 | S000438730 | 93.132 | *Aeromonas* sp. ' | CDC 787-80' | U88662 |
| 14 | S000428865 | 93.132 | *Aeromonas jandaei* | B10 | AF099026 |
| 14 | S000428864 | 93.132 | *Aeromonas jandaei* | M34 | AF099025 |
| 14 | S000008085 | 93.132 | *Aeromonas jandaei* (T) | ATCC 49568T | X74678 |
| 14 | S000005395 | 93.132 | *Aeromonas* sp. RC278 | RC278(MM85) | AF063003 |
| 14 | S001185126 | 93.122 | uncult. bac. | Bul2ab09 | FJ228813 |
| 15 | S000705769 | 97.845 | uncult. bac. | aab60f07 | DQ814158 |
| 15 | S000705528 | 97.845 | uncult. bac. | aab57d03 | DQ813917 |
| 15 | S000705518 | 97.845 | uncult. bac. | aab57c04 | DQ813907 |
| 15 | S000705477 | 97.845 | uncult. bac. | aaa26g10 | DQ813866 |
| 15 | S000705469 | 97.845 | uncult. bac. | aaa25h11 | DQ813858 |
| 15 | S000438730 | 97.845 | *Aeromonas* sp. ' | CDC 787-80' | U88662 |
| 15 | S000428865 | 97.845 | *Aeromonas jandaei* | B10 | AF099026 |
| 15 | S000428864 | 97.845 | *Aeromonas jandaei* | M34 | AF099025 |
| 15 | S000008085 | 97.845 | *Aeromonas jandaei* (T) | ATCC 49568T | X74678 |
| 15 | S000005395 | 97.845 | *Aeromonas* sp. RC278 | RC278(MM85) | AF063003 |
| 16 | S000705528 | 96.658 | uncult. bac. | aab57d03 | DQ813917 |
| 16 | S000705518 | 96.658 | uncult. bac. | aab57c04 | DQ813907 |
| 16 | S000705477 | 96.658 | uncult. bac. | aaa26g10 | DQ813866 |
| 16 | S000705469 | 96.658 | uncult. bac. | aaa25h11 | DQ813858 |
| 16 | S000438730 | 96.658 | *Aeromonas* sp. ' | CDC 787-80' | U88662 |
| 16 | S000428865 | 96.658 | *Aeromonas jandaei* | B10 | AF099026 |
| 16 | S000428864 | 96.658 | *Aeromonas jandaei* | M34 | AF099025 |
| 16 | S000008085 | 96.658 | *Aeromonas jandaei* (T) | ATCC 49568T | X74678 |
| 16 | S000005395 | 96.658 | *Aeromonas* sp. RC278 | RC278(MM85) | AF063003 |
| 16 | S000705497 | 96.53 | uncult. bac. | aaa28h03 | DQ813886 |
| 17 | S000456820 | 99.365 | *Aeromonas* sp. ' | 10.5 MW-3' | AY826604 |
| 17 | S000705528 | 91.825 | uncult. bac. | aab57d03 | DQ813917 |
| 17 | S000705518 | 91.825 | uncult. bac. | aab57c04 | DQ813907 |
| 17 | S000705469 | 91.825 | uncult. bac. | aaa25h11 | DQ813858 |
| 17 | S000438730 | 91.825 | *Aeromonas* sp. ' | CDC 787-80' | U88662 |
| 17 | S000428865 | 91.825 | *Aeromonas jandaei* | B10 | AF099026 |
| 17 | S000428864 | 91.825 | *Aeromonas jandaei* | M34 | AF099025 |
| 17 | S000393862 | 91.825 | *Aeromonas veronii* | LMG13695 | 2 |
| 17 | S000008085 | 91.825 | *Aeromonas jandaei* (T) | ATCC 49568T | X74678 |
| 17 | S000005395 | 91.825 | *Aeromonas* sp. RC278 | RC278(MM85) | AF063003 |
| 18 | S000456820 | 99.365 | *Aeromonas* sp. ' | 10.5 MW-3' | AY826604 |
| 18 | S001549380 | 94.731 | *Aeromonas jandaei* | pW23 | FJ940830 |
| 18 | S001549354 | 94.731 | *Aeromonas jandaei* | 4pM28 | FJ940804 |
| 18 | S000705469 | 94.731 | uncult. bac. | aaa25h11 | DQ813858 |
| 18 | S000438730 | 94.731 | *Aeromonas* sp. ' | CDC 787-80' | U88662 |
| 18 | S000428865 | 94.731 | *Aeromonas jandaei* | B10 | AF099026 |
| 18 | S000428864 | 94.731 | *Aeromonas jandaei* | M34 | AF099025 |
| 18 | S000393862 | 94.731 | *Aeromonas veronii* | LMG13695 | 2 |
| 18 | S000008085 | 94.731 | *Aeromonas jandaei* (T) | ATCC 49568T | X74678 |
| 18 | S000005395 | 94.731 | *Aeromonas* sp. RC278 | RC278(MM85) | AF063003 |
| 19 | S000035980 | 99.751 | *Aeromonas* sp. Lgg5.7 | AJ489337 | |
| 19 | S000456820 | 99.365 | *Aeromonas* sp. ' | 10.5 MW-3' | AY826604 |
| 19 | S000458104 | 98.993 | *Aeromonas veronii* | N64 | AB182226 |
| 19 | S000458117 | 98.99 | *Aeromonas veronii* | N77 | AB182239 |
| 19 | S000458074 | 98.988 | *Aeromonas veronii* | N34 | AB182196 |
| 19 | S000458025 | 98.986 | *Aeromonas veronii* | 90F | AB182084 |
| 19 | S000691722 | 98.942 | bacterium SL2.12 | DQ517031 | |
| 19 | S000030133 | 98.936 | *Aeromonas veronii* | S4M13 | AF472504 |
| 19 | S000458071 | 98.921 | *Aeromonas veronii* | N31 | AB182193 |
| 19 | S000967819 | 98.042 | *Aeromonas* sp. DH14 | EU260204 | |
| 20 | S000967841 | 99.844 | *Aeromonas* sp. DH46 | EU260226 | |
| 20 | S000967819 | 99.837 | *Aeromonas* sp. DH14 | EU260204 | |
| 20 | S000967846 | 99.701 | *Aeromonas* sp. DH57 | EU260231 | |
| 20 | S000705518 | 98.307 | uncult. bac. | aab57c04 | DQ813907 |
| 20 | S000705469 | 98.307 | uncult. bac. | aaa25h11 | DQ813858 |
| 20 | S000438730 | 98.307 | *Aeromonas* sp. ' | CDC 787-80' | U88662 |
| 20 | S000428865 | 98.307 | *Aeromonas jandaei* | B10 | AF099026 |
| 20 | S000428864 | 98.307 | *Aeromonas jandaei* | M34 | AF099025 |
| 20 | S000008085 | 98.307 | *Aeromonas jandaei* (T) | ATCC 49568T | X74678 |
| 20 | S000005395 | 98.307 | *Aeromonas* sp. RC278 | RC278(MM85) | AF063003 |
| 21 | S000967819 | 99.674 | *Aeromonas* sp. DH14 | EU260204 | |
| 21 | S000708720 | 91.071 | uncult. bac. | aaa95h10 | DQ817109 |

TABLE 4-continued

| SEQ | RDP_ID | Identity | Match Name | Match Name | Access. # |
|---|---|---|---|---|---|
| 21 | S000705518 | 90.96 | uncult. bac. | aab57c04 | DQ813907 |
| 21 | S000705469 | 90.96 | uncult. bac. | aaa25h11 | DQ813858 |
| 21 | S000438730 | 90.96 | *Aeromonas* sp. ' | CDC 787-80' | U88662 |
| 21 | S000428865 | 90.96 | *Aeromonas jandaei* | B10 | AF099026 |
| 21 | S000428864 | 90.96 | *Aeromonas jandaei* | M34 | AF099025 |
| 21 | S000008085 | 90.96 | *Aeromonas jandaei* (T) | ATCC 49568T | X74678 |
| 21 | S000005395 | 90.96 | *Aeromonas* sp. RC278 | RC278(MM85) | AF063003 |
| 21 | S000705477 | 90.848 | uncult. bac. | aaa26g10 | DQ813866 |
| 22 | S000967819 | 99.349 | *Aeromonas* sp. DH14 | EU260204 | |
| 22 | S000705477 | 89.047 | uncult. bac. | aaa26g10 | DQ813866 |
| 22 | S000705528 | 88.938 | uncult. bac. | aab57d03 | DQ813917 |
| 22 | S000705469 | 88.938 | uncult. bac. | aaa25h11 | DQ813858 |
| 22 | S000438730 | 88.938 | *Aeromonas* sp. ' | CDC 787-80' | U88662 |
| 22 | S000428865 | 88.938 | *Aeromonas jandaei* | B10 | AF099026 |
| 22 | S000428864 | 88.938 | *Aeromonas jandaei* | M34 | AF099025 |
| 22 | S000008085 | 88.938 | *Aeromonas jandaei* (T) | ATCC 49568T | X74678 |
| 22 | S000005395 | 88.938 | *Aeromonas* sp. RC278 | RC278(MM85) | AF063003 |
| 22 | S000705518 | 88.828 | uncult. bac. | aab57c04 | DQ813907 |
| 23 | S000409954 | 99.267 | uncult. bac. | ABW-130 | AY456860 |
| 23 | S000619307 | 98.504 | uncult. bac. | BPH1050 | DQ221371 |
| 23 | S001352807 | 97.796 | *Acinetobacter* sp. WH084 | FJ866707 | |
| 23 | S001014738 | 97.758 | *Acinetobacter tjernbergiae* | DSM14971 | EF611415 |
| 23 | S000619314 | 97.525 | uncult. bac. | BPH2C9003 | DQ221378 |
| 23 | S000619245 | 97.5 | uncult. bac. | BPH1C15001 | DQ221309 |
| 23 | S000619246 | 97.5 | uncult. bac. | BPH1C15002 | DQ221310 |
| 23 | S001352761 | 97.4 | *Acinetobacter* sp. WH374 | FJ866661 | |
| 23 | S000619249 | 97 | uncult. bac. | BPH1C15005 | DQ221313 |
| 23 | S000619262 | 96.509 | uncult. bac. | BPH1C20002 | DQ221326 |
| 24 | S000915376 | 99.767 | uncult. beta proteobacterium | MS158A1_C01 | EF705161 |
| 24 | S000386190 | 99.569 | *Acidovorax* sp. 12M7 | AB120338 | |
| 24 | S000912964 | 99.551 | uncult. beta proteobacterium | MS089A1_C09 | EF702749 |
| 24 | S000915409 | 99.549 | uncult. beta proteobacterium | MS158A1_F06 | EF705194 |
| 24 | S000608601 | 98.901 | uncult. bac. | Ri222 | AM110029 |
| 24 | S001331720 | 96.092 | *Acidovorax* sp. Z022 | FN293049 | |
| 24 | S001517497 | 95.687 | uncult. bac. | nbw346a08c1 | GQ091433 |
| 24 | S001525581 | 95.573 | uncult. bac. | nbw511f09c1 | GQ099517 |
| 24 | S001519854 | 95.573 | uncult. bac. | nbw425b04c1 | GQ093790 |
| 24 | S001513669 | 95.46 | uncult. bac. | nbw304e10c1 | GQ087605 |
| 25 | S000915376 | 99.767 | uncult. beta proteobacterium | MS158A1_C01 | EF705161 |
| 25 | S000386190 | 99.569 | *Acidovorax* sp. 12M7 | AB120338 | |
| 25 | S001082320 | 98.983 | uncult. *Acidovorax* sp. | NSR3Q1b11 | EU629817 |
| 25 | S000608601 | 98.901 | uncult. bac. | Ri222 | AM110029 |
| 25 | S000915409 | 98.799 | uncult. beta proteobacterium | MS158A1_F06 | EF705194 |
| 25 | S001331720 | 95.243 | *Acidovorax* sp. Z022 | FN293049 | |
| 25 | S001517497 | 94.537 | uncult. bac. | nbw346a08c1 | GQ091433 |
| 25 | S001522360 | 94.537 | uncult. bac. | nbw446b08c1 | GQ096296 |
| 25 | S001525581 | 94.537 | uncult. bac. | nbw511f09c1 | GQ099517 |
| 25 | S001040152 | 91.828 | uncult. bac. | PA31 | EU743899 |
| 26 | S000894766 | 99.58 | uncult. *Acidovorax* sp. | 40_4 | AM779871 |
| 26 | S000915376 | 99.534 | uncult. beta proteobacterium | MS158A1_C01 | EF705161 |
| 26 | S000386190 | 99.353 | *Acidovorax* sp. 12M7 | AB120338 | |
| 26 | S000912964 | 99.254 | uncult. beta proteobacterium | MS089A1_C09 | EF702749 |
| 26 | S001082320 | 98.99 | uncult. *Acidovorax* sp. | NSR3Q1b11 | EU629817 |
| 26 | S000608601 | 98.901 | uncult. bac. | Ri222 | AM110029 |
| 26 | S001331720 | 97.333 | *Acidovorax* sp. Z022 | FN293049 | |
| 26 | S001517497 | 96.981 | uncult. bac. | nbw346a08c1 | GQ091433 |
| 26 | S000999969 | 96.977 | uncult. bac. | Oh3137A12D | EU137452 |
| 26 | S001513669 | 96.739 | uncult. bac. | nbw304e10c1 | GQ087605 |
| 27 | S000915376 | 99.767 | uncult. beta proteobacterium | MS158A1_C01 | EF705161 |
| 27 | S000386190 | 99.569 | *Acidovorax* sp. 12M7 | AB120338 | |
| 27 | S000915409 | 99.099 | uncult. beta proteobacterium | MS158A1_F06 | EF705194 |
| 27 | S000608601 | 98.901 | uncult. bac. | Ri222 | AM110029 |
| 27 | S001331720 | 95.103 | *Acidovorax* sp. Z022 | FN293049 | |
| 27 | S001034645 | 94.773 | uncult. *Acidovorax* sp. | 1P-2-I01 | EU705064 |
| 27 | S001034587 | 94.773 | uncult. *Acidovorax* sp. | 1P-2-E06 | EU705006 |
| 27 | S001517497 | 94.576 | uncult. bac. | nbw346a08c1 | GQ091433 |
| 27 | S001525581 | 94.463 | uncult. bac. | nbw511f09c1 | GQ099517 |
| 27 | S001513669 | 94.35 | uncult. bac. | nbw304e10c1 | GQ087605 |
| 28 | S000915376 | 99.767 | uncult. beta | MS158A1_C01 | EF705161 |

TABLE 4-continued

| SEQ | RDP_ID | Identity | Match Name | Match Name | Access. # |
|---|---|---|---|---|---|
| | | | proteobacterium | | |
| 28 | S000678674 | 99.658 | uncult. beta proteobacterium | MTAG33 | AJ964947 |
| 28 | S000386190 | 99.569 | *Acidovorax* sp. 12M7 | AB120338 | |
| 28 | S000915409 | 99.549 | uncult. beta proteobacterium | MS158A1_F06 | EF705194 |
| 28 | S000425538 | 99.451 | uncult. *Acidovorax* sp. | CDBL_06 | AY734546 |
| 28 | S000910961 | 99.425 | uncult. beta proteobacterium | MS001A1_A05 | EF700746 |
| 28 | S000912964 | 99.402 | uncult. beta proteobacterium | MS089A1_C09 | EF702749 |
| 28 | S000608601 | 98.901 | uncult. bac. | Ri222 | AM110029 |
| 28 | S001331720 | 93.964 | *Acidovorax* sp. Z022 | FN293049 | |
| 28 | S001040152 | 92.735 | uncult. bac. | PA31 | EU743899 |
| 29 | S000915376 | 99.767 | uncult. beta proteobacterium | MS158A1_C01 | EF705161 |
| 29 | S000386190 | 99.569 | *Acidovorax* sp. 12M7 | AB120338 | |
| 29 | S000912964 | 99.552 | uncult. beta proteobacterium | MS089A1_C09 | EF702749 |
| 29 | S000915409 | 99.549 | uncult. beta proteobacterium | MS158A1_F06 | EF705194 |
| 29 | S000678674 | 99.487 | uncult. beta proteobacterium | MTAG33 | AJ964947 |
| 29 | S000910961 | 99.283 | uncult. beta proteobacterium | MS001A1_A05 | EF700746 |
| 29 | S000907725 | 99.263 | uncult. beta proteobacterium | MS074A1_A03 | EF697510 |
| 29 | S000608601 | 98.901 | uncult. bac. | Ri222 | AM110029 |
| 29 | S001331720 | 95.991 | *Acidovorax* sp. Z022 | FN293049 | |
| 29 | S001040152 | 92.751 | uncult. bac. | PA31 | EU743899 |
| 30 | S000915376 | 99.534 | uncult. beta proteobacterium | MS158A1_C01 | EF705161 |
| 30 | S000915409 | 99.398 | uncult. beta proteobacterium | MS158A1_F06 | EF705194 |
| 30 | S001331720 | 96.045 | *Acidovorax* sp. Z022 | FN293049 | |
| 30 | S001517497 | 95.608 | uncult. bac. | nbw346a08c1 | GQ091433 |
| 30 | S001525581 | 95.495 | uncult. bac. | nbw511f09c1 | GQ099517 |
| 30 | S001527914 | 95.495 | uncult. bac. | nbw500a08c1 | GQ101850 |
| 30 | S001000142 | 95.495 | uncult. bac. | Oh3127A10C | EU137625 |
| 30 | S000607908 | 95.495 | *Acidovorax* sp. R-24667 | AM084010 | |
| 30 | S001513669 | 95.383 | uncult. bac. | nbw304e10c1 | GQ087605 |
| 30 | S000976862 | 95.383 | uncult. *Acidovorax* sp. | AV_8R-S-F03 | EU341283 |
| 31 | S000915376 | 99.534 | uncult. beta proteobacterium | MS158A1_C01 | EF705161 |
| 31 | S000894766 | 99.37 | uncult. *Acidovorax* sp. | 40_4 | AM779871 |
| 31 | S000386190 | 99.353 | *Acidovorax* sp. 12M7 | AB120338 | |
| 31 | S000915409 | 99.245 | uncult. beta proteobacterium | MS158A1_F06 | EF705194 |
| 31 | S000456780 | 99.176 | *Acidovorax* sp. ' | 14.5 MW-16' | AY826564 |
| 31 | S000894761 | 99.111 | uncult. *Acidovorax* sp. | 14_2 | AM779866 |
| 31 | S000912964 | 99.103 | uncult. beta proteobacterium | MS089A1_C09 | EF702749 |
| 31 | S001082320 | 98.99 | uncult. *Acidovorax* sp. | NSR3Q1b11 | EU629817 |
| 31 | S000608601 | 98.901 | uncult. bac. | Ri222 | AM110029 |
| 31 | S000741955 | 98.687 | uncult. bac. | GL-GLY3 | EF014934 |
| 32 | S000915376 | 99.767 | uncult. beta proteobacterium | MS158A1_C01 | EF705161 |
| 32 | S000386190 | 99.569 | *Acidovorax* sp. 12M7 | AB120338 | |
| 32 | S000912964 | 99.402 | uncult. beta proteobacterium | MS089A1_C09 | EF702749 |
| 32 | S000915409 | 99.249 | uncult. beta proteobacterium | MS158A1_F06 | EF705194 |
| 32 | S000608601 | 98.901 | uncult. bac. | Ri222 | AM110029 |
| 32 | S001331720 | 97.578 | *Acidovorax* sp. Z022 | FN293049 | |
| 32 | S001517497 | 97.126 | uncult. bac. | nbw346a08c1 | GQ091433 |
| 32 | S001522360 | 97.126 | uncult. bac. | nbw446b08c1 | GQ096296 |
| 32 | S000999969 | 97.123 | uncult. bac. | Oh3137A12D | EU137452 |
| 32 | S001525581 | 97.011 | uncult. bac. | nbw511f09c1 | GQ099517 |
| 33 | S000422185 | 100 | bacterium CYB24 | 97619 | AY702867 |
| 33 | S000456855 | 100 | *Acidovorax* sp. ' | 6.5 MW-10' | AY826639 |
| 33 | S000911498 | 99.814 | uncult. beta proteobacterium | MS032A1_A10 | EF701283 |
| 33 | S000751146 | 99.807 | filamentous bacterium J8 | EF016509 | |
| 33 | S000333966 | 99.774 | uncult. bac. | CYB236 | AY645488 |
| 33 | S001277787 | 96.579 | uncult. *Comamonadaceae bacterium* | LW18m-1-58 | EU642288 |
| 33 | S000995842 | 96.579 | *Acidovorax* sp. g32 | EU375647 | |
| 33 | S001576976 | 96.267 | *Acidovorax facilis* | TSWCSN46 | GQ284412 |

TABLE 4-continued

| SEQ | RDP_ID | Identity | Match Name | Match Name | Access. # |
|---|---|---|---|---|---|
| 33 | S000354541 | 96.267 | uncult. bac. | GOUTB4 | AY050592 |
| 33 | S000087791 | 96.267 | unidentified | Ben05B | X86071 |
| 34 | S000915376 | 99.767 | uncult. beta proteobacterium | MS158A1_C01 | EF705161 |
| 34 | S000386190 | 99.569 | *Acidovorax* sp. 12M7 | AB120338 | |
| 34 | S000912964 | 99.402 | uncult. beta proteobacterium | MS089A1_C09 | EF702749 |
| 34 | S000915409 | 99.398 | uncult. beta proteobacterium | MS158A1_F06 | EF705194 |
| 34 | S000608601 | 98.901 | uncult. bac. | Ri222 | AM110029 |
| 34 | S001331720 | 97.988 | *Acidovorax* sp. Z022 | FN293049 | |
| 34 | S001517497 | 97.524 | uncult. bac. | nbw346a08c1 | GQ091433 |
| 34 | S001525581 | 97.406 | uncult. bac. | nbw511f09c1 | GQ099517 |
| 34 | S001527914 | 97.406 | uncult. bac. | nbw500a08c1 | GQ101850 |
| 34 | S001513669 | 97.288 | uncult. bac. | nbw304e10c1 | GQ087605 |
| 35 | S000386190 | 99.569 | *Acidovorax* sp. 12M7 | AB120338 | |
| 35 | S000915376 | 99.534 | uncult. beta proteobacterium | MS158A1_C01 | EF705161 |
| 35 | S000636683 | 99.414 | uncult. bac. | RBL5-15 | DQ323099 |
| 35 | S000915409 | 99.398 | uncult. beta proteobacterium | MS158A1_F06 | EF705194 |
| 35 | S000456780 | 99.176 | *Acidovorax* sp. ' | 14.5 MW-16' | AY826564 |
| 35 | S000894766 | 99.16 | uncult. *Acidovorax* sp. | 40_4 | AM779871 |
| 35 | S000912964 | 99.103 | uncult. beta proteobacterium | MS089A1_C09 | EF702749 |
| 35 | S001082320 | 98.983 | uncult. *Acidovorax* sp. | NSR3Q1b11 | EU629817 |
| 35 | S000608601 | 98.901 | uncult. bac. | Ri222 | AM110029 |
| 35 | S000678674 | 98.291 | uncult. beta proteobacterium | MTAG33 | AJ964947 |
| 36 | S000915376 | 99.534 | uncult. beta proteobacterium | MS158A1_C01 | EF705161 |
| 36 | S000608601 | 98.901 | uncult. bac. | Ri222 | AM110029 |
| 36 | S001331720 | 92.042 | *Acidovorax* sp. Z022 | FN293049 | |
| 36 | S001034645 | 91.799 | uncult. *Acidovorax* sp. | 1P-2-I01 | EU705064 |
| 36 | S001034587 | 91.799 | uncult. *Acidovorax* sp. | 1P-2-E06 | EU705006 |
| 36 | S001517497 | 91.59 | uncult. bac. | nbw346a08c1 | GQ091433 |
| 36 | S001513669 | 91.459 | uncult. bac. | nbw304e10c1 | GQ087605 |
| 36 | S001527916 | 91.459 | uncult. bac. | nbw500a10c1 | GQ101852 |
| 36 | S000607908 | 91.459 | *Acidovorax* sp. R-24667 | AM084010 | |
| 36 | S000484095 | 91.459 | *Acidovorax* sp. MG61 | AJ746118 | |
| 37 | S000915376 | 99.767 | uncult. beta proteobacterium | MS158A1_C01 | EF705161 |
| 37 | S000386190 | 99.569 | *Acidovorax* sp. 12M7 | AB120338 | |
| 37 | S000894766 | 99.37 | uncult. *Acidovorax* sp. | 40_4 | AM779871 |
| 37 | S000456780 | 99.176 | *Acidovorax* sp. ' | 14.5 MW-16& #039 | AY826564 |
| 37 | S000894761 | 99.111 | uncult. *Acidovorax* sp. | 14_2 | AM779866 |
| 37 | S000907725 | 99.079 | uncult. beta proteobacterium | MS074A1_A03 | EF697510 |
| 37 | S001082320 | 98.99 | uncult. *Acidovorax* sp. | NSR3Q1b11 | EU629817 |
| 37 | S000608601 | 98.901 | uncult. bac. | Ri222 | AM110029 |
| 37 | S000915409 | 98.496 | uncult. beta proteobacterium | MS158A1_F06 | EF705194 |
| 37 | S001331720 | 95.326 | *Acidovorax* sp. Z022 | FN293049 | |
| 38 | S000705798 | 94.387 | uncult. bac. | aab65b03 | DQ814187 |
| 38 | S000705528 | 94.387 | uncult. bac. | aab57d03 | DQ813917 |
| 38 | S000705518 | 94.387 | uncult. bac. | aab57c04 | DQ813907 |
| 38 | S000705477 | 94.387 | uncult. bac. | aaa26g10 | DQ813866 |
| 38 | S000705469 | 94.387 | uncult. bac. | aaa25h11 | DQ813858 |
| 38 | S000438730 | 94.387 | *Aeromonas* sp. ' | CDC 787-80' | U88662 |
| 38 | S000428865 | 94.387 | *Aeromonas jandaei* | B10 | AF099026 |
| 38 | S000428864 | 94.387 | *Aeromonas jandaei* | M34 | AF099025 |
| 38 | S000008085 | 94.387 | *Aeromonas jandaei* (T) | ATCC 49568T | X74678 |
| 38 | S000005395 | 94.387 | *Aeromonas* sp. RC278 | R0278(MM85) | AF063003 |
| 39 | S000386208 | 99.784 | *Microbacterium* sp. K10 | AB120356 | |
| 39 | S001568795 | 99.722 | uncult. bac. | P1_13 | GQ293382 |
| 39 | S001421174 | 99.639 | uncult. bac. | N2_12E14f | AB484430 |
| 39 | S001420942 | 99.639 | uncult. bac. | N2_E2L18f | AB484198 |
| 39 | S001420929 | 99.639 | uncult. bac. | N2_E2J16f | AB484185 |
| 39 | S001420717 | 99.639 | uncult. bac. | N2_EN17f | AB483973 |
| 39 | S001420716 | 99.639 | uncult. bac. | N2_EI10f | AB483972 |
| 39 | S001420309 | 99.639 | uncult. bac. | C2_S4L20f | AB483565 |
| 39 | S001419652 | 99.639 | uncult. bac. | C2_13H15f | AB482908 |
| 39 | S001419651 | 99.639 | uncult. bac. | C2_13G16f | AB482907 |
| 40 | S000967819 | 99.672 | *Aeromonas* sp. DH14 | EU260204 | |
| 40 | S000035980 | 99.501 | *Aeromonas* sp. Lgg5.7 | AJ489337 | |
| 40 | S000967841 | 99.222 | *Aeromonas* sp. DH46 | EU260226 | |
| 40 | S000967846 | 99.104 | *Aeromonas* sp. DH57 | EU260231 | |
| 40 | S000456820 | 99.048 | *Aeromonas* sp. ' | 10.5 MW-3' | AY826604 |

TABLE 4-continued

| SEQ | RDP_ID | Identity | Match Name | Match Name | Access. # |
|---|---|---|---|---|---|
| 40 | S000428536 | 98.679 | *Aeromonas veronii* | HM231 | AF079301 |
| 40 | S000428535 | 98.679 | *Aeromonas veronii* | HM221 | AF079300 |
| 40 | S000708457 | 96.552 | uncult. bac. | aab00d02 | DQ816846 |
| 40 | S000707859 | 96.433 | uncult. bac. | aaa78f03 | DQ816248 |
| 40 | S000706822 | 96.433 | uncult. bac. | aab51f04 | DQ815211 |
| 41 | S000394358 | 100 | *Citrobacter* sp. T40 | AF451253 | |
| 41 | S001156083 | 99.804 | *Citrobacter freundii* | CLOC1 | EU880504 |
| 41 | S000708013 | 97.092 | uncult. bac. | aab17f05 | DQ816402 |
| 41 | S000707984 | 97.092 | uncult. bac. | aab17b12 | DQ816373 |
| 41 | S000707945 | 97.092 | uncult. bac. | aaa80e03 | DQ816334 |
| 41 | S000707907 | 97.092 | uncult. bac. | aaa79e07 | DQ816296 |
| 41 | S000707639 | 97.092 | uncult. bac. | aaa86b06 | DQ816028 |
| 41 | S000707619 | 97.092 | uncult. bac. | aaa85g06 | DQ816008 |
| 41 | S000625863 | 97.092 | *Citrobacter freundii* | 7 | DQ294285 |
| 41 | S000599313 | 97.092 | uncult. bac. | s4w18-9 | DQ068918 |
| 42 | S000979075 | 100 | Enterobacteriaceae bacterium R-31537 | AM403612 | |
| 42 | S000145384 | 99.762 | *Enterobacter asburiae* | ATCC 35953 | AJ417483 |
| 42 | S000619315 | 99.75 | uncult. bac. | BPH2C10006 | DQ221379 |
| 42 | S000619234 | 99.75 | uncult. bac. | BPH1C10005 | DQ221298 |
| 42 | S000877290 | 99.722 | uncult. *Enterobacter* sp. | Grias22 | EF548003 |
| 42 | S000619317 | 99.5 | uncult. bac. | BPH2C10008 | DQ221381 |
| 42 | S000619316 | 99.5 | uncult. bac. | BPH2C10007 | DQ221380 |
| 42 | S000619233 | 99.5 | uncult. bac. | BPH1C10004 | DQ221297 |
| 42 | S001044221 | 99.369 | *Pseudomonas fluorescens* | DDBNJ508 | AY874157 |
| 42 | S000459010 | 98.491 | *Enterobacter* sp. DW56 | AJ534854 | |
| 43 | S000979075 | 99.709 | Enterobacteriaceae bacterium R-31537 | AM403612 | |
| 43 | S001044221 | 99.369 | *Pseudomonas fluorescens* | DDBNJ508 | AY874157 |
| 43 | S001195043 | 99.355 | uncult. *Serratia* sp. | C33BI24 | FJ372794 |
| 43 | S000877290 | 99.135 | uncult. *Enterobacter* sp. | Grias22 | EF548003 |
| 43 | S001568795 | 98.889 | uncult. bac. | P1_13 | GQ293382 |
| 43 | S000038165 | 98.854 | *Pantoea agglomerans* | AH16 | AJ010096 |
| 43 | S000425616 | 98.361 | *Klebsiella pneumoniae* | AY736552 | |
| 43 | S000400130 | 97.548 | *Serratia* sp. R-17665 | AY178563 | |
| 43 | S000703369 | 96.13 | uncult. gamma proteobacterium | PA-C03 | DQ295393 |
| 43 | S000967710 | 95.622 | bacterium 2AT1 | EU259710 | |
| 44 | S000394358 | 100 | *Citrobacter* sp. T40 | AF451253 | |
| 44 | S001156083 | 99.804 | *Citrobacter freundii* | CLOC1 | EU880504 |
| 44 | S000916333 | 99.744 | uncult. proteobacterium | MS030A1_E07 | EF706118 |
| 44 | S001602034 | 94.731 | uncult. *Citrobacter* sp. | F4jan.7 | GQ417907 |
| 44 | S001602032 | 94.731 | uncult. *Citrobacter* sp. | F4jan.5 | GQ417905 |
| 44 | S001093072 | 94.731 | uncult. *Citrobacter* sp. | KLOND10 | EU704221 |
| 44 | S000735520 | 94.731 | *Citrobacter* sp. I101-10 | DQ192061 | |
| 44 | S000599206 | 94.731 | uncult. bac. | f5s7 | DQ068811 |
| 44 | S000599202 | 94.619 | uncult. bac. | f5s3 | DQ068807 |
| 44 | S000966748 | 94.619 | bacterium SNR2-1 | EU195910 | |
| 45 | S000967819 | 99.837 | *Aeromonas* sp. DH14 | EU260204 | |
| 45 | S000967841 | 99.379 | *Aeromonas* sp. DH46 | EU260226 | |
| 45 | S000705477 | 93.08 | uncult. bac. | aaa26g10 | DQ813866 |
| 45 | S000705518 | 92.969 | uncult. bac. | aab57c04 | DQ813907 |
| 45 | S000705469 | 92.969 | uncult. bac. | aaa25h11 | DQ813858 |
| 45 | S000438730 | 92.969 | *Aeromonas* sp. ' | CDC 787-80' | U88662 |
| 45 | S000428865 | 92.969 | *Aeromonas jandaei* | B10 | AF099026 |
| 45 | S000428864 | 92.969 | *Aeromonas jandaei* | M34 | AF099025 |
| 45 | S000008085 | 92.969 | *Aeromonas jandaei* (T) | ATCC 49568T | X74678 |
| 45 | S000005395 | 92.969 | *Aeromonas* sp. RC278 | R0278(MM85) | AF063003 |
| 46 | S000979075 | 100 | Enterobacteriaceae bacterium R-31537 | AM403612 | |
| 46 | S000145384 | 99.762 | *Enterobacter asburiae* | ATCC 35953 | AJ417483 |
| 46 | S000619315 | 99.75 | uncult. bac. | BPH2C10006 | DQ221379 |
| 46 | S000619234 | 99.75 | uncult. bac. | BPH1C10005 | DQ221298 |
| 46 | S000877290 | 99.722 | uncult. *Enterobacter* sp. | Grias22 | EF548003 |
| 46 | S000619317 | 99.5 | uncult. bac. | BPH2C10008 | DQ221381 |
| 46 | S000619316 | 99.5 | uncult. bac. | BPH2C10007 | DQ221380 |
| 46 | S000619233 | 99.5 | uncult. bac. | BPH1C10004 | DQ221297 |
| 46 | S001419008 | 99.284 | uncult. bac. | C2_EG04f | AB482264 |
| 46 | S000459010 | 98.491 | *Enterobacter* sp. DW56 | AJ534854 | |
| 47 | S000979075 | 100 | Enterobacteriaceae bacterium R-31537 | AM403612 | |
| 47 | S001421178 | 99.642 | uncult. bac. | N2_12O07f | AB484434 |
| 47 | S001420929 | 99.642 | uncult. bac. | N2_E2J16f | AB484185 |
| 47 | S001420717 | 99.642 | uncult. bac. | N2_EN17f | AB483973 |
| 47 | S001420716 | 99.642 | uncult. bac. | N2_EI10f | AB483972 |
| 47 | S001420309 | 99.642 | uncult. bac. | C2_S4L20f | AB483565 |
| 47 | S001419652 | 99.642 | uncult. bac. | C2_13H15f | AB482908 |
| 47 | S001419651 | 99.642 | uncult. bac. | C2_13G16f | AB482907 |

TABLE 4-continued

| SEQ | RDP_ID | Identity | Match Name | Match Name | Access. # |
|---|---|---|---|---|---|
| 47 | S000459010 | 98.491 | *Enterobacter* sp. DW56 | AJ534854 | |
| 47 | S001188791 | 97.157 | endophytic bacterium HB02 | FJ205659 | |
| 48 | S000979075 | 100 | Enterobacteriaceae bacterium R-31537 | AM403612 | |
| 48 | S000386208 | 99.569 | *Microbacterium* sp. K10 | AB120356 | |
| 48 | S001421178 | 99.284 | uncult. bac. | N2__12O07f | AB484434 |
| 48 | S001420716 | 99.284 | uncult. bac. | N2__EI10f | AB483972 |
| 48 | S001420309 | 99.284 | uncult. bac. | C2__S4L20f | AB483565 |
| 48 | S001419652 | 99.284 | uncult. bac. | C2__13H15f | AB482908 |
| 48 | S001419651 | 99.284 | uncult. bac. | C2__13G16f | AB482907 |
| 48 | S001329319 | 99.074 | *Enterobacter* sp. Mn2 | FJ668636 | |
| 48 | S000877290 | 98.889 | uncult. *Enterobacter* sp. | Grias22 | EF548003 |
| 48 | S000459010 | 98.491 | *Enterobacter* sp. DW56 | AJ534854 | |
| 49 | S000386208 | 99.784 | *Microbacterium* sp. K10 | AB120356 | |
| 49 | S001568795 | 99.722 | uncult. bac. | P1__13 | GQ293382 |
| 49 | S000979075 | 99.709 | Enterobacteriaceae bacterium R-31537 | AM403612 | |
| 49 | S000619321 | 99.5 | uncult. bac. | BPH2C10012 | DQ221385 |
| 49 | S000619320 | 99.5 | uncult. bac. | BPH2C10011 | DQ221384 |
| 49 | S001329319 | 99.074 | *Enterobacter* sp. Mn2 | FJ668636 | |
| 49 | S000367749 | 99 | uncult. bac. | AP1-28 | AY119425 |
| 49 | S000459010 | 98.679 | *Enterobacter* sp. DW56 | AJ534854 | |
| 49 | S001188788 | 96.694 | endophytic bacterium HA04 | FJ205656 | |
| 49 | S000140489 | 96.694 | bacterium G2 | AY345398 | |
| 50 | S000619317 | 99.75 | uncult. bac. | BPH2C10008 | DQ221381 |
| 50 | S000916333 | 99.746 | uncult. proteobacterium | MS030A1__E07 | EF706118 |
| 50 | S000443769 | 99.667 | uncult. Enterobacteriaceae bacterium | DGGE band 10AF | AY761018 |
| 50 | S000771259 | 99.615 | uncult. bac. | ADPs2__10A | DQ342589 |
| 50 | S000619315 | 99.5 | uncult. bac. | BPH2C10006 | DQ221379 |
| 50 | S000619234 | 99.5 | uncult. bac. | BPH1C10005 | DQ221298 |
| 50 | S000771374 | 99.401 | uncult. bac. | PSAD1__10A | DQ342704 |
| 50 | S000619316 | 99.25 | uncult. bac. | BPH2C10007 | DQ221380 |
| 50 | S000619233 | 99.25 | uncult. bac. | BPH1C10004 | DQ221297 |
| 50 | S001242141 | 99.2 | *Enterobacter* sp. ZXM215 | FJ436752 | |
| 51 | S000386208 | 99.784 | *Microbacterium* sp. K10 | AB120356 | |
| 51 | S000619321 | 99.5 | uncult. bac. | BPH2C10012 | DQ221385 |
| 51 | S000619320 | 99.5 | uncult. bac. | BPH2C10011 | DQ221384 |
| 51 | S001568795 | 99.438 | uncult. bac. | P1__13 | GQ293382 |
| 51 | S000979075 | 99.412 | Enterobacteriaceae bacterium R-31537 | AM403612 | |
| 51 | S000147111 | 99.292 | *Enterobacter cloacae* subsp. *cloacae* | No 19 | AJ417467 |
| 51 | S001329319 | 99.074 | *Enterobacter* sp. Mn2 | FJ668636 | |
| 51 | S000893850 | 98.985 | *Pantoea agglomerans* | V1S7 | EU040249 |
| 51 | S000367749 | 98.802 | uncult. bac. | AP1-28 | AY119425 |
| 51 | S001095631 | 97.222 | *Enterobacter* sp. 196 | EU244779 | |
| 52 | S000967841 | 99.689 | *Aeromonas* sp. DH46 | EU260226 | |
| 52 | S000967819 | 99.675 | *Aeromonas* sp. DH14 | EU260204 | |
| 52 | S000967846 | 99.553 | *Aeromonas* sp. DH57 | EU260231 | |
| 52 | S000967847 | 99.424 | *Aeromonas* sp. DH58 | EU260232 | |
| 52 | S000967843 | 99.415 | *Aeromonas* sp. DH54 | EU260228 | |
| 52 | S000967852 | 99.303 | *Aeromonas* sp. DH69 | EU260237 | |
| 52 | S000967828 | 99.266 | *Aeromonas* sp. DH25 | EU260213 | |
| 52 | S000111085 | 97.047 | *Aeromonas* sp. MBRG 4.2 | AJ508692 | |
| 52 | S000705526 | 96.437 | uncult. bac. | aab57d01 | DQ813915 |
| 52 | S001558743 | 93.249 | uncult. bac. | p2h3 | FJ897440 |
| 53 | S000360228 | 99.526 | uncult. bac. | mdb68d09 | AY537938 |
| 53 | S000458103 | 99.502 | *Aeromonas veronii* | N63 | AB182225 |
| 53 | S000458050 | 99.502 | *Aeromonas veronii* | N09 | AB182172 |
| 53 | S000458040 | 99.5 | *Aeromonas veronii* | 105F | AB182099 |
| 53 | S000458039 | 99.5 | *Aeromonas veronii* | 104F | AB182098 |
| 53 | S000458034 | 99.5 | *Aeromonas veronii* | 99F | AB182093 |
| 53 | S000495374 | 99.4 | *Aeromonas veronii* | KIN103 | AY136084 |
| 53 | S000967841 | 99.222 | *Aeromonas* sp. DH46 | EU260226 | |
| 53 | S000967819 | 99.186 | *Aeromonas* sp. DH14 | EU260204 | |
| 53 | S001558743 | 93.446 | uncult. bac. | p2h3 | FJ897440 |
| 54 | S001421178 | 99.463 | uncult. bac. | N2__12O07f | AB484434 |
| 54 | S001421174 | 99.463 | uncult. bac. | N2__12E14f | AB484430 |
| 54 | S001420942 | 99.463 | uncult. bac. | N2__E2L18f | AB484198 |
| 54 | S001420929 | 99.463 | uncult. bac. | N2__E2J16f | AB484185 |
| 54 | S001420717 | 99.463 | uncult. bac. | N2__EN17f | AB483973 |
| 54 | S001420716 | 99.463 | uncult. bac. | N2__EI10f | AB483972 |
| 54 | S001420309 | 99.463 | uncult. bac. | C2__S4L20f | AB483565 |
| 54 | S001419652 | 99.463 | uncult. bac. | C2__13H15f | AB482908 |
| 54 | S001419651 | 99.463 | uncult. bac. | C2__13G16f | AB482907 |

TABLE 4-continued

| SEQ | RDP__ID | Identity | Match Name | Match Name | Access. # |
|---|---|---|---|---|---|
| 54 | S000459022 | 99.439 | *Pantoea* sp. DW39 | AJ534866 | |
| 55 | S001421175 | 99.463 | uncult. bac. | N2__12G22f | AB484431 |
| 55 | S001421174 | 99.463 | uncult. bac. | N2__12E14f | AB484430 |
| 55 | S001420942 | 99.463 | uncult. bac.. | N2__E2L18f | AB484198 |
| 55 | S001420929 | 99.463 | uncult. bac. | N2__E2J16f | AB484185 |
| 55 | S001420717 | 99.463 | uncult. bac. | N2__EN17f | AB483973 |
| 55 | S001420716 | 99.463 | uncult. bac. | N2__EI10f | AB483972 |
| 55 | S001420309 | 99.463 | uncult. bac. | C2__S4L20f | AB483565 |
| 55 | S001419652 | 99.463 | uncult. bac. | C2__13H15f | AB482908 |
| 55 | S001419651 | 99.463 | uncult. bac. | C2__13G16f | AB482907 |
| 55 | S000459010 | 98.679 | *Enterobacter* sp. DW56 | AJ534854 | |
| 56 | S000979075 | 100 | Enterobacteriaceae bacterium R-31537 | AM403612 | |
| 56 | S000145384 | 99.762 | *Enterobacter asburiae* | ATCC 35953 | AJ417483 |
| 56 | S000619315 | 99.75 | uncult. bac. | BPH2C10006 | DQ221379 |
| 56 | S000619234 | 99.75 | uncult. bac. | BPH1C10005 | DQ221298 |
| 56 | S000877290 | 99.722 | uncult. *Enterobacter* sp. | Grias22 | EF548003 |
| 56 | S000619317 | 99.5 | uncult. bac. | BPH2C10008 | DQ221381 |
| 56 | S000619316 | 99.5 | uncult. bac. | BPH2C10007 | DQ221380 |
| 56 | S000619233 | 99.5 | uncult. bac. | BPH1C10004 | DQ221297 |
| 56 | S001044221 | 99.369 | *Pseudomonas fluorescens* | DDBNJ508 | AY874157 |
| 56 | S000459010 | 98.302 | *Enterobacter* sp. DW56 | AJ534854 | |
| 57 | S000691722 | 99.471 | bacterium SL2.12 | DQ517031 | |
| 57 | S000030133 | 99.468 | *Aeromonas veronii* | S4M13 | AF472504 |
| 57 | S000458071 | 99.46 | *Aeromonas veronii* | N31 | AB182193 |
| 57 | S000428536 | 99.434 | *Aeromonas veronii* | HM231 | AF079301 |
| 57 | S000428535 | 99.434 | *Aeromonas veronii* | HM221 | AF079300 |
| 57 | S000497364 | 99.429 | bacterium c07-4b | AB198050 | |
| 57 | S000457969 | 99.341 | *Aeromonas veronii* | 34F | AB182028 |
| 57 | S000039286 | 99.333 | *Aeromonas* sp. | BB8 | Z48271 |
| 57 | S000039271 | 99.333 | *Aeromonas* sp. | BB6 | Z48266 |
| 57 | S000892761 | 99.203 | *Aeromonas veronii* | 9T1LB41 | EF634231 |
| 58 | S001421176 | 99.821 | uncult. bac. | N2__12H21f | AB484432 |
| 58 | S001421175 | 99.821 | uncult. bac. | N2__12G22f | AB484431 |
| 58 | S001421174 | 99.821 | uncult. bac. | N2__12E14f | AB484430 |
| 58 | S001420942 | 99.821 | uncult. bac. | N2__E2L18f | AB484198 |
| 58 | S001420929 | 99.821 | uncult. bac. | N2__E2J16f | AB484185 |
| 58 | S001420717 | 99.821 | uncult. bac. | N2__EN17f | AB483973 |
| 58 | S001420716 | 99.821 | uncult. bac. | N2__EI10f | AB483972 |
| 58 | S001420309 | 99.821 | uncult. bac. | C2__S4L20f | AB483565 |
| 58 | S001419652 | 99.821 | uncult. bac. | C2__13H15f | AB482908 |
| 58 | S001419651 | 99.821 | uncult. bac. | C2__13G16f | AB482907 |
| 59 | S000979075 | 100 | Enterobacteriaceae bacterium R-31537 | AM403612 | |
| 59 | S001421368 | 99.821 | uncult. bac. | N2__13O20f | AB484624 |
| 59 | S001421367 | 99.821 | uncult. bac. | N2__13J21f | AB484623 |
| 59 | S001420939 | 99.821 | uncult. bac. | N2__E2L12f | AB484195 |
| 59 | S001420878 | 99.821 | uncult. bac. | N2__E2B02f | AB484134 |
| 59 | S001420730 | 99.821 | uncult. bac. | N2__EP08f | AB483986 |
| 59 | S001420729 | 99.821 | uncult. bac. | N2__EO06f | AB483985 |
| 59 | S001420728 | 99.821 | uncult. bac. | N2__EL16f | AB483984 |
| 59 | S001420727 | 99.821 | uncult. bac. | N2__EJ05f | AB483983 |
| 59 | S001419008 | 99.821 | uncult. bac. | C2__EG04f | AB482264 |
| 60 | S000771394 | 100 | uncult. bac. | S1-7f | DQ342724 |
| 60 | S000771149 | 100 | uncult. bac. | AD1F4D | DQ342479 |
| 60 | S000771044 | 99.837 | uncult. bac. | AD1-2F12B | DQ342374 |
| 60 | S000619317 | 99.75 | uncult. bac. | BPH2C10008 | DQ221381 |
| 60 | S000771139 | 99.676 | uncult. bac. | AD1F12H | DQ342469 |
| 60 | S001420728 | 99.642 | uncult. bac. | N2__EL16f | AB483984 |
| 60 | S001420727 | 99.642 | uncult. bac. | N2__EJ05f | AB483983 |
| 60 | S001419008 | 99.642 | uncult. bac. | C2__EG04f | AB482264 |
| 60 | S000917259 | 99.518 | uncult. proteobacterium | MS168A1__G07 | EF707044 |
| 60 | S001600253 | 98.485 | uncult. *Citrobacter* sp. | F5jun.13 | GQ416126 |
| 61 | S001420942 | 100 | uncult. bac. | N2__E2L18f | AB484198 |
| 61 | S001420929 | 100 | uncult. bac. | N2__E2J16f | AB484185 |
| 61 | S001420717 | 100 | uncult. bac. | N2__EN17f | AB483973 |
| 61 | S001420716 | 100 | uncult. bac. | N2__EI10f | AB483972 |
| 61 | S001420309 | 100 | uncult. bac. | C2__S4L20f | AB483565 |
| 61 | S001419652 | 100 | uncult. bac. | C2__13H15f | AB482908 |
| 61 | S001419651 | 100 | uncult. bac. | C2__13G16f | AB482907 |
| 61 | S000459010 | 98.679 | *Enterobacter* sp. DW56 | AJ534854 | |
| 61 | S001188788 | 96.364 | endophytic bacterium HA04 | FJ205656 | |
| 61 | S000140489 | 96.364 | bacterium G2 | AY345398 | |
| 62 | S000979075 | 100 | Enterobacteriaceae bacterium R-31537 | AM403612 | |
| 62 | S000145384 | 99.762 | *Enterobacter asburiae* | ATCC 35953 | AJ417483 |
| 62 | S000619315 | 99.75 | uncult. bac. | BPH2C10006 | DQ221379 |

TABLE 4-continued

| SEQ | RDP_ID | Identity | Match Name | Match Name | Access. # |
|---|---|---|---|---|---|
| 62 | S000619234 | 99.75 | uncult. bac. | BPH1C10005 | DQ221298 |
| 62 | S000877290 | 99.722 | uncult. *Enterobacter* sp. | Grias22 | EF548003 |
| 62 | S000619317 | 99.5 | uncult. bac. | BPH2C10008 | DQ221381 |
| 62 | S000619316 | 99.5 | uncult. bac. | BPH2C10007 | DQ221380 |
| 62 | S000619233 | 99.5 | uncult. bac. | BPH1C10004 | DQ221297 |
| 62 | S000619231 | 99.5 | uncult. bac. | BPH1C10002 | DQ221295 |
| 62 | S001044221 | 99.369 | *Pseudomonas fluorescens* | DDBNJ508 | AY874157 |
| 63 | S000979075 | 99.709 | Enterobacteriaceae bacterium R-31537 | AM403612 | |
| 63 | S001421178 | 99.642 | uncult. bac. | N2__12O07f | AB484434 |
| 63 | S001420716 | 99.642 | uncult. bac. | N2__EI10f | AB483972 |
| 63 | S001420309 | 99.642 | uncult. bac. | C2__S4L20f | AB483565 |
| 63 | S001419652 | 99.642 | uncult. bac. | C2__13H15f | AB482908 |
| 63 | S001419651 | 99.642 | uncult. bac. | C2__13G16f | AB482907 |
| 63 | S001188791 | 98.333 | endophytic bacterium HB02 | FJ205659 | |
| 63 | S000711290 | 98.205 | *Pantoea agglomerans* | WAB1872 | AM184214 |
| 63 | S000140489 | 98.205 | bacterium G2 | AY345398 | |
| 63 | S000599273 | 98.077 | uncult. bac. | bb2s2 | DQ068878 |
| 64 | S000979075 | 100 | Enterobacteriaceae bacterium R-31537 | AM403612 | |
| 64 | S001421368 | 99.821 | uncult. bac. | N2__13O20f | AB484624 |
| 64 | S001421367 | 99.821 | uncult. bac. | N2__13J21f | AB484623 |
| 64 | S001420939 | 99.821 | uncult. bac. | N2__E2L12f | AB484195 |
| 64 | S001420878 | 99.821 | uncult. bac. | N2__E2B02f | AB484134 |
| 64 | S001420730 | 99.821 | uncult. bac. | N2__EP08f | AB483986 |
| 64 | S001420729 | 99.821 | uncult. bac. | N2__EO06f | AB483985 |
| 64 | S001420728 | 99.821 | uncult. bac. | N2__EL16f | AB483984 |
| 64 | S001420727 | 99.821 | uncult. bac. | N2__EJ05f | AB483983 |
| 64 | S001419008 | 99.821 | uncult. bac. | C2__EG04f | AB482264 |
| 65 | S001421367 | 99.821 | uncult. bac. | N2__13J21f | AB484623 |
| 65 | S001420939 | 99.821 | uncult. bac. | N2__E2L12f | AB484195 |
| 65 | S001420878 | 99.821 | uncult. bac. | N2__E2B02f | AB484134 |
| 65 | S001420730 | 99.821 | uncult. bac. | N2__EP08f | AB483986 |
| 65 | S001420729 | 99.821 | uncult. bac. | N2__EO06f | AB483985 |
| 65 | S001420728 | 99.821 | uncult. bac. | N2__EL16f | AB483984 |
| 65 | S001420727 | 99.821 | uncult. bac. | N2__EJ05f | AB483983 |
| 65 | S001419008 | 99.821 | uncult. bac. | C2__EG04f | AB482264 |
| 65 | S001488489 | 91.346 | uncult. bac. | nbw32d08c1 | GQ062425 |
| 65 | S001488415 | 91.346 | uncult. bac. | nbw31e02c1 | GQ062351 |
| 66 | S001421176 | 100 | uncult. bac. | N2__12H21f | AB484432 |
| 66 | S001421175 | 100 | uncult. bac. | N2__12G22f | AB484431 |
| 66 | S001421174 | 100 | uncult. bac. | N2__12E14f | AB484430 |
| 66 | S001420942 | 100 | uncult. bac. | N2__E2L18f | AB484198 |
| 66 | S001420929 | 100 | uncult. bac. | N2__E2J16f | AB484185 |
| 66 | S001420717 | 100 | uncult. bac. | N2__EN17f | AB483973 |
| 66 | S001420716 | 100 | uncult. bac. | N2__EI10f | AB483972 |
| 66 | S001420309 | 100 | uncult. bac. | C2__S4L20f | AB483565 |
| 66 | S001419652 | 100 | uncult. bac. | C2__13H15f | AB482908 |
| 66 | S001419651 | 100 | uncult. bac. | C2__13G16f | AB482907 |
| 67 | S000979075 | 99.709 | Enterobacteriaceae bacterium R-31537 | AM403612 | |
| 67 | S001421178 | 99.642 | uncult. bac. | N2__12O07f | AB484434 |
| 67 | S001420717 | 99.642 | uncult. bac. | N2__EN17f | AB483973 |
| 67 | S001420716 | 99.642 | uncult. bac. | N2__EI10f | AB483972 |
| 67 | S001420309 | 99.642 | uncult. bac. | C2__S4L20f | AB483565 |
| 67 | S001419652 | 99.642 | uncult. bac. | C2__13H15f | AB482908 |
| 67 | S001419651 | 99.642 | uncult. bac. | C2__13G16f | AB482907 |
| 67 | S001188791 | 96.654 | endophytic bacterium HB02 | FJ205659 | |
| 67 | S000711290 | 96.525 | *Pantoea agglomerans* | WAB1872 | AM184214 |
| 67 | S000140489 | 96.525 | bacterium G2 | AY345398 | |
| 68 | S001195043 | 98.387 | uncult. *Serratia* sp. | C33BI24 | FJ372794 |
| 68 | S000038165 | 98.286 | *Pantoea agglomerans* | AH16 | AJ010096 |
| 68 | S000360061 | 98.264 | uncult. bac. | 2F06 | AY537762 |
| 68 | S000360017 | 98.258 | uncult. bac. | 1G08 | AY537716 |
| 68 | S000979075 | 98.256 | Enterobacteriaceae bacterium R-31537 | AM403612 | |
| 68 | S001044221 | 98.113 | *Pseudomonas fluorescens* | DDBNJ508 | AY874157 |
| 68 | S000425616 | 98.033 | *Klebsiella pneumoniae* | AY736552 | |
| 68 | S001082253 | 97.351 | uncult. *Klebsiella* sp. | NSR3Q1b71 | EU629750 |
| 68 | S000359995 | 97.213 | uncult. bac. | 1D06 | AY537693 |
| 68 | S000360189 | 96.117 | uncult. bac. | 2B12 | AY537895 |
| 69 | S000979075 | 99.709 | Enterobacteriaceae bacterium R-31537 | AM403612 | |
| 69 | S000386208 | 99.353 | *Microbacterium* sp. K10 | AB120356 | |
| 69 | S001568795 | 99.167 | uncult. bac. | P1__13 | GQ293382 |
| 69 | S001044221 | 99.054 | *Pseudomonas fluorescens* | DDBNJ508 | AY874157 |

TABLE 4-continued

| SEQ | RDP_ID | Identity | Match Name | Match Name | Access. # |
|---|---|---|---|---|---|
| 69 | S001329319 | 98.843 | *Enterobacter* sp. Mn2 | FJ668636 | |
| 69 | S000877290 | 98.611 | uncult. *Enterobacter* sp. | Grias22 | EF548003 |
| 69 | S000459010 | 98.302 | *Enterobacter* sp. DW56 | AJ534854 | |
| 69 | S001188791 | 93.722 | endophytic bacterium HB02 | FJ205659 | |
| 69 | S000140489 | 93.612 | bacterium G2 | AY345398 | |
| 69 | S000599273 | 93.502 | uncult. bac. | bb2s2 | DQ068878 |
| 70 | S001421176 | 100 | uncult. bac. | N2__12H21f | AB484432 |
| 70 | S001421175 | 100 | uncult. bac. | N2__12G22f | AB484431 |
| 70 | S001421174 | 100 | uncult. bac. | N2__12E14f | AB484430 |
| 70 | S001420942 | 100 | uncult. bac. | N2__E2L18f | AB484198 |
| 70 | S001420929 | 100 | uncult. bac. | N2__E2J16f | AB484185 |
| 70 | S001420717 | 100 | uncult. bac. | N2__EN17f | AB483973 |
| 70 | S001420716 | 100 | uncult. bac. | N2__EI10f | AB483972 |
| 70 | S001420309 | 100 | uncult. bac. | C2__S4L20f | AB483565 |
| 70 | S001419652 | 100 | uncult. bac. | C2__13H15f | AB482908 |
| 70 | S001419651 | 100 | uncult. bac. | C2__13G16f | AB482907 |
| 71 | S000145384 | 100 | *Enterobacter asburiae* | ATCC 35953 | AJ417483 |
| 71 | S000619315 | 100 | uncult. bac. | BPH2C10006 | DQ221379 |
| 71 | S000619234 | 100 | uncult. bac. | BPH1C10005 | DQ221298 |
| 71 | S000619317 | 99.75 | uncult. bac. | BPH2C10008 | DQ221381 |
| 71 | S001420730 | 99.643 | uncult. bac. | N2__EP08f | AB483986 |
| 71 | S001420729 | 99.643 | uncult. bac. | N2__EO06f | AB483985 |
| 71 | S001420728 | 99.643 | uncult. bac. | N2__EL16f | AB483984 |
| 71 | S001420727 | 99.643 | uncult. bac. | N2__EJ05f | AB483983 |
| 71 | S001419008 | 99.643 | uncult. bac. | C2__EG04f | AB482264 |
| 71 | S000459010 | 98.679 | *Enterobacter* sp. DW56 | AJ534854 | |
| 72 | S000035980 | 99.751 | *Aeromonas* sp. Lgg5.7 | AJ489337 | |
| 72 | S000456820 | 99.365 | *Aeromonas* sp. ' | 10.5 MW-3' | AY826604 |
| 72 | S000967841 | 99.07 | *Aeromonas* sp. DH46 | EU260226 | |
| 72 | S000967819 | 99.026 | *Aeromonas* sp. DH14 | EU260204 | |
| 72 | S000691722 | 98.942 | bacterium SL2.12 | DQ517031 | |
| 72 | S000030133 | 98.936 | *Aeromonas veronii* | S4M13 | AF472504 |
| 72 | S000458071 | 98.921 | *Aeromonas veronii* | N31 | AB182193 |
| 72 | S000428536 | 98.868 | *Aeromonas veronii* | HM231 | AF079301 |
| 72 | S000428535 | 98.868 | *Aeromonas veronii* | HM221 | AF079300 |
| 72 | S000967846 | 97.774 | *Aeromonas* sp. DH57 | EU260231 | |
| 73 | S000386208 | 99.784 | *Microbacter*. sp. K10 | AB120356 | |
| 73 | S001568795 | 99.722 | uncult. bac. | P1__13 | GQ293382 |
| 73 | S000979075 | 99.709 | Enterobacteriaceae bacterium R-31537 | AM403612 | |
| 73 | S001420929 | 98.566 | uncult. bac. | N2__E2J16f | AB484185 |
| 73 | S001420717 | 98.566 | uncult. bac. | N2__EN17f | AB483973 |
| 73 | S001420716 | 98.566 | uncult. bac. | N2__EI10f | AB483972 |
| 73 | S001420309 | 98.566 | uncult. bac. | C2__S4L20f | AB483565 |
| 73 | S001419652 | 98.566 | uncult. bac. | C2__13H15f | AB482908 |
| 73 | S001419651 | 98.566 | uncult. bac. | C2__13G16f | AB482907 |
| 73 | S000459010 | 98.308 | *Enterobacter* sp. DW56 | AJ534854 | |
| 74 | S000804928 | 98.773 | *Salmonella enterica* subsp. *enterica* serovar *Typhimurium* | LT2 | D12814 |
| 74 | S000804927 | 98.773 | *Salmonella enterica* subsp. *enterica* serovar *Typhi* | D12813 | |
| 74 | S000804926 | 98.773 | *Salmonella enterica* subsp. *enterica* | D12812 | |
| 74 | S000804925 | 98.773 | *Salmonella enterica* subsp. *enterica* serovar *Enteritidis* | D12811 | |
| 74 | S000804924 | 98.773 | *Salmonella enterica* subsp. *enterica* serovar Dublin | D12810 | |
| 74 | S000804923 | 98.773 | *Salmonella enterica* | D12809 | |
| 74 | S000832411 | 97.971 | uncult. bac. | VT70 | EF063971 |
| 74 | S000832410 | 97.971 | uncult. bac. | VT65 | EF063970 |
| 74 | S000832409 | 97.971 | uncult. bac. | VT40 | EF063969 |
| 74 | S000967880 | 96.161 | *Enterobacter* sp. DH40-2 | EU260265 | |
| 75 | S000979075 | 100 | Enterobacteriaceae bacterium R-31537 | AM403612 | |
| 75 | S000145384 | 99.762 | *Enterobacter asburiae* | ATCC 35953 | AJ417483 |
| 75 | S000619315 | 99.75 | uncult. bac. | BPH2C10006 | DQ221379 |
| 75 | S000619234 | 99.75 | uncult. bac. | BPH1C10005 | DQ221298 |
| 75 | S000877290 | 99.722 | uncult. *Enterobacter* sp. | Grias22 | EF548003 |
| 75 | S000619317 | 99.5 | uncult. bac. | BPH2C10008 | DQ221381 |
| 75 | S000619316 | 99.5 | uncult. bac. | BPH2C10007 | DQ221380 |
| 75 | S000619233 | 99.5 | uncult. bac. | BPH1C10004 | DQ221297 |
| 75 | S000619231 | 99.5 | uncult. bac. | BPH1C10002 | DQ221295 |
| 75 | S001044221 | 99.369 | *Pseudomonas fluorescens* | DDBNJ508 | AY874157 |
| 76 | S001421176 | 100 | uncult. bac. | N2__12H21f | AB484432 |
| 76 | S001421175 | 100 | uncult. bac. | N2__12G22f | AB484431 |
| 76 | S001421174 | 100 | uncult. bac. | N2__12E14f | AB484430 |

TABLE 4-continued

| SEQ | RDP_ID | Identity | Match Name | Match Name | Access. # |
|---|---|---|---|---|---|
| 76 | S001420942 | 100 | uncult. bac. | N2_E2L18f | AB484198 |
| 76 | S001420929 | 100 | uncult. bac. | N2_E2J16f | AB484185 |
| 76 | S001420717 | 100 | uncult. bac. | N2_EN17f | AB483973 |
| 76 | S001420716 | 100 | uncult. bac. | N2_EI10f | AB483972 |
| 76 | S001420309 | 100 | uncult. bac. | C2_S4L20f | AB483565 |
| 76 | S001419652 | 100 | uncult. bac. | C2_13H15f | AB482908 |
| 76 | S001419651 | 100 | uncult. bac. | C2_13G16f | AB482907 |
| 77 | S000619324 | 99.75 | uncult. bac. | BPH2C12003 | DQ221388 |
| 77 | S001419009 | 99.463 | uncult. bac. | C2_EI14f | AB482265 |
| 77 | S000911957 | 99.275 | uncult. proteobacterium | MS043A1_F01 | EF701742 |
| 77 | S000619239 | 99.25 | uncult. bac. | BPH1C12001 | DQ221303 |
| 77 | S001419303 | 99.106 | uncult. bac. | C2_E2M04f | AB482559 |
| 77 | S001419265 | 99.106 | uncult. bac. | C2_E2I11f | AB482521 |
| 77 | S001231817 | 99.026 | uncult. bac. | gb3_HZ1B12 | FJ454745 |
| 77 | S000619326 | 98.5 | uncult. bac. | BPH2C12005 | DQ221390 |
| 77 | S000619325 | 98.5 | uncult. bac. | BPH2C12004 | DQ221389 |
| 77 | S000619323 | 98.5 | uncult. bac. | BPH2C12002 | DQ221387 |
| 78 | S001419009 | 99.284 | uncult. bac. | C2_EI14f | AB482265 |
| 78 | S000619324 | 99.25 | uncult. bac. | BPH2C12003 | DQ221388 |
| 78 | S001419303 | 98.927 | uncult. bac. | C2_E2M04f | AB482559 |
| 78 | S001419265 | 98.927 | uncult. bac. | C2_E2I11f | AB482521 |
| 78 | S000619239 | 98.75 | uncult. bac. | BPH1C12001 | DQ221303 |
| 78 | S000400130 | 98.634 | *Serratia* sp. R-17665 | AY178563 | |
| 78 | S000619326 | 98.5 | uncult. bac. | BPH2C12005 | DQ221390 |
| 78 | S000619325 | 98.5 | uncult. bac. | BPH2C12004 | DQ221389 |
| 78 | S000619323 | 98.5 | uncult. bac. | BPH2C12002 | DQ221387 |
| 78 | S000979075 | 97.965 | Enterobacteriaceae bacterium R-31537 | AM403612 | |
| 79 | S001419009 | 99.821 | uncult. bac. | C2_EI14f | AB482265 |
| 79 | S000619324 | 99.75 | uncult. bac. | BPH2C12003 | DQ221388 |
| 79 | S001419303 | 99.463 | uncult. bac. | C2_E2M04f | AB482559 |
| 79 | S001419265 | 99.463 | uncult. bac. | C2_E2I11f | AB482521 |
| 79 | S000911957 | 99.275 | uncult. proteobacterium | MS043A1_F01 | EF701742 |
| 79 | S000619239 | 99.25 | uncult. bac. | BPH1C12001 | DQ221303 |
| 79 | S000751165 | 98.785 | bacterium E8 | EF016528 | |
| 79 | S000619326 | 98.5 | uncult. bac. | BPH2C12005 | DQ221390 |
| 79 | S000619325 | 98.5 | uncult. bac. | BPH2C12004 | DQ221389 |
| 79 | S000619323 | 98.5 | uncult. bac. | BPH2C12002 | DQ221387 |
| 80 | S001419009 | 99.642 | uncult. bac. | C2_EI14f | AB482265 |
| 80 | S001419303 | 99.284 | uncult. bac. | C2_E2M04f | AB482559 |
| 80 | S001419265 | 99.284 | uncult. bac. | C2_E2I11f | AB482521 |
| 80 | S000836340 | 99.087 | uncult. bac. | 042_48h_JTSP | EF494584 |
| 80 | S000911957 | 99.034 | uncult. proteobacterium | MS043A1_F01 | EF701742 |
| 80 | S000619324 | 99 | uncult. bac. | BPH2C12003 | DQ221388 |
| 80 | S001046945 | 98.933 | *Buttiauxella* sp. 01WB03.2-68 | FM161460 | |
| 80 | S000979075 | 98.529 | Enterobacteriaceae bacterium R-31537 | AM403612 | |
| 80 | S001195043 | 98.058 | uncult. *Serratia* sp. | C33BI24 | FJ372794 |
| 80 | S000877290 | 98.056 | uncult. *Enterobacter* sp. | Grias22 | EF548003 |
| 81 | S001419009 | 99.821 | uncult. bac. | C2_EI14f | AB482265 |
| 81 | S001419303 | 99.463 | uncult. bac. | C2_E2M04f | AB482559 |
| 81 | S001419265 | 99.463 | uncult. bac. | C2_E2I11f | AB482521 |
| 81 | S000619324 | 99.25 | uncult. bac. | BPH2C12003 | DQ221388 |
| 81 | S000836340 | 99.097 | uncult. bac. | 042_48h_JTSP | EF494584 |
| 81 | S001046945 | 98.95 | *Buttiauxella* sp. 01WB03.2-68 | FM161460 | |
| 81 | S000751165 | 98.58 | bacterium E8 | EF016528 | |
| 81 | S001156171 | 98.462 | *Buttiauxella agrestis* | KesE3 | EU884312 |
| 81 | S001323632 | 97.489 | uncult. *Citrobacter* sp. | TTGF gel band C2 | FJ719116 |
| 81 | S000969150 | 94.881 | uncult. bac. | f13 | AB291632 |

TABLE 5 summarizes the bacterial Family and Genus dominance that may be concluded in view of the TABLE 4 results. "Br" is bluegill; "FHM" is fathead minnow; "Gam" is mosquitofish, or *Gambusia*; and "GS" is golden shiner.

TABLE 5

| Source Fish | SEQ ID NOs. from sequenced bacteria | Family | Genus |
|---|---|---|---|
| "Br" | 1-23 | Aeromonadaceae/ Moraxcellaceae | *Aeromonas*/ *Acinetobacter* |
| "FHM" | 24-37 | Comamonadaceae | *Acidovorax* |
| "Gam" | 38-76 | Aeromonadaceae/ Enterobacteriaceae | *Aeromonas*/ *Enterobacter* |
| "GS" | 77-81 | Enterobacteriaceae | *Enterobacter* |

Behavior-eliciting compositions according to the present invention may include bacteria of the dominant families and genera indicated in TABLE 5. For example, if a predator fish preferentially exhibits feeding behavior in the presence of Bluegills, adding bacteria of the family Aeromonadaceae and the genus *Aeromonas* to compositions in accordance with the present invention may be effective in eliciting feeding behavior in said predator fish. Now that the inventors have disclosed the association between the source fish (Br, FHM, Gam, and GS) and the dominant bacterial families and genera, skilled artisans will instantly appreciate that it may be advantageous to add specific bacteria to compositions in order to influence the behavior of fish, avians, or marine mammals.

In another embodiment, compositions according to the present invention may include non-dominant bacteria. The methods disclosed by the instant application enable one of skill to isolate and test novel bacteria for their ability to elicit feeding responses in fish, avians, and marine mammals. The fish, avians, and marines animals may be responding to the dominant bacteria, or they may be responding to less well-represented bacteria. In either case, routine experimentation, as fully disclosed and described by the instant application, can be used to establish a correlation between specific bacteria (isolated from a source fish) and a feeding response exhibited by said fish, avians, or marine mammals.

It will be clear to those skilled in the art of fish modifying compositions that many modifications and substitutions can be made to the composition and its various methods of preparation and use described above without departing from the spirit and scope of the invention, which is defined by the appended claims.

CITED REFERENCES

Baker G C, Smith J J, Cowan D A. Review and re-analysis of domain-specific 16S primers. J Microbiol Methods. 2003 December; 55(3):541-55.

Bano, N., W. A. Bennett, A. deR. Smith, L. Vasquez and J. T. Hollibaugh. 2007. Dominance of Mycoplasma in the guts of the Long-Jawed Mudsucker, *Gillichthys mirabilis*, from five California salt marshes. Environmental Microbiology 9: 2636-2631.

Bardach, J. E. and T. Villars (1974). The chemical senses of fishes. *Chemoreception in Marine Organisms*. P. T. Grant and A. M. Mackie. New York, Academic Press. 1: 49-104.

Bergey, D. H. (1994). *Bergey's Manual of Determinative Bacteriology*. Baltimore, Lippincott Williams & Wilkins.

Carr, W. E. S. (1988). The molecular nature of chemical stimuli in the aquatic environment. *Sensory Biology of Aquatic Animals*. J. Atema. New York, Springer-Verlag: 3-27.

COLE et al. Nucleic Acids Res. 2009 January; 37 (Database issue):D141-5. Epub 2008 Nov. 12.

CUMMINS, S. E., SCHEIN, C. H., XU, Y., BRAUN, W., and NAGLE, G. T. 2005. Molluscan attractins: A family of water-borne protein pheromones with interspecific attractiveness. Peptides 26: 121-129.

Davis, B. D., R. Dulbecco, et al. (1990). *Microbiology*. Philadelphia, Lippencott Williams & Wilkins.

Eaton, A. D., L. S. Clesceri, et al. (1992). Method 4500-Cl. *Standard Methods for the Examination of Water & Wastewater*, American Public Health Association.

Fisknes, B. and K. Doving (1982). "Olfactory sensitivity to group-specific substances in Atlantic salmon." *Journal of Chemical Ecology* 8(8): 1083-1091.

Hara, T. J. (1992). *Fish Chemoreception*. London, Chapman & Hall.

HARDEGE, J., BARTELS-HARDEGE, H., MULLER, C. T., and BECKMANN, M. 2004. Peptide pheromones in female Nereis succinea. Peptides 9:1517-1522.

HOWE, N. R., and SHEIKH, Y. M. 1975. Anthopleurine: A sea anemone alarm pheromone. Science 189:386-388.

KICKLIGHTER, C. E., GERMANN, M., KAMIO, M., and DERBY, C. D. 2007. Molecular identification of alarm cues in the defensive secretions of the sea hare Aplysia californica. Anim. Behay. 74:1481-1492.

Kleerekoper, H. (1969). Olfaction in Fishes. Bloomington, Indiana University Press.

KRUG, P. J., and MANZI, A. E. 1999. Waterborne and surface-associated carbohydrates as settlement cues for larvae of the specialist marine herbivore, Alderia modesta. Biol. Bull. 197: 94-103.

Lim, C. and C. D. Webster (2001). *Nutrition and Fish Health*. Philadelphia, Haworth Press.

Naylor, R. L., R. J. Goldberg, et al. (2000). "Effect of aquaculture on world fish supplies." *Nature* 405(6790): 1017-1024.

PAINTER, S. D., CLOUGH, B., GARDEN, R. W., SWEEDLER, J. V., and NAGLE, G. T. 1998. Characterization of Aplysia attractin, the first waterborne peptide pheromone in invertebrates. Biol. Bull. 194:120-131.

PAWLIK, J. R., and BUTMAN, C. A. 1993. Settlement of a marine tube worm as a function of current velocity: Interacting effects of hydrodynamics and behavior. Limnol. Oceanogr. 38:1730-1740.

Pfeiffer, W. (1982). Chemical signals in communication. *Chemorecption in Fishes*. T. J. Hara. New York, Elsevier Sci. Publ. Co.: 307-326.

Reutter, K., F. Boudriot, et al. (2000). "Heterogeneity of Fish Taste Bud Ultrastructure as Demonstrated in the Holosteans Amia calva and Lepisosteus oculatus." *Philosophical Transactions: Biological Sciences* 355(1401): 1225-1228.

Sokal, R. F. and F. J. Rohlf (1969). *Biometry*. San Francisco, W. H. Freeman & Co.

Subcommittee-Fish-Nutrition (1993). *Nutrient Requirements of Fish*. Washington, D.C., The National Academies Press.

Zimmer and Zimmer. (2008) Dynamic Scaling in Chemical Ecology. J Chem Ecol 34:822-836.

What is claimed is:

1. A composition for producing a feeding response in a target/predator fish comprising:

i) at least one bacterial species from a source/feeder fish or fishes, which bacterial species is typically associated with the source/feeder fish, and wherein said bacterial species stimulates the feeding response in said target/predator fish;

ii) a pharmaceutically or veterinarily acceptable excipient, diluent or vehicle; and iii) a high protein food source which is unpalatable to the target fish when the bacterial species is not part of the composition; and wherein the target/predator fish exhibits the feeding response when it is exposed to the composition because the target/predator fish tastes or smells the bacterial species; and wherein the bacterial species is chemically inactivated; and wherein the feeding response persists such that the predator fish not only initially samples or consumes the composition, but continues to consume and subsist upon the composition; made by the steps of:

a. extracting at least one bacterial species from a source fish or fishes, wherein said feeder/prey fish are selected for stimulating rapid and sustained feeding behavior in a target/predator fish;

b. culturing said bacterial species in a minimal medium;

c. chemically inactivating the bacterial species using formaldehyde or another cross-linking agent, and rinsing away substantially all soluble molecules;

d. confirming the bacterial species elicits a substantially similar feeding response in the target/predator fish as do the feeder/prey fish; and e. combining said inactivated bacterial species with 1. the pharmaceutically or veterinarily acceptable excipient, diluent or vehicle; and
2. the high protein food source; thereby forming the composition for producing the feeding response in the target/predator fish.

2. The composition of claim 1, wherein the target/predator fish exhibits the feeding response within 10 minutes of being exposed to the composition.

3. The composition of claim 1 or 2, wherein the protein is soy or casein, and wherein the source/feeder fish is a bluegill, a fathead minnow, a mosquitofish, or a golden shiner.

4. The composition of claim 1, which contains about $2.5\times 10^{12}$ inactivated bacteria per pound.

5. The composition according to claim 1, wherein said bacterial species is a *Citrobacter* or an *Acidovorax*.

6. The composition of claim 1, wherein said bacteria were cultured in a minimal medium prior to being inactivated.

7. The composition of claim 1 wherein said bacteria were cultured in a dark environment to prevent the growth of photosynthetic organisms.

8. The composition of claim 1 wherein said bacteria were cultured in a medium that comprises a mixture of potassium phosphate-dibasic, potassium phosphate-monobasic, ammonium sulfate, sodium sulfate, magnesium sulfate, distilled water, and glucose.

9. A process for preparing the composition of claim 1 comprising the steps of:

i) extracting at least one bacterial species from a source fish or fishes, wherein said source fish are selected for stimulating feeding behavior in said target fish;

ii) culturing said bacterial species in a minimal medium; and iii) combining said cultured bacteria with a pharmaceutically or veterinarily acceptable excipient, diluent or vehicle to form said composition.

10. The process of claim 9, wherein said bacteria is Enterobacteriaceae.

11. The process of claim 9, wherein said bacteria is a *Citrobacter* or an *Acidovorax*.

12. The process of claim 9, wherein said bacteria is *Citrobacter freundii*.

13. The process of claim 9, wherein said culturing step takes place in a dark environment.

14. The process of claim 9, wherein said bacteria are cultured in a minimal medium.

15. The process of claim 9, wherein said medium comprises a mixture of potassium phosphate-dibasic, potassium phosphate-monobasic, ammonium sulfate, sodium sulfate, magnesium sulfate, and distilled water.

16. The process of claim 9, wherein said medium comprises a mixture of potassium phosphate-dibasic, potassium phosphate-monobasic, ammonium sulfate, sodium sulfate, magnesium sulfate, distilled water, and glucose.

17. The process of claim 9, wherein said medium comprises: potassium phosphate-dibasic, present in an amount between approximately 0.1% to 2.0% by weight; potassium phosphate-monobasic, present in an amount between approximately 0.1% to 1.0%, by weight; ammonium sulfate, present in an amount between approximately 0.01% to 0.8% by weight; sodium sulfate, present in an amount between approximately 0.005% to 0.55% by weight; magnesium sulfate, present in an amount between approximately 0.001% to 0.03% 0.01% by weight; distilled water, present in an amount between approximately 70% to 99% by weight; and a concentrated solution of sterile glucose between approximately 1.0% to 10.0% by weight.

18. The process of claim 9, wherein said culturing continues until there is a substantial increase of the bacterial biomass or until the end of the bacterial growth cycle.

19. The process of claim 9, wherein said culturing is performed for approximately 48 hours.

20. The process of claim 9, wherein said excipient, diluent or vehicle is water.

21. The composition of claim 1, wherein the rinsing away step comprises at least 2 rinses.

22. The composition of claim 21, wherein the predator fish would not subsist on the composition in absence of the bacterial species.

23. The composition of claim 21, which contains substantially no or no free amino acids.

24. The composition of claim 21, comprising less fish meal than would be required to elicit the persistent feeding behavior.

25. The composition of claim 21, comprising substantially no fish meal.

26. The composition of claim 25, comprising no fish meal.

27. The composition of claim 21, comprising a mixture of more than one bacterial species.

28. The composition of claim 27, at least one *Acidovorax* species, at least one *Aeromonas* species, and at least one *Citrobacter* species.

29. The composition of claim 21, wherein the bacterial species is capable of growing on minimal media containing only a carbon source and salts containing elements required for protein and nucleic acid synthesis.

30. The composition of claim 1, wherein the protein is soy or casein.

31. The composition of claim 1, comprising no fish meal.

32. The composition of claim 1, wherein the predator fish would not subsist on the composition in absence of the bacterial species.

33. The composition of claim 1, which is substantially free of free amino acids.

34. The composition of claim 1, comprising a mixture of more than one bacterial species.

35. The composition of claim 1, comprising at least one *Acidovorax* species, at least one *Aeromonas* species, and at least one *Citrobacter* species.

* * * * *